US011553871B2

(12) United States Patent
Craik et al.

(10) Patent No.: US 11,553,871 B2
(45) Date of Patent: Jan. 17, 2023

(54) SYSTEM AND APPARATUS FOR NON-INVASIVE MEASUREMENT OF TRANSCRANIAL ELECTRICAL SIGNALS, AND METHOD OF CALIBRATING AND/OR USING SAME FOR VARIOUS APPLICATIONS

(71) Applicant: Lab NINE, Inc., Houston, TX (US)

(72) Inventors: Alexander R. Craik, Houston, TX (US); Joseph F. Arand, Chicago, IL (US); Alexander K. Arrow, Lakeside, CA (US)

(*) Notice: Subject to any disclaimer, the term of this patent is extended or adjusted under 35 U.S.C. 154(b) by 332 days.

(21) Appl. No.: 16/889,660

(22) Filed: Jun. 1, 2020

(65) Prior Publication Data

US 2020/0383598 A1 Dec. 10, 2020

Related U.S. Application Data

(60) Provisional application No. 62/857,263, filed on Jun. 4, 2019.

(51) Int. Cl.
*A61B 5/00* (2006.01)
*A61B 5/369* (2021.01)
*A61B 5/316* (2021.01)

(52) U.S. Cl.
CPC .............. *A61B 5/369* (2021.01); *A61B 5/316* (2021.01)

(58) Field of Classification Search
CPC ......... A61B 5/369; A61B 5/316; A61B 5/375; A61B 5/165
See application file for complete search history.

(56) References Cited

U.S. PATENT DOCUMENTS

| 5,243,517 A | 9/1993 | Schmidt et al. |
| 5,331,969 A | 7/1994 | Silberstein |
| 5,339,826 A | 9/1994 | Schmidt et al. |
| 5,601,090 A | 2/1997 | Musha |

(Continued)

FOREIGN PATENT DOCUMENTS

| EP | 1139240 | 10/2001 |
| WO | WO 97/33515 | 9/1997 |

(Continued)

OTHER PUBLICATIONS

Craik et al., "Deep learning for electroencephalogram (EEG) classification tasks: a review", Journal of Neural Engineering, vol. 16, No. 3, Apr. 4, 2019 (Apr. 9, 2019).

*Primary Examiner* — Ojiako K Nwugo

(57) ABSTRACT

Apparatuses and methods for non-invasively detecting and classifying transcranial electrical signals are disclosed herein. In an embodiment, system for detecting and interpreting transcranial electrical signals includes: a headset including a plurality of electrodes arranged for detection of the user's transcranial electrical signals; a display configured to display information to the user while the user wears the headset; and a control unit programmed to: (i) receive data relating to the transcranial electrical signals detected by the electrodes of the headset; (ii) create a data matrix with the received data; (iii) convert the data matrix into one or more user values; (iv) define a user output state based on the one or more user values; and (iv) cause alteration of an aspect of the display based on the user output state.

6 Claims, 30 Drawing Sheets

(56) References Cited

U.S. PATENT DOCUMENTS

| | | |
|---|---|---|
| 5,676,138 A | 10/1997 | Zawilinski |
| 5,724,987 A | 3/1998 | Gevins et al. |
| 5,899,867 A | 5/1999 | Collura |
| 6,021,346 A | 2/2000 | Ryu |
| 6,097,981 A | 8/2000 | Freer |
| 6,129,681 A | 10/2000 | Kuroda et al. |
| 6,190,314 B1 | 2/2001 | Ark et al. |
| 6,292,688 B1 | 9/2001 | Patton |
| 6,349,231 B1 | 2/2002 | Musha |
| 6,434,419 B1 | 8/2002 | Gevins et al. |
| 6,487,444 B2 | 11/2002 | Mimura |
| 6,656,116 B2 | 12/2003 | Kim et al. |
| 7,333,969 B2 | 2/2008 | Lee et al. |
| 7,547,279 B2 | 6/2009 | Kim et al. |
| 7,654,901 B2 | 2/2010 | Breving et al. |
| 7,865,235 B2 | 1/2011 | Le et al. |
| 8,155,736 B2 | 4/2012 | Sullivan et al. |
| 8,230,457 B2 | 7/2012 | Lee et al. |
| 8,332,883 B2 | 12/2012 | Lee et al. |
| 8,347,326 B2 | 1/2013 | Weitzenfeld et al. |
| 8,391,966 B2 | 3/2013 | Luo et al. |
| 8,392,254 B2 | 3/2013 | Pradeep et al. |
| 8,473,044 B2 | 6/2013 | Lee et al. |
| 8,494,905 B2 | 7/2013 | Pradeep et al. |
| 8,700,009 B2 | 4/2014 | Quy |
| 8,782,681 B2 | 7/2014 | Lee et al. |
| 8,788,495 B2 | 7/2014 | Shu |
| 8,793,715 B1 | 7/2014 | Weitzenfeld et al. |
| 8,939,903 B2 | 1/2015 | Roberts et al. |
| 9,215,996 B2 | 12/2015 | Lee et al. |
| 9,320,450 B2 * | 4/2016 | Badower .............. A41F 1/002 |
| 9,351,658 B2 * | 5/2016 | Lee ...................... A61B 5/742 |
| 9,521,960 B2 | 12/2016 | Lee et al. |
| 9,603,564 B2 | 3/2017 | Forbes |
| 9,622,703 B2 * | 4/2017 | Badower .............. A61B 5/316 |
| 9,668,694 B2 | 6/2017 | Badower |
| 9,833,184 B2 | 12/2017 | Derchak et al. |
| 9,936,250 B2 | 4/2018 | Marci et al. |
| 10,009,644 B2 | 6/2018 | Aimone et al. |
| 10,108,264 B2 | 10/2018 | Le et al. |
| 10,176,894 B2 | 1/2019 | Park et al. |
| 10,285,634 B2 | 5/2019 | Jain et al. |
| 10,321,842 B2 | 6/2019 | Garten et al. |
| 10,433,793 B1 * | 10/2019 | Rhoades ............. A61B 5/7275 |
| 10,485,470 B2 * | 11/2019 | Dolev ................ A61N 1/36025 |
| 10,874,870 B2 * | 12/2020 | Helekar .............. A61B 5/369 |
| 10,960,210 B2 * | 3/2021 | Srivastava ......... A61N 1/36071 |
| 11,052,252 B1 * | 7/2021 | Howard ............... A61B 5/369 |
| 11,344,723 B1 * | 5/2022 | Roach .................. A61N 1/025 |
| 11,364,361 B2 * | 6/2022 | Poltorak .............. A61B 5/245 |
| 2003/0028383 A1 | 2/2003 | Guerin et al. |
| 2003/0171689 A1 | 9/2003 | Millan et al. |
| 2005/0143629 A1 | 6/2005 | Farwell |
| 2006/0257834 A1 | 11/2006 | Lee et al. |
| 2007/0173733 A1 | 7/2007 | Le et al. |
| 2007/0203426 A1 | 8/2007 | Kover et al. |
| 2008/0065468 A1 | 3/2008 | Berg et al. |
| 2008/0177197 A1 | 7/2008 | Lee et al. |
| 2008/0023528 A1 | 9/2008 | Aarts et al. |
| 2008/0213736 A1 | 9/2008 | Morris |
| 2008/0218472 A1 | 9/2008 | Breen et al. |
| 2008/0221969 A1 | 9/2008 | Lee et al. |
| 2008/0025594 A1 | 10/2008 | Genco et al. |
| 2008/0253996 A1 | 10/2008 | Boschert et al. |
| 2008/0295126 A1 | 11/2008 | Lee et al. |
| 2009/0083129 A1 | 3/2009 | Pradeep et al. |
| 2009/0133047 A1 | 5/2009 | Lee et al. |
| 2009/0150919 A1 | 6/2009 | Lee et al. |
| 2009/0264785 A1 * | 10/2009 | Causevic ............. A61B 5/369 |
| | | 600/544 |
| 2010/0016753 A1 | 1/2010 | Firlik |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0282231 A1 | 11/2011 | Pradeep et al. |
| 2012/0035765 A1 * | 2/2012 | Sato ........................ G06F 3/015 |
| | | 600/300 |
| 2014/0114165 A1 * | 4/2014 | Walker ................... A61B 3/113 |
| | | 600/383 |
| 2014/0148657 A1 * | 5/2014 | Hendler ................. A61B 5/291 |
| | | 600/545 |
| 2014/0194726 A1 | 7/2014 | Mishelevich et al. |
| 2015/0081225 A1 * | 3/2015 | Keady .................... A61B 5/369 |
| | | 702/19 |
| 2017/0053296 A1 | 2/2017 | Lee et al. |
| 2018/0088903 A1 | 3/2018 | Mihajlovic et al. |
| 2018/0184937 A1 | 7/2018 | Kaddan et al. |
| 2018/0240157 A1 | 8/2018 | Gopalakrishnan |
| 2018/0303370 A1 | 10/2018 | Kanayama et al. |
| 2018/0348863 A1 | 12/2018 | Aimone et al. |
| 2019/0018488 A1 | 1/2019 | Le et al. |
| 2019/0082990 A1 * | 3/2019 | Poltorak .............. A61B 5/7267 |
| 2019/0096279 A1 | 3/2019 | Lau |
| 2019/0113973 A1 * | 4/2019 | Coleman ................. H04L 12/16 |
| 2019/0174039 A1 | 6/2019 | Jung et al. |
| 2019/0247662 A1 * | 8/2019 | Poltorak .............. A61B 5/0816 |
| 2019/0286234 A1 * | 9/2019 | Condolo ............ G06Q 30/0242 |
| 2019/0321583 A1 * | 10/2019 | Poltorak ................ A61B 5/369 |
| 2020/0289837 A1 * | 9/2020 | Lowin ................... A61B 5/6803 |
| 2021/0035665 A1 * | 2/2021 | Hirayama ............ G16H 10/60 |

FOREIGN PATENT DOCUMENTS

| | | |
|---|---|---|
| WO | WO 01/07128 | 2/2001 |
| WO | WO 01/86403 | 11/2001 |

* cited by examiner

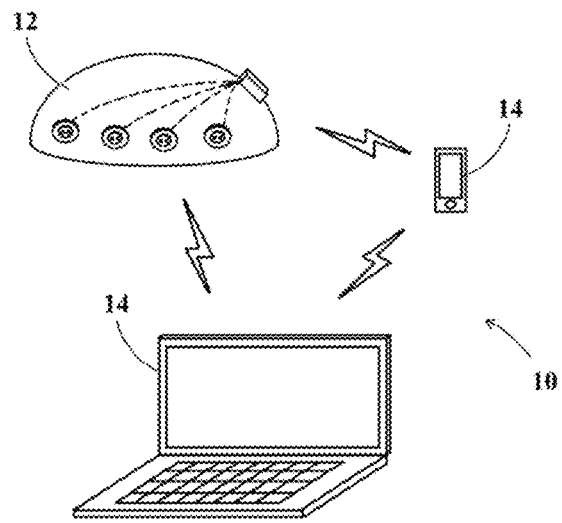
FIG. 1
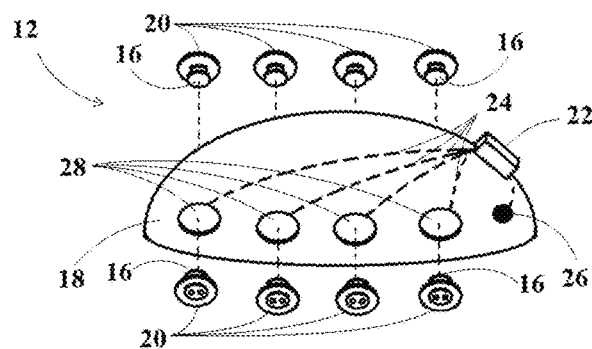 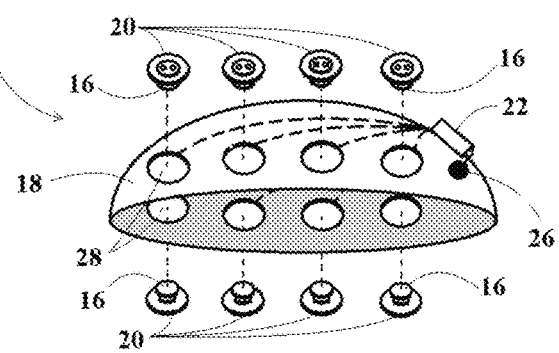
FIG. 2 FIG. 3

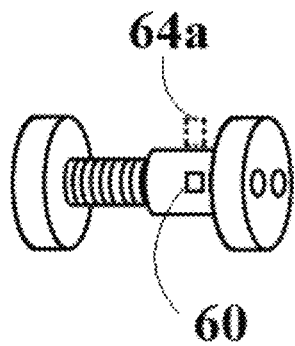 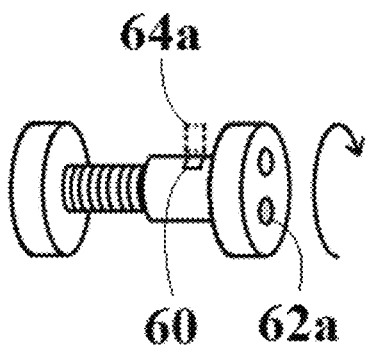 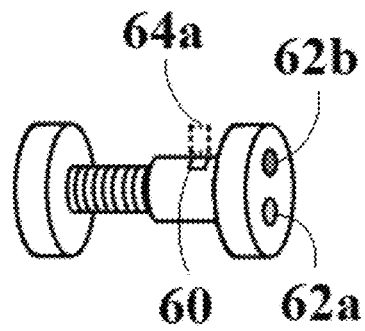
FIG. 10A  FIG. 10B  FIG. 10C
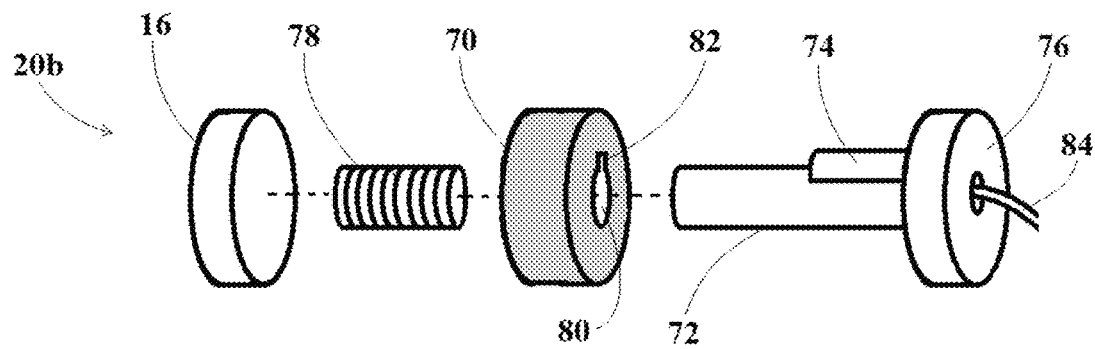
FIG. 11A
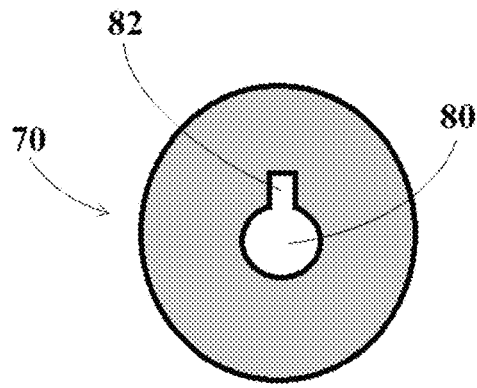
FIG. 11B

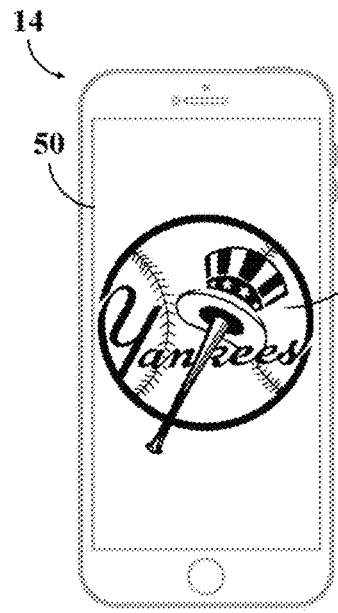
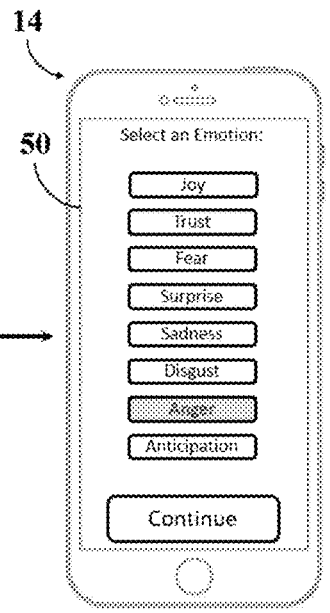
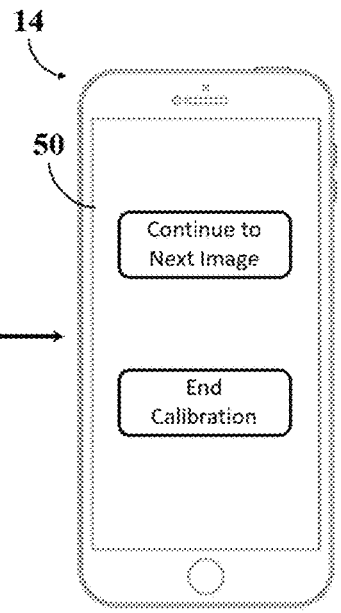
FIG. 21D     FIG. 21E     FIG. 21F
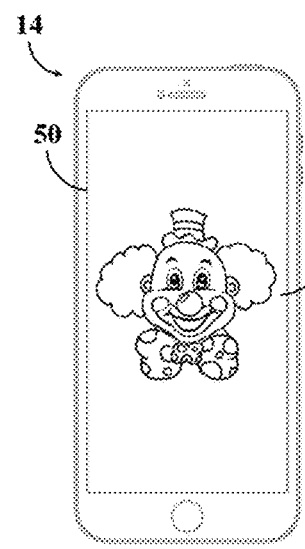
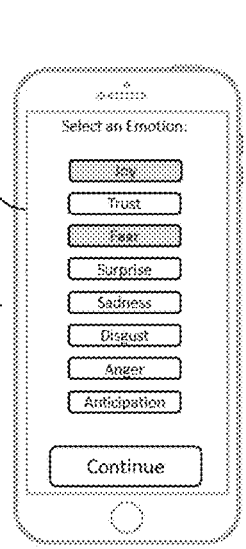
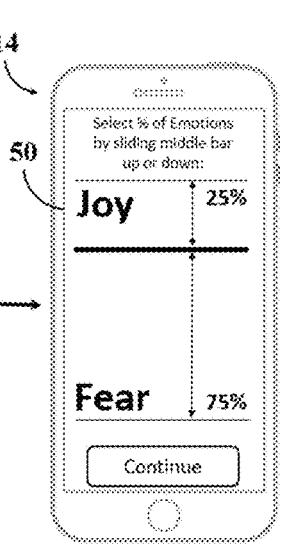
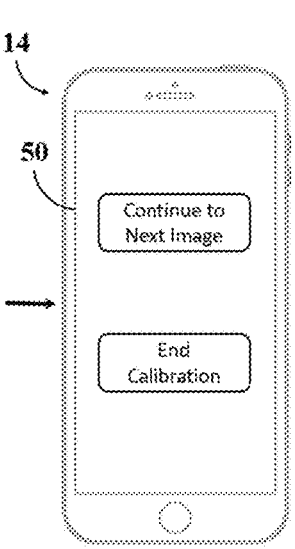
FIG. 22A    FIG. 22B    FIG. 22C    FIG. 22D

SYSTEM AND APPARATUS FOR NON-INVASIVE MEASUREMENT OF TRANSCRANIAL ELECTRICAL SIGNALS, AND METHOD OF CALIBRATING AND/OR USING SAME FOR VARIOUS APPLICATIONS

PRIORITY

This patent application claims priority to U.S. Provisional Patent Application No. 62/857,263, filed Jun. 4, 2019, entitled "Apparatus for Non-invasive Measurement of Transcranial Electrical Signals, and Method of Calibrating and/or Using Same to Classify Emotional States for Various Applications," the entirety of which is incorporated herein by reference and relied upon.

FIELD OF THE DISCLOSURE

The present disclosure relates generally to apparatuses and methods for non-invasively detecting and classifying transcranial electrical signals, and more specifically to apparatuses and methods for detecting and classifying transcranial electrical signals for use in various applications such as determining emotional states or controlling images, videos and/or audio, for example, to be used in therapy sessions, for entertainment purposes, in video games, to create musical compositions, for market research, for medical treatment, and/or for other purposes.

BACKGROUND

Electroencephalography (EEG) is typically used in research involving neural engineering, neuroscience, and biomedical engineering. With EEG sensors, cognitive states can be detected and broken down into data which can be useful for a variety of purposes.

Although emotional states are often outward and evident, demonstrated by crying, laughing, blushing, and a variety of other facial expressions and body language, emotional states may not always be obvious by appearance and actions in certain persons even though psychological changes are taking place. Many people also exhibit emotional states in different manners, or attempt to hide their emotional states from those around them, making it difficult to interpret emotional states based on appearance alone. Further, there are often minor differences between different emotional states which may not cause different physical reactions in a person.

Thought patterns other than emotional states, such as desires to make intentional kinetic motions, also result in brain wave activity detectable with EEG sensors while not outwardly evident.

SUMMARY

The present disclosure proposes apparatuses and methods for non-invasively detecting and classifying transcranial electrical signals. It is advantageous, for example, for therapeutic and entertainment purposes, to be able to use EEG data to determine a person's cognitive states in ways besides simply viewing that person's expression and body language. This is specifically applicable to the determination of a person's emotional state, as a subjective analysis of a person's emotional state based on visual evidence may not be reliable. It is also advantageous to be able to use EEG data to control images, videos, audio, and/or virtual avatars, for example, to be used in therapy sessions, for entertainment purposes, in video games, to create musical compositions, for market research, for medical treatment, and/or for other purposes. For example, EEG sensors offer the possibility of an individual using thought patterns to make volitional motions in a linked device, with applications in video games by moving an avatar-like screen representation, musical composition by mentally choosing notes and timing, and computer programming by writing code without typing.

In a general example embodiment, system for detecting and interpreting transcranial electrical signals includes a headset configured to be placed on a user's head, the headset including a plurality of electrodes arranged for detection of the user's transcranial electrical signals, a display configured to display information to the user while the user wears the headset, and a control unit in operative communication with the headset and the display, the control unit programmed to: (i) receive data relating to the transcranial electrical signals detected by the electrodes of the headset; (ii) create a data matrix with the received data; (iii) convert the data matrix into one or more user values; (iv) define a user output state based on the one or more user values; and (iv) alter an aspect of the display based on the user output state.

In another general example embodiment, a method for interpreting a user's transcranial electrical signals includes receiving data regarding the user's transcranial electrical signals, creating a data matrix from the data regarding the user's transcranial electrical signals, processing the data matrix into one or more user values, defining a user output state based on the one or more user values, and exhibiting the user output state.

In another general example embodiment, a method for interpreting a user's transcranial electrical signals includes receiving data regarding the user's transcranial electrical signals, creating a data matrix from the data regarding the user's transcranial electrical signals, converting the data matrix into a first user value, converting the data matrix into a second user value, defining a user output state based on the first user value and the second user value, and exhibiting the user output state.

In another general example embodiment, a method for calibrating a neural analysis system to interpret a user's transcranial electrical signals includes detecting transcranial electrical signals from the user via at least one electrode, exhibiting an electronic medium for the user, creating a data matrix based on transcranial electrical signals detected by the at least one electrode during exhibition of the electronic medium, receiving user input regarding a user output state during exhibition of the electronic medium, and associating the at least one value with the data matrix to indicate the user output state during exhibition of the electronic medium.

In another general example embodiment, a system for detecting transcranial electrical signals includes a headset configured to be placed on a user's head, the headset including a plurality of electrodes arranged for detection of the user's transcranial electrical signals, a user interface configured to display information to the user or to others while the user wears the headset, and a control unit programmed to: (i) receive data relating to the transcranial electrical signals detected by the electrodes of the headset; (ii) determine the user's emotional state based on the received data; and (iii) cause the user interface to display the user's emotional state.

In another general example embodiment, a system for detecting transcranial electrical signals includes a body configured to fit to a user's head, the body including a plurality of apertures therethrough, and a plurality of electrode subassemblies, each electrode subassembly configured to be removeably attached to the body through a respective aperture of the plurality of apertures, wherein each electrode subassembly includes an electrode positioned to contact the user's head when the body is fitted over the user's head.

In another general example embodiment, a method of configuring a neural analysis system for detection of a user's emotions includes detecting transcranial electrical signals from the user via at least one electrode, classifying the user into a subtype from a subtype database based on an analysis of at least one transcranial electrical signal detected by the at least one electrode, performing a calibration procedure in which the user views a plurality of electronic mediums and inputs an emotional state felt during viewing of one or more of the plurality of electronic mediums, creating combined data by combining calibration data from the calibration procedure with subtype data from a subtype database based on the user's subtype classification, and training at least one neural network with the combined data to determine the user's emotional states based on subsequent transcranial electrical signals detected by the at least one electrode. In an embodiment, the subtype is an emotional subtype. Emotional subtype classification may be a useful endpoint in its own right, or may be an input into real-time processing to determine a user's current emotional state.

In another general example embodiment, a method of creating a subtype database to be used to configure a neural analysis system for a specific user includes detecting a plurality of transcranial electrical signals from a first user through a plurality of electrode channels, determining the most effective electrode channels for the first user, detecting a plurality of transcranial electrical signals from a second user through a plurality of electrode channels, determining the most effective electrode channels for the second user, and creating a subtype database based on the most effecting electrode channels for the first user and the second user.

In another general example embodiment, a method of determining a user's subtype to be used to configure a neural analysis system for the user includes detecting a plurality of transcranial electrical signals from the user through a plurality of electrode channels, determining the most effective electrode channels for the user, and determining a subtype for the user based on the most effecting electrode channels.

In another general example embodiment, a method for calibrating a neural analysis system to determine a user's emotional state includes detecting transcranial electrical signals from the user via at least one electrode, exhibiting an electronic medium for the user, creating at least one data matrix based on the transcranial electrical signals detected by the at least one electrode during exhibition of the electronic medium, receiving a user input regarding the user's emotional state during exhibition of the electronic medium, and converting the user input into an arousal value and a valence value corresponding to the data matrix based on the transcranial electrical signals.

In another general example embodiment, a method for calibrating a neural analysis system to determine a user's emotional state includes detecting transcranial electrical signals from the user via at least one electrode, exhibiting an electronic medium for the user, creating a data matrix based on transcranial electrical signals detected by the at least one electrode during exhibition of the electronic medium, receiving a user input including an arousal value and a valence value regarding the user's emotional state during exhibition of the electronic medium, and associating the arousal value and the valence value with the data matrix to indicate the user's emotional state during exhibition of the electronic medium.

In another general example embodiment, a method of configuring a neural analysis system for detection of a user's emotional states includes receiving user data, the user data including a plurality of data matrices each associated with an arousal value and a valence value, receiving subgroup data, the subgroup data including a plurality of data matrices each associated with an arousal value and a valence value, dividing the user data into a first portion of user data and a second portion of user data, each of the first portion of user data and the second portion of user data including a plurality of data matrices each associated with an arousal value and a valence value, creating combined data by combining the subgroup data with the first portion of user data, training at least one neural network, using the combined data, to output an arousal value and a valence value when receiving one or more subsequent data matrix, inputting the data matrices from the second portion of user data into the trained at least one neural network, and validating the trained at least one neural network based on whether an actual output from the at least one trained neural network is within a range of an expected output based on the second portion of user data.

In another general example embodiment, a method of determining a user's emotional state by detecting transcranial electrical signals includes detecting transcranial electrical signals from the user via at least one electrode, creating at least one data matrix from the transcranial electrical signals, determining an arousal value using the at least one data matrix, determining a valence value using the at least one data matrix, and determining an emotional state for the user based on the arousal value and the valence value.

In another general example embodiment, a system for determining an emotional response from a plurality of users includes a first headset configured to be placed on a first user's head, the first headset including a plurality of first electrodes arranged for detection of the first user's transcranial electrical signals, a second headset configured to be placed on a second user's head, the second headset including a plurality of second electrodes arranged for detection of the second user's transcranial electrical signals, at least one user interface configured to display information to at least one of the first user and the second user while the first headset and the second headset are worn, and a control unit programmed to: (i) receive first data relating to the transcranial electrical signals detected by the plurality of first electrodes of the first headset; (ii) receive second data relating to the transcranial electrical signals detected by the plurality of second electrodes of the second headset; (iii) determine the first user's emotional state based on the first data and the second user's emotional state based on the second data; and (iv) determine an emotional state felt by both the first user and the second user simultaneously during one or more time periods.

In another general example embodiment, a method of determining an emotional response from a plurality of users includes positioning a plurality of first electrodes to detect transcranial electrical signals from a first user, determining a first emotional state for the first user based on the transcranial electrical signals detected with the plurality of first electrodes, positioning a plurality of second electrodes to detect transcranial electrical signals from a second user, determining a second emotional state for the second user based on the transcranial electrical signals detected with the plurality of second electrodes, and transforming the first emotional state and the second emotional state into feedback data relating to an exhibited medium.

In another general example embodiment, a method of enhancing a video game based on the game player's emotional response to game elements includes detecting transcranial electrical signals from the game player while the game player is playing the video game, determining the game player's current emotional state based on the detected transcranial electrical signals, and causing an avatar in the video game to reflect the game player's current emotional state.

In another general example embodiment, a video game system includes a headset configured to be placed on a user's head, the headset including a plurality of electrodes arranged for detection of the first user's transcranial electrical signals, and a video game system including a control unit, the control unit programmed to: (1) enable the user to play a video game on a monitor; (ii) receive data relating to the transcranial electrical signals detected by the plurality of electrodes of the headset while the video game is displayed on the monitor; (iii) determine the user's emotional state based on the data; and (iv) cause a change in the video game displayed on the monitor based on the user's emotional state.

In another general example embodiment, a medical device includes a headset configured to be placed on a user's head, the headset including at least one electrode arranged for detection of the user's transcranial electrical signals, a drug delivery device placed in communication with the headset, the drug delivery device configured to deliver a medicament to the user, and a control unit programmed to: (i) receive data relating to the transcranial electrical signals detected by the at least one electrode of the headset; and (ii) cause the drug delivery device to deliver the medicament to the user based on the received data.

In another general example embodiment, a system for detecting transcranial electrical signals includes a headset configured to be placed on a user's head, the headset including at least one electrode arranged for detection of the user's transcranial electrical signals, a user interface configured to display information to the user while the user wears the headset, and a control unit programmed to: (i) receive data relating to the transcranial electrical signals detected by the electrodes of the headset; (ii) determine the user's emotional state based on the received data; and (iii) cause the user interface to display the user's emotional state.

BRIEF DESCRIPTION OF THE FIGURES

Embodiments of the present disclosure will now be explained in further detail by way of example only with reference to the accompanying figures, in which:

FIG. 1 illustrates an example embodiment of a neural analysis system according to the present disclosure;

FIG. 2 illustrates an exploded top perspective view of an example embodiment of the headset of the neural analysis system of FIG. 1;

FIG. 3 illustrates an exploded bottom perspective view of an example embodiment of the headset of the neural analysis system of FIG. 1;

FIG. 10A illustrates an example embodiment of the electrode subassembly of FIG. 8A in an OFF position;

FIG. 10B illustrates an example embodiment of the electrode subassembly of FIG. 8A in an ON position;

FIG. 10C illustrates an example embodiment of the electrode subassembly of FIG. 8A indicating that the electrode should be replaced;

FIG. 11A illustrates an exploded side perspective view of an example embodiment of an electrode subassembly which may be included as part of the headset of FIG. 1;

FIG. 11B illustrates a front view of an example embodiment of a sleeve that may form part of the electrode subassembly of FIG. 11A;

FIGS. 21A to 21F illustrate an example embodiment of a user interface during the method of FIG. 20A;

FIGS. 22A to 22D illustrate example embodiments of a user interface during the method of FIG. 20A;

DETAILED DESCRIPTION

Figure 4:
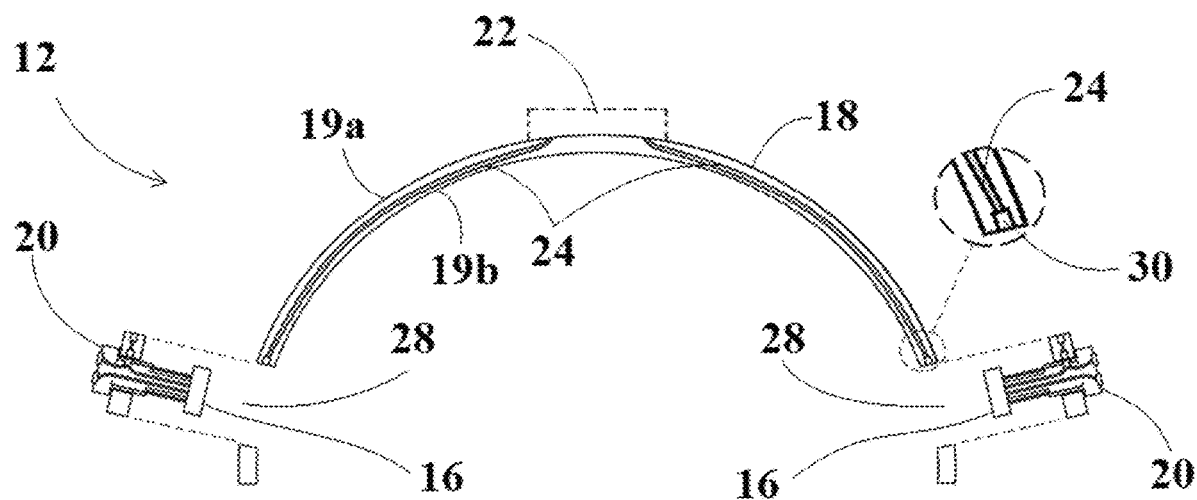
FIG. 4 illustrates an exploded cross-sectional view taken through the center of an example embodiment of the headset of the neural analysis system of FIG. 1.

Before the disclosure is described, it is to be understood that this disclosure is not limited to the particular apparatuses and methods described. It is also to be understood that the terminology used herein is for the purpose of describing particular embodiments only, and is not intended to be limiting, since the scope of the present disclosure will be limited only to the appended claims.

As used in this disclosure and the appended claims, the singular forms "a," "an" and "the" include plural referents unless the context clearly dictates otherwise. The methods and apparatuses disclosed herein may lack any element that is not specifically disclosed herein.

FIG. 1 illustrates an example embodiment of a neural analysis system 10 according to the present disclosure. In the illustrated embodiment, neural analysis system 10 includes a headset 12 and one or more electronic device 14. In use, headset 12 arranges a plurality of electrodes 16 against a user's head, so that transcranial electrical signals may be detected from the user. As set forth in more detail below, headset 12 may then transmit the detected transcranial electrical signals to the one or more electronic device 14 to be transformed into useable data for various applications. In an embodiment, neural analysis system 10 may include a plurality of electronic devices 14 which are in communication with each other as well as with headset 12.

FIGS. 2 to 5 illustrate an example embodiment of headset 12. In the illustrated embodiment, headset 12 includes a body 18, a plurality of electrode subassemblies 20, and a data transmission device 22. The plurality of electrode subassemblies 20 may be removeably attached to headset 12 through apertures 28 in body 18, or may be attached to the inner surface of body 18 at locations in which useful transcranial electrical signals may be detected. In an embodiment, any electrode subassembly 20 may be interchangeably attached through any aperture 28. This removeability and interchangeability of the electrode subassemblies is advantageous, for example, because the user may simply replace a malfunctioning electrode 16 or electrode subassembly 20 as opposed to an entire headset 12 if there is a problem with only one electrode 16 or electrode subassembly 20.

In the illustrated embodiment, headset 12 includes eight (8) electrodes 16, with each electrode subassembly 20 including one (1) electrode 16. In alternative embodiments, headset 12 may include, for example, sixteen (16), thirty-two (32) or sixty-four (64) electrodes. Those of ordinary skill in the art will recognize from this disclosure that the more electrodes 16 that are used, the more data points there are that are gained from the transcranial electrical signals, making the resulting dataset more accurate. At the same time, the more electrodes 16 that are used, the more expensive headset 12 will be to manufacture and replace. It has therefore been determined that eight (8) electrodes generate a dataset that provides sufficiently confident results while keeping cost relatively low. In an embodiment, the electrodes 16 may be positioned on body 18 according to the guidelines recommended by the international 10-20 system for electrode placement. Although the embodiment of FIGS. 2 to 5 shows the apertures 28 and electrode subassemblies 20 uniformly positioned at the same height around the perimeter of headset 12, it should be understood that the positioning of the apertures 28 and thus the electrode subassemblies 20 may not be uniform and may occur at different heights and distances.

In the illustrated embodiment, the electrodes 16 are dry electrodes, which enable the user of neural analysis system 10 to use headset 12 with less preparation and/or cleanup. In an alternative embodiment, headset 12 may utilize wet electrodes.

In the illustrated embodiment, headset 12 further includes a motion device 26, for example an accelerometer, which may be used to remove artifacts from the transcranial electrical signals recorded from electrodes 16. In an embodiment, neural analysis system 10 may determine when movement of a user wearing headset 12 crosses a threshold based on an output from motion device 26, and then discard or scale down the data recorded by electrodes 16 at that time, knowing that the data may be inaccurate due to the user's movement. In another embodiment, a motion device 26, for example one or more electrooculography (EOG) sensor, may be placed near or contacting the user's eyes and used to remove artifacts from the signals recorded from electrodes 16. Eye movement may generate a high amplitude, low frequency transcranial electrical signal which may interfere with one or more electrode 16 and thus be advantageous to remove.

In the illustrated embodiment, body 18 of headset 12 is a solid surface that curves over the top of the user's head. By forming body 18 as a solid surface, the design may advantageously eliminate some or all potentially interfering electrical signals from outside headset 12, preventing crosstalk that could interfere with the transcranial electrical signals recorded from electrodes 16.

In an embodiment, headset 12 may include a ground and/or a reference for the electrodes. The ground may be used for common mode rejection, for example, to prevent noise from interfering with transcranial electrical signals. The reference may be used, for example, to measure voltage drops. In an embodiment, the ground and/or reference may be located on headset 12 and/or a separate element such as an ear clip.

Figure 5:
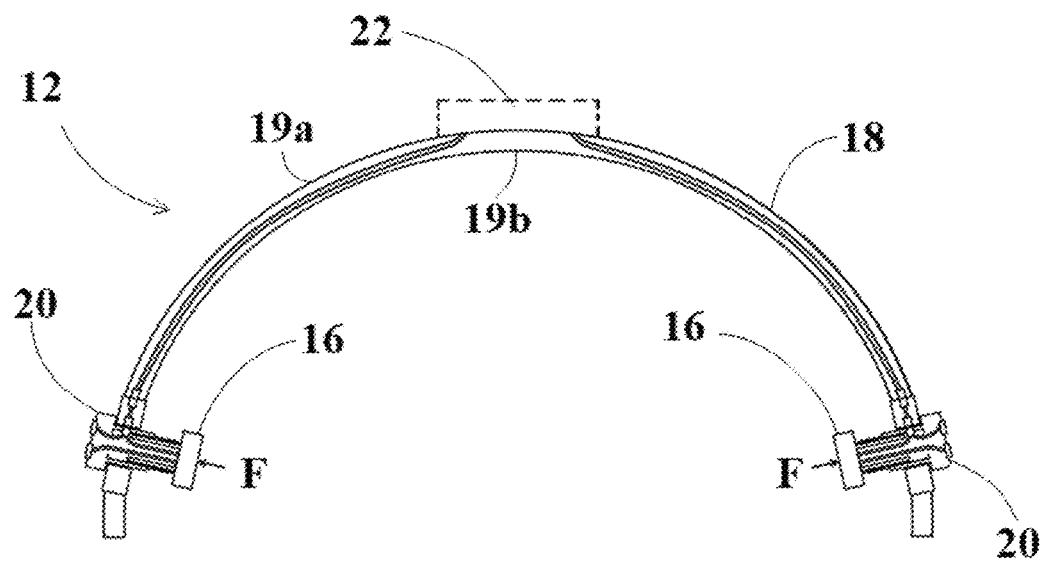
FIG. 5 illustrates a cross-sectional view taken through the center of an example embodiment of the headset of the neural analysis system of FIG. 1.

FIGS. 4 and 5 illustrate a cross-sectional view of headset 12. As illustrated, electrode subassemblies 20 attach to body 18 through apertures 28. In an embodiment, each electrode subassembly 20 may attach to an aperture 28, for example, by a snap-fit connection, a threaded connection, or another connection known in the art.

When an electrode subassembly 20 is attached to body 18, the electrode 16 attached thereto may be placed in electronic communication with data transmission device 22, so that data from the electrode 16 may be transmitted to an electronic device 14. As illustrated in FIGS. 4 and 5, headset 12 may include wiring 24 to place each electrode 16 in electronic communication with data transmission device 22. In the illustrated embodiment, wiring 24 runs between the inner surface 19a and the outer surface 19b of body 18, but wiring 24 may be placed outside of the inner surface 19a or the outer surface 19b as well. In an alternative embodiment, each electrode subassembly 20 may wirelessly communicate with data transmission device 22.

In the illustrated embodiment, the surface of each aperture 28 of body 18 includes an electrical contact 30, which is wired to data transmission device 22 via wiring 24. When an electrode subassembly 20 is attached to an aperture 28, an electrical contact of the electrode subassembly 20 may contact the electrical contact 30 of aperture 28, thus placing the electrode 16 in electrical communication with data transmission device 22. By structuring headset 12 in this way, electrodes 16 may be quickly replaced by a user without the user having to fumble with wiring to connect the electrode 16.

As illustrated in FIG. 5, an attached electrode subassembly 20 positions an electrode 16 to contact a patient's head. In an embodiment, once attached to body 18, all or a portion of the plurality of electrode subassemblies 20 may be moveable in relation to body 18 so that they may be urged towards the user's head for contact with the user's head or retracted away from the user's head when headset 12 is fitted to the user and/or stored. As discussed in more detail below, each electrode 16 may be attached to electrode subassembly 20 and/or another element of headset 12 using one or more of a translating and/or biasing element, with the translating element enabling the user's head to push the electrode 16 towards headset 12 with a force F, while the biasing element biases electrode 16 in the opposite direction back toward the user's head to ensure contact with the user's head.

In an embodiment, each electrode subassembly 20 may include or be associated with a position sensor that determines how far the electrode 16 has been translated by the user's head. By determining how far the user's head pushes each of the plurality of electrodes 16, the user's head type can be classified and used to calibrate headset 12 for use, as explained in more detail below. In an embodiment, the positions of more than one of the plurality of electrodes 16 enable determination of an overall head size and/or head type when combined together.

Figure 6:
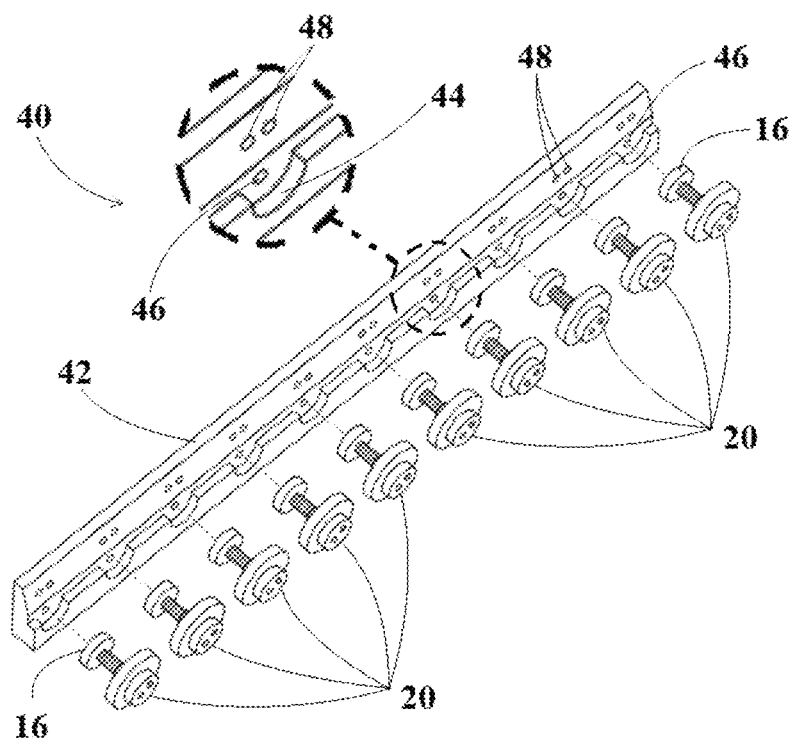
FIG. 6 illustrates a perspective view of an example embodiment of an electrode testing apparatus for use with the headset of the neural analysis system of FIG. 1.
Figure 7:
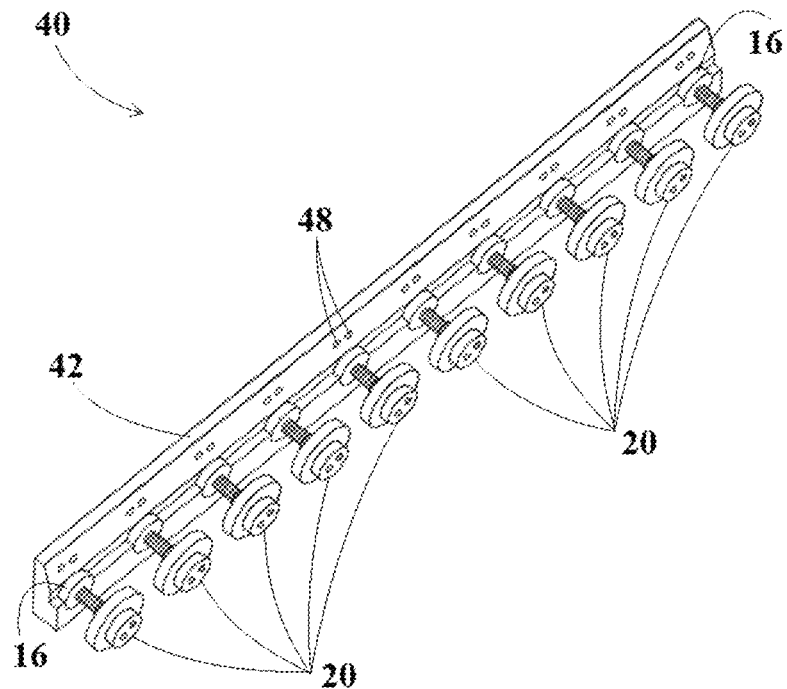
FIG. 7 illustrates a perspective view of an example embodiment of an electrode testing apparatus for use with the headset of the neural analysis system of FIG. 1.
Figure 8A:
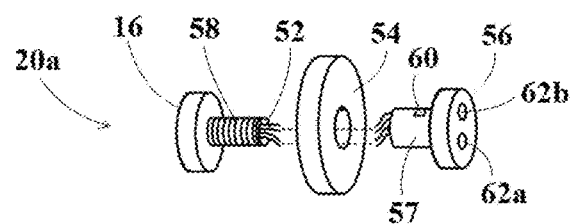
FIG. 8A illustrates an exploded side perspective view of an example embodiment of an electrode subassembly which may be included as part of the headset of FIG. 1.
Figure 8B:
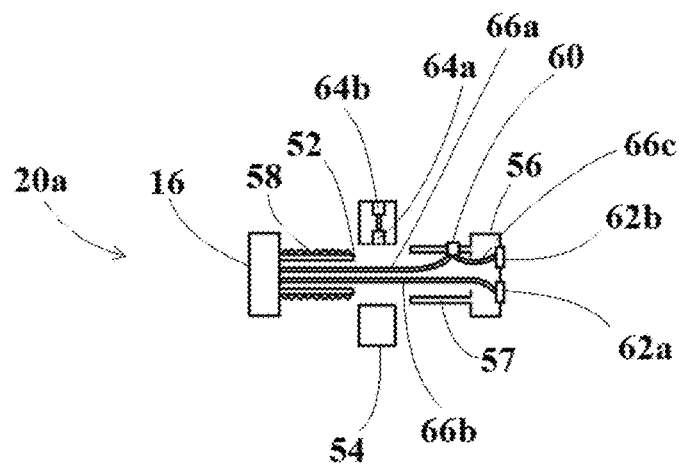
FIG. 8B illustrates an exploded cross-sectional view of the electrode subassembly of FIG. 8A.

FIGS. 6 and 7 illustrate an electrode testing station 40 which is configured to test each electrode 16 prior to use. In an embodiment, electrode testing station 40 tests each electrode 16 by detecting the impedance of each electrode 16 and informing the user when an electrode 16 is unsuitable for use if the impedance is above a threshold. By utilizing electrode testing station 40, the user may test the electrodes 16 prior to placing them in a headset 12, saving the user time if an electrode 16 is faulty. In the illustrated embodiment, electrode testing station 40 is formed as an elongated strip that may be mounted on a wall for convenience of storage, but other shapes and sizes may also be used.

In the illustrated embodiment, testing station 40 includes a body 42 having a slot 44 for each electrode to be tested. In an embodiment, body 42 may include only a single slot 44 for each electrode 16 to be tested individually, but the illustrated embodiment includes a plurality of slots so that a plurality of electrodes 16 may be tested simultaneously. Each slot 44 may further include an electrical contact 46 and/or an indicator 48 to indicate whether the electrode 16 is in suitable condition for use with headset 12.

In the illustrated embodiment, each electrode subassembly 20 is placed into electrode testing station 40 so that the electrode 16 enters a slot 44 and is placed into contact with electrical contact 46. In alternative embodiments, each electrode subassembly 20 may be placed into electrode testing station 40 so that another element of electrode subassembly 20 places the electrode 16 in electrical communication with electrical contact 46 or another element of testing station 40. When electrode 16 is placed into slot 44, electrode testing station 40 may test the electrode 16, for example, by measuring the impedance of the electrode 16. If the impedance is above a threshold, indicator device 48 may indicate that the electrode 16 is not suitable to use and should be replaced or discarded. If the impedance is below a threshold, indicator device 48 may indicate that the electrode 16 is suitable for use and may be attached to body 18 of headset 12. In the illustrated embodiment, indicator device 48 includes two visual indicators (e.g., lights), with one visual indicator indicating that the electrode 16 is suitable for use, and the other visual indicator indicating that the electrode 16 is unsuitable for use. More or less indicators may be used. In another embodiment, indicator device 48 may indicate a level of degradation and/or inform the user of the impedance value for each electrode 16 so that the user may estimate how much life an electrode 16 has left.

In the illustrated embodiment, electrode testing station 40 includes more slots 44 than the number of electrodes 16 used by headset 12, for example, ten (10) slots 44 for ten (10) electrodes 16 to be tested by electrode testing station 40 simultaneously. Since the embodied headset 12 uses eight (8) electrodes 16, the present embodiment of an electrode testing station 40 enables the user to use headset 12 even if two (2) of the tested electrodes 16 are faulty and need to be replaced.

FIGS. 8A, 8B, 9A, 9B and 10A to 10C illustrate an example embodiment of an electrode subassembly 20a. In the illustrated embodiment, electrode subassembly 20a includes an electrode 16, a first shaft 52, a sleeve 54, a cap 56 including a second shaft 57, a biasing element 58, a first electrical contact 60, and one or more indicator device 62a, 62b. As illustrated, the electrode 16 may be electrically connected to first electrical contact 60 via a first wire 66a and to first indicator device 62a via a second wire 66b, and second indicator device 62b may be electrically connected to first electrical contact 60 and/or electrode 16 via a third wire 66c. Those of ordinary skill in the art may recognize from this disclosure other wiring arrangements that achieve the same purpose as described herein.

Figure 9A:
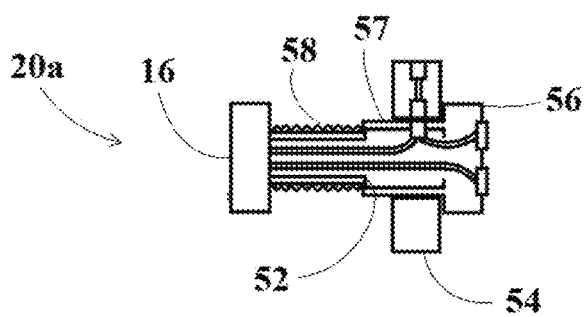
FIG. 9A illustrates a cross-sectional view of the electrode subassembly of FIG. 8A fully extended toward a user's head.
Figure 9B:
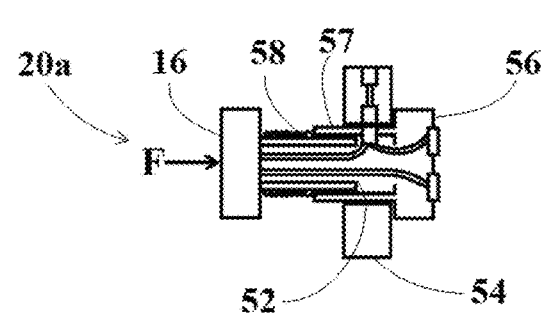
FIG. 9B illustrates a cross-sectional view of the electrode subassembly of FIG. 8A compressed by a user's head.

In the illustrated embodiment, sleeve 54 fits around second shaft 57 and/or another portion of cap 56, enabling cap 56 to rotate within and/or with respect to sleeve 54. First shaft 52 then fits within or around second shaft 57 of cap 56, enabling first shaft 52 and electrode 16 attached thereto to translate with respect to cap 56. By enabling electrode 16 to translate with respect to cap 56, electrode subassembly 20a enables adjustment of the distance of electrode 16 toward and away from the user's head. When the user pushes his or her head into electrode 16 with a force F, as shown in FIG. 9B, electrode 16 retracts toward cap 56, but biasing element 58 biases electrode 16 in the opposite direction back toward the user's head and ensures that electrode 16 remains firmly in contact with the user's head even as electrode 16 retracts toward body 18. FIG. 9A illustrates electrode assembly 20 with a fully extended electrode 16 before the user has applied the force F, while FIG. 9B illustrates shaft 52 retracting when the user applies force F. In another embodiment, shaft 52 may translate into, translate over, or translate adjacent to second shaft 57 and/or another element of cap 56 and/or another intermediate element to enable electrode 16 to retract toward body 18 when a force F is applied by a user. As discussed above, electrode subassembly 20a may be associated with a position sensor to determine how far electrode 16 has been retracted and thus the user's head type.

It is advantageous for electrode 16 to remain in constant contact with a user's head during the detection of transcranial electrical signals. Biasing element 58, e.g. a spring, is configured to constantly bias electrode 16 toward the user's head, ensuring that electrode 16 is pressed against the user's head whenever headset 12 is worn. Biasing element may bias against sleeve 54, cap 56 or another element of electrode subassembly 20a and/or body 18 to urge electrode 16 toward a user's head during use.

FIGS. 10A to 10C illustrate an advantage of enabling cap 56 to rotate with respect to sleeve 54. In the illustrated embodiment, sleeve 54 includes a second electrical contact 64a connected to a third electrical contact 64b (see FIG. 8B), for example, via additional wiring. When sleeve 54 is attached to body 18 of headset 12, third electrical contact 64b may be placed into electrical communication with electrical contact 30 of body 18 (FIGS. 4 and 5). Cap 56 may then be rotated to place first electrical contact 60 into electrical communication with second electrical contact 64a (FIGS. 9A and 9B), which places electrode 16 into electrical connection with data transfer device 22 of headset 12 via: (1) the electrical communication between electrode 16 and first electrical contact 60; (ii) the electrical communication between first electrical contact 60 and second electrical contact 64a; (iii) the electrical communication between second electrical contact 64a and third electrical contact 64b; (iv) the electrical communication between third electrical contact 64b and electrical contact 30; and (v) the electrical communication between electrical contact 30 and data transmission device 22. Those of ordinary skill in the art will recognize from this disclosure other ways to place electrode 16 into electrical connection with data transfer device 22. For example, second electrical contact 64a and third electrical contact 64b may be a single element, first electrical contact 60 may directly contact electrical contact 30, and/or data from electrode 16 may be wirelessly sent to data transmission device 22. In an embodiment, second electrical contact 64a and/or third electrical contact 64b may include a conductive ring around or through sleeve 54, enabling electrical communication with electrical contact 30 regardless of how sleeve 54 is oriented when inserted into an aperture 28.

FIGS. 10A and 10B illustrate rotation of electrode subassembly 20a from an OFF position to an ON position. The positioning of second electrical contact 64a is shown in broken lines in FIGS. 10A and 10B, with the rest of sleeve 54 omitted for clarity. In FIG. 10A, electrode subassembly 20a is in the OFF position with electrode 16 not electrically connected to data transmission device 22, because first electrical contact 60 is not rotated to be placed in electrical communication with second electrical contact 64a. In FIG. 10B, electrode subassembly 20a is in the ON position because first electrical contact 60 has been rotated 90° (or, e.g., 30°, 45°, 180°, etc.) to be placed in electrical communication with second electrical contact 64a. FIG. 10C likewise shows electrode subassembly 20a in the ON position.

In an embodiment, a user may remove electrode subassembly 20a from headset 12 when electrode subassembly 20a is in the OFF position of FIG. 10A, and electrode subassembly 20a is locked into headset 12 when cap 56 is rotated into the ON position of FIGS. 10B and 10C. Electrode subassembly 20a may be locked into headset 12, for example, by a twist-and-lock feature that engages when cap 56 is rotated as illustrated between FIG. 10A and FIG. 10B.

In the illustrated embodiment, first indicator device 62a indicates that electrode 16 has indeed been placed into electrical communication with data transmission device 22. Thus, in FIG. 10B, first indicator device 62a has been illuminated to show that an electrical communication has indeed been made, that electrode 16 is operational, and/or that electrode subassembly 20 has been locked into body 18. In the illustrated embodiment, first indicator device 62a is a light that illuminates when the electrical communication between electrode 16 and data transmission device 22 is made, but those of ordinary skill in the art will recognize from this disclosure that other indicator devices may be substituted.

In the illustrated embodiment, second indicator device 62b indicates when the impedance of electrode 16 has risen above a predetermined threshold. If the impedance detected at electrode 16 is above the predetermined threshold, the electrode 16 and/or electrode subassembly 20a may need to be replaced before the headset 12 may be used. Thus, in FIG. 10C, second indicator device 62b has illuminated, giving the user a clear indication that electrode 16 needs to be replaced. In the illustrated embodiment, second indicator device 62b is a light that illuminates when the impedance of electrode 16 is too high, but those of ordinary skill in the art will recognize from this disclosure that other indicator devices may be substituted. In an alternative embodiment, second indicator device 62b may indicate the overall health of electrode 16 as opposed to simply whether a particular threshold has been crossed and/or user interface 50 of electronic device 14 may display the overall health of electrode 16.

Electrode 16 may deteriorate over time. Second indicator device 62b is therefore advantageous because it enables the user to know precisely when an electrode 16 has deteriorated to the point that it needs to be replaced. By including second indicator device 62b on each electrode subassembly 20a, the user may simply replace that electrode 16 and/or electrode subassembly 20a instead of replacing the entire headset 12. Moreover, with the illustrated detachable/interchangeable design, the user can easily remove the electrode 16 or electrode subassembly 20a in such a case, and simply replace that electrode 16 or electrode subassembly 20a. In an embodiment, first indicator device 62a emits a different signal compared to second indicator device 62b (e.g., different color, different shape, different icon) so that the user may easily distinguish between the two alerts.

In an embodiment, electrode subassembly 20a is attached to body 18 of headset 12 by attaching sleeve 54 to body 18 through aperture 28 (FIGS. 4 and 5). In an embodiment, sleeve 54 may be attached to body 18 via a snap-fit inside aperture 28. In another embodiment, sleeve 54 may be attached to body 18 by threading into aperture 28, for example, using threads on the surface of sleeve 54 and/or aperture 28. Those of ordinary skill in the art will recognize from this disclosure other suitable attachment mechanisms. In another embodiment, sleeve 54 may be part of body 18 and/or omitted, and/or first electrical contact 60 of cap 56 may directly contact electrical contact 30 of body 18 (FIGS. 4 and 5) when electrode subassembly 20a is attached to body 18 and/or rotated with respect to body 18.

FIGS. 11A, 11B and 12A to 12C illustrate an alternative example embodiment of an electrode subassembly 20b. It should be understood that any of the features of electrode subassembly 20a may also be combined with any of the features of electrode subassembly 20b, and vice versa.

In the illustrated embodiment, electrode subassembly 20b includes an electrode 16, a sleeve 70, at least one shaft 72, a locking element 74, a cap 76 and a biasing element 78. Sleeve 74 may be placed into aperture 28 to attach electrode subassembly 20b to body 18 as explained above with respect to sleeve 54 of electrode subassembly 20a, for example, by a snap fit, threaded fit, or another suitable attachment mechanism. In an embodiment, shaft 72 may include a first shaft and a second shaft which translate with respect to each other as described above with respect to first shaft 52 and second shaft 72 of electrode subassembly 20a.

In the illustrated embodiment, shaft 72 may be placed through an aperture 80 in sleeve 70, enabling shaft 72 to translate with respect to sleeve 70. Shaft 72 may then move relative sleeve 70 so that electrode 16 may be urged into contact with a user's head via biasing element 78 (deployed configuration) and/or retracted from the patient's head and locked into place via locking element 74 (retracted configuration). In an embodiment, biasing element 78 is a spring that is wound around shaft 72 between electrode 16 and sleeve 70, but those of ordinary skill in the art will recognize from this disclosure other biasing elements that may be used. Electrode subassembly 20b may further include wiring 84, which may place electrode 16 in electronic communication with data transmission device 22 or another electrical element. In an embodiment, the wiring 84 may be located through the center of shaft 72 and/or cap 76. In another embodiment, electrode 17 may be placed into electrical communication with data transmission device 22 via electrical contacts in a similar configuration shown with respect to electrode subassembly 20a above (e.g., elements 30, 60, 64 above).

As illustrated in FIG. 11B, aperture 80 of sleeve 70 includes a keyhole 82 which may be aligned with locking element 74 when electrode subassembly 20b is attached to body 18 of headset 12. In an alternative embodiment, sleeve 70 may be eliminated and aperture 80 including keyhole 82 may be formed directly through body 18, for example, replacing an aperture 28.

Figure 12A:
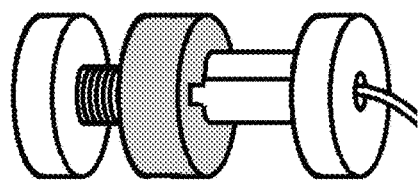
FIGS. 12A to 12C illustrate an example embodiment of the electrode subassembly of FIG. 11 moving from a retracted configuration to a deployed configuration.
Figure 12B:
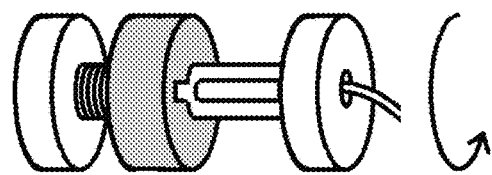
Figure 12C:
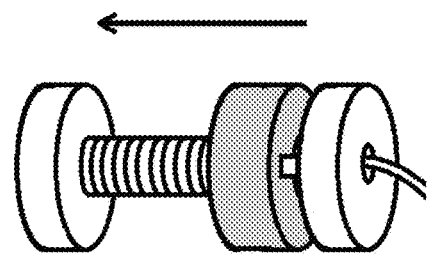

FIGS. 12A to 12C illustrate deployment of electrode subassembly 20b from the retracted configuration to the deployed configuration. In FIG. 12A, electrode subassembly 20b is shown in the retracted configuration, with electrode 16 retracted away from the user's head for fitting and/or storage of headset 12. In the retracted configuration, electrode subassembly 20b is held in place by locking element 74, which is not aligned with keyhole 82 and instead rests outside the perimeter of aperture 80 on sleeve 70, compressing biasing element 78 between electrode 16 and sleeve 70 and/or body 18. In FIG. 12B, electrode subassembly 20b is rotated around the central axis of shaft 72 so that locking element 74 is aligned with keyhole 82. The user may rotate electrode subassembly 20b, for example, by gripping cap 76 with the user's fingers and twisting approximately 90° (or, e.g., 30°, 45°, 180°, etc.). In FIG. 12C, electrode 16 is urged into contact with the user's head by biasing element 78 as the user releases cap 76 and locking element 74 slides into keyhole 82. Electrode 16 may then be held against the user's head by biasing element 78 while the device is in use. In an embodiment, electrode subassembly 20b may further be associated with a position sensor to determine how far electrode 16 is thereafter pushed back by the user's head as described above.

In an embodiment, electrode subassembly 20b may include one or more electrical contact similar to electrode subassembly 20a, enabling electrode subassembly 20b to alternate between an OFF position in which electrode 16 is not in electrical communication with data transmission device 22 and an ON position in which electrode 16 is placed in electrical communication with data transmission device 22. For example, locking element 74 may be or include an electrical contact (e.g., similar to first electrical contact 60 above), and keyhole 82 may be or include a corresponding electrical contact (e.g., similar to second electrical contact 64a above and/or third electrical contact 64b above), such that electrode 16 is placed in electrical communication with data transmission device 22 when locking element 74 slides into keyhole 82. In such an embodiment, electrode subassembly 20b may be in the OFF position when positioned as illustrated in FIG. 12A, and may be in the ON position when positioned as illustrated in FIG. 12C.

In the above illustrated embodiments and other embodiments, each of the electrodes 16 may be placed in electronic communication with data transmission device 22, either through a wired or wireless connection. Data transmission device 22 may include, for example, a Bluetooth adaptor and a circuit board with the capability of receiving an electrical lead (e.g., wiring 24) from each electrode 16 (e.g., eight electrical lead inputs). In an embodiment, data transmission device 22 may further include a control unit having a memory and a processor, enabling data transmission device 22 to process the signal from each electrode 16 into processed data prior to transmitting the processed data to electronic device 14. In another embodiment, data transmission device 22 may transfer raw data to electronic device 14 without any processing. In an alternative embodiment, data transmission device 22 may be excluded, and data from each electrode 16 may be wirelessly transmitted directly to electronic device 14 or another location.

Returning to FIG. 1, when data transmission device 22 receives data from electrodes 16 regarding one or more detected transcranial electrical signals, data transmission device 22 may transmit the received data, either raw or processed, to electronic device 14 for further transformation into useable information for various applications. In the illustrated embodiment, data transmission device 22 transmits the data wirelessly, but a wired connection is also possible. In an embodiment, electronic device 14 may be, for example, a personal electronic device such as cellular phone, tablet, laptop computer, central computer processor, television, video gaming system, or similar device. In an alternative embodiment, electronic device 14 may be part of a larger system, for example, a medical device with the capability of treating a patient for a medical condition. Various embodiments are discussed below.

In an embodiment, data transmission device receives voltage data relating to one or more transcranial electrical signal from each electrode 16. Data transmission device 22 may then transmit the voltage data to electronic device 14, so that electronic device 14 may transform the voltage data into other processed data. Data transmission device 22 may also transform the voltage data into other processed data before transmitting any data to electronic device 14. By performing preprocessing at transmission device 22, the processing power of electronic device 14 may be freed up for other tasks, and the transfer of information may be quicker, enabling real-time analysis of the signals from electrodes 16. Data transmission device 22 may also store raw or processed data in a local memory contained on headset 12, so that the data may be extracted for analysis at a later time.

Figure 13:
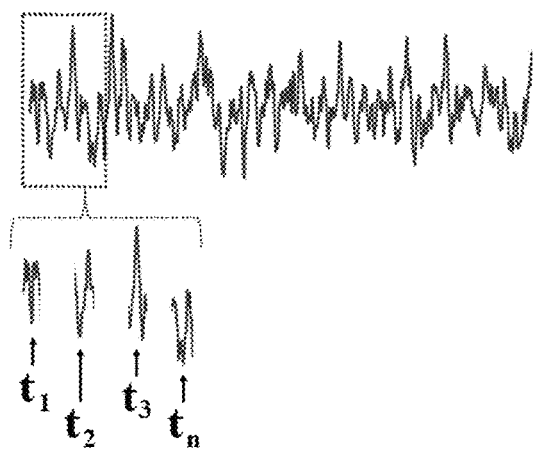
FIG. 13 illustrates an example embodiment of voltage data from an electrode according to the present disclosure.

FIG. 13 illustrates an example embodiment of a signal that may be received by data transmission device 22 from an electrode 16. In the illustrated embodiment, the signal signifies the voltage at the electrode 16 over a period of time. In an embodiment, the control unit of data transmission device 22 and/or electronic device 14 breaks the signal from each electrode 16 into smaller time segments (e.g., $t_1$, $t_2$, $t_3$ ... $t_n$), and then creates a matrix of values (e.g., a matrix of voltage data) using the time segments from one or more electrode 16. The time segments may be divided, for example, on the scale of 0.01 second, 0.1 second, 1 second, or any other suitable value. In an embodiment, the time segments may overlap (e.g., $1^{st}$ time segment is 0 to 0.5 of first second, second time segment is 0.1 to 0.6 of first second, $3^{rd}$ time segment is 0.2 to 0.7 of first second, etc.). In an alternative embodiment, the matrix of values may be created at an electronic device 14 instead of at data transmission device 22. In an embodiment, a single matrix is created with values from some or all of the electrodes 16 for further processing. In an alternative embodiment, a separate matrix is created for each electrode 16.

In the illustrated embodiment, electronic device 14 includes a user interface 50 (e.g., including a display and an input device) and a control unit having a memory 92 and a processor 94 capable of executing instructions stored on memory 92. In use, the control unit of electronic device 14 enables the user to set up headset 12, calibrate headset 12, and use headset 12 for various applications. Each of these steps are discussed in more detail below. It should be understood that any of the methods disclosed herein may be stored as instructions on memory 92, wherein such instructions may be executed by processor 94 such that the control unit controls the method. It should be further understood that the methods/processing functions described herein with respect to processor 94 may be performed by a control unit at data transmission device 22 or a control unit of electronic device 14, or may be split up between either or both control units. Accordingly, "the control unit" as used herein may include any or all control units located at headset 12 or other electronic devices 14 unless specified otherwise.

Setup of Headset

Figure 14:
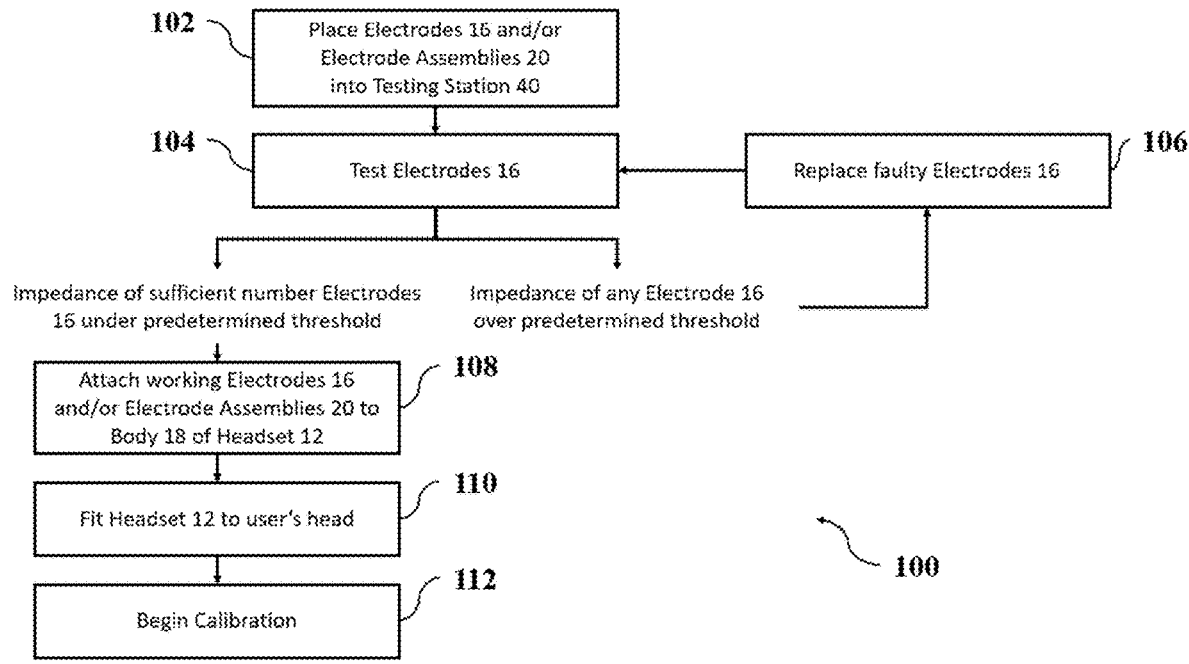
FIG. 14 illustrates an example embodiment of a method of setting up a neural analysis system according to the present disclosure.

FIG. 14 illustrates an example method 100 illustrating how a user may set up headset 12 for use using electrode testing station 40. It should be understood that some of the steps described herein may be reordered or omitted, while other steps may be added, without departing from the spirit and scope of the method of FIG. 14.

At step 102, the user places each electrode 16 or electrode subassembly 20 into an electrode testing station 40 as described herein at FIGS. 6 and 7. In an embodiment, electrode testing station 40 may be mounted to a wall and may already contain each electrode subassembly 20.

At step 104, electrode testing station 40 may test each electrode 16 or electrode subassembly 20 to ensure that each electrode 16 is in suitable condition to receive accurate transcranial electrical signals from the user. In an embodiment, electrode testing station 40 may test each electrode 16 by measuring the impedance of each electrode 16. If the impedance detected at any particular electrode 16 is above a predetermined threshold, the electrode 16 may need to be replaced before the headset may be calibrated and used by the user.

At step 106, the user may discard and/or replace any faulty electrode 16 and retest the new electrode 16 at step 104.

At step 108, if a sufficient number of electrodes 16 or electrode subassemblies 20 are determined by electrode testing station 40 to be suitable for use, the user may attach the electrodes 16 or electrode subassemblies 20 to body 18 of headset 12, for example, as described above. By using electrodes 16 or electrode subassemblies 20 in this manner, the user may avoid having to remove an electrode 16 or electrode subassembly 20 once use of headset 12 has begun.

At step 110, the user may fit the headset 12 to his or her head, so that the user may begin calibration at step 112.

Figure 15:
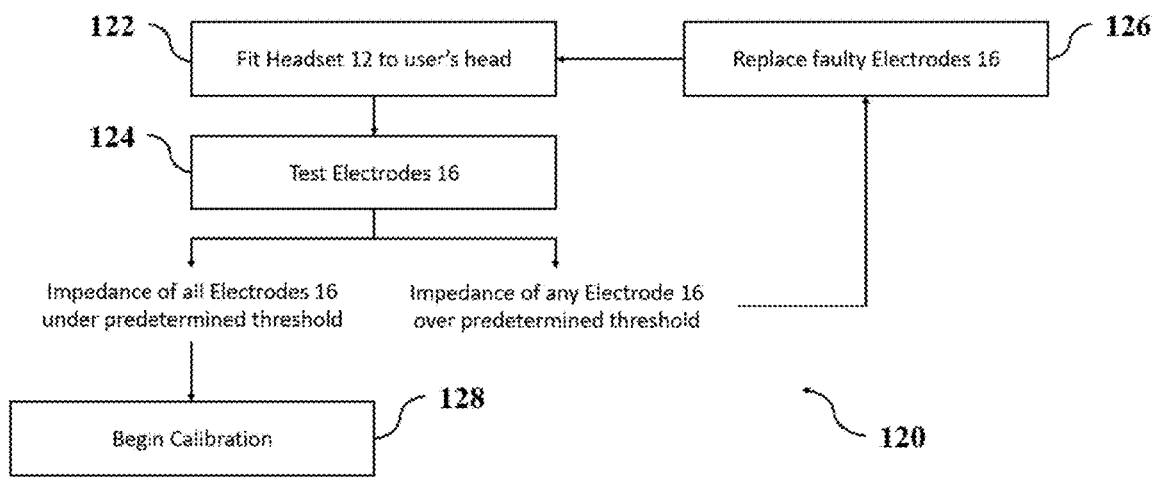
FIG. 15 illustrates an example embodiment of a method of setting up a neural analysis system according to the present disclosure.

FIG. 15 illustrates an alternative example method 120 illustrating how a user may set up headset 12 for use using an electrode subassembly 20 as described herein, or a similar electrode subassembly, without using an electrode testing station 40. It should be understood that some of the steps described herein may be reordered or omitted, while other steps may be added, without departing from the spirit and scope of the method of FIG. 15.

At step 122, the user places headset 12 on the top of his or her head. The user may enable (e.g., deploy and/or turn ON) the electrodes 16 before placing headset 12 on his or her head, or may place the headset 12 on his or her head and then enable the electrodes 16, for example, by twisting or translating each electrode subassembly 20 into an ON position as described herein. The user may also secure headset 12 to his or her head, for example using one or more straps, to avoid movement of headset 12 during use which could cause unwanted artifacts that affect the voltages recorded from electrodes 16.

In an embodiment, electronic device 14 may provide the user with instructions as the user is setting up headset 12. For example, user interface 50 of electronic device 14 may provide the user with a step-by-step diagram showing how to correctly place headset 12 on his or her head, and how to set up each electrode 16. If the plurality of electrodes 16 are adjustable, user interface 50 may also instruct the user to adjust one, some, or all of the plurality of electrodes 16, for example, to move the electrodes 16 closer to the user's head, further from the user's head, or at a different horizontal and/or vertical position on the user's head.

At step 124, the control unit of neural analysis system may cause each electrode 16 to be tested to make sure that each electrode 16 is correctly placed and in suitable condition to receive accurate transcranial electrical signals from the user. In one embodiment, each electrode 16 may be tested by completing the electrical circuit between the electrode 16 and data transmission device 22, for example as shown in FIGS. 10A to 10C above, and determining whether a transcranial electrical signal from electrode 16 may detected at data transmission device 22. In another embodiment, the control unit cause the impedance to be measured at each electrode 16.

If the impedance detected at any particular electrode 16 is above a predetermined threshold, the electrode 16 may need to be replaced before the headset may be calibrated and used by the user. In this case, user interface 50 may instruct the user to remove headset 12 and replace one or more particular electrode 16. User interface 50 may display a diagram showing the user which electrode 16 to replace, or the headset 12 may identify the electrode in need of replacement, for example, using a small light or other identification device (e.g., indicator device 62b) as discussed herein. This feature is advantageous, for example, because the user may simply replace a less costly malfunctioning electrode 16 as opposed to an entire headset 12 if there is a problem with only one electrode 16.

At step 126, the user must replace an electrode, for example, because step 124 indicated that at least one of the electrodes 16 had an impedance that was too high. The user may then replace the electrodes and return to step 122, refit headset 12, and test the electrodes 16 once again.

At step 128, all of the electrodes tested correctly, so the user may move on to calibrating the headset 12 for use in one or more various applications.

Configuring Neural Analysis System for a User

Figure 16:
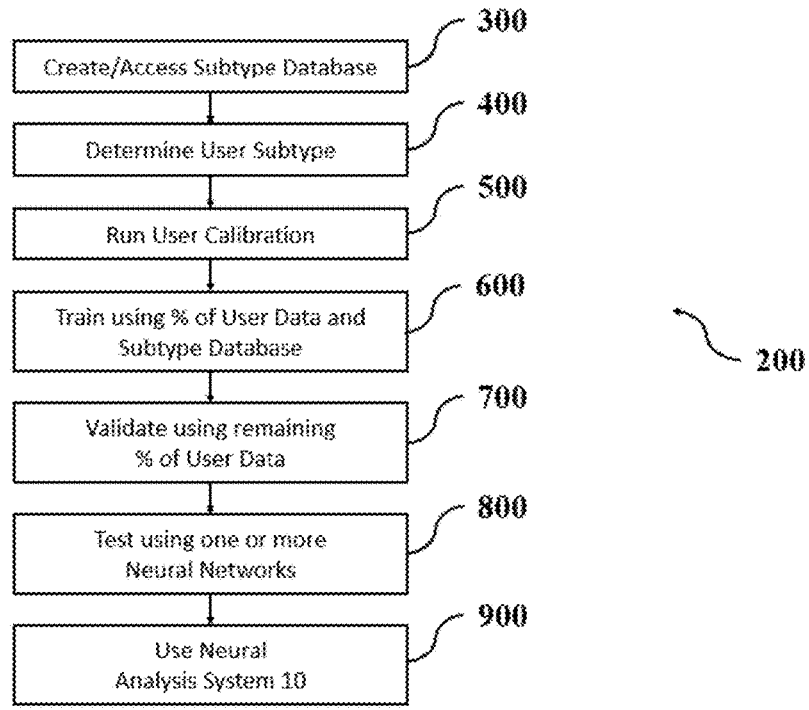
FIG. 16 illustrates an example embodiment of a method of using a neural analysis system according to the present disclosure.

FIG. 16 illustrates an example method 200 illustrating how to configure neural analysis system 10 for a specific user once the headset 12 is functioning properly. Each of the steps of method 200 are discussed in more detail with reference to the figures that follow. It should be understood that some of the steps described herein may be reordered or omitted, while other steps may be added, without departing from the spirit and scope of method 200 of FIG. 16. It should further be understood that one or more of the steps of method 200 may be controlled by the control unit of neural analysis system 10 based on instructions stored on a memory and executed by a processor.

Figure 17:
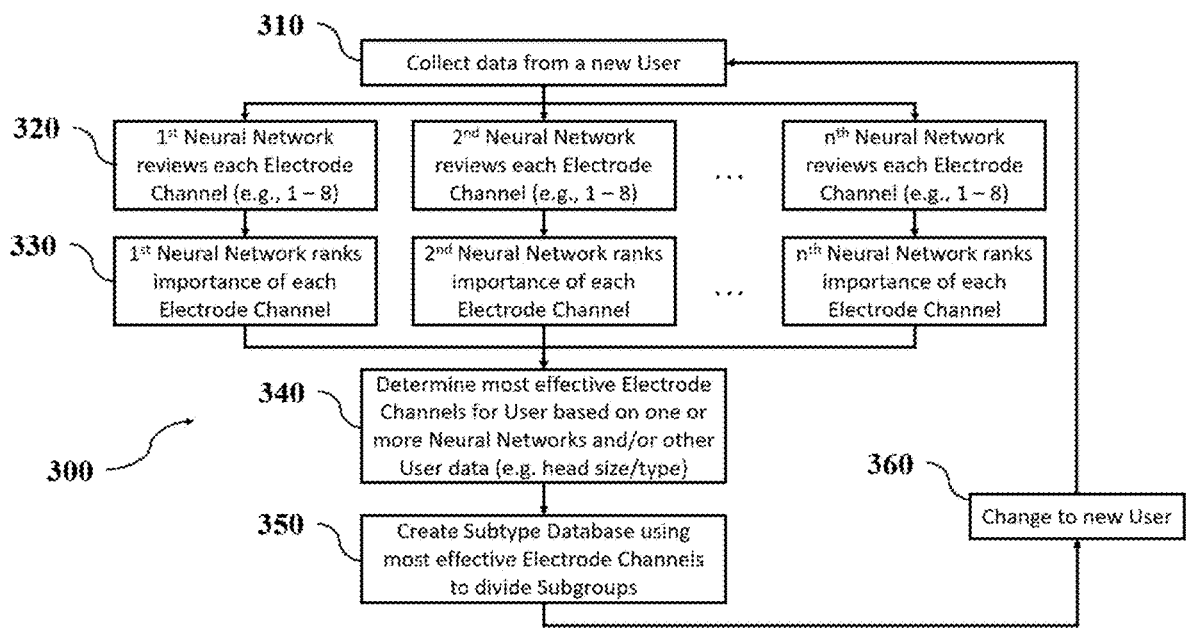
FIG. 17 illustrates an example embodiment of a method of creating a subtype database to be used by a neural analysis system according to the present disclosure.

At step 300, a subtype database is either created or accessed. FIG. 17 illustrates creation of a subtype database in more detail. In the illustrated embodiment, the subtype database may be created a single, initial time. After creation, subsequent data from additional users may be used to supplement the subtype database to improve accuracy and decrease calibration time for subsequent users.

Figure 18:
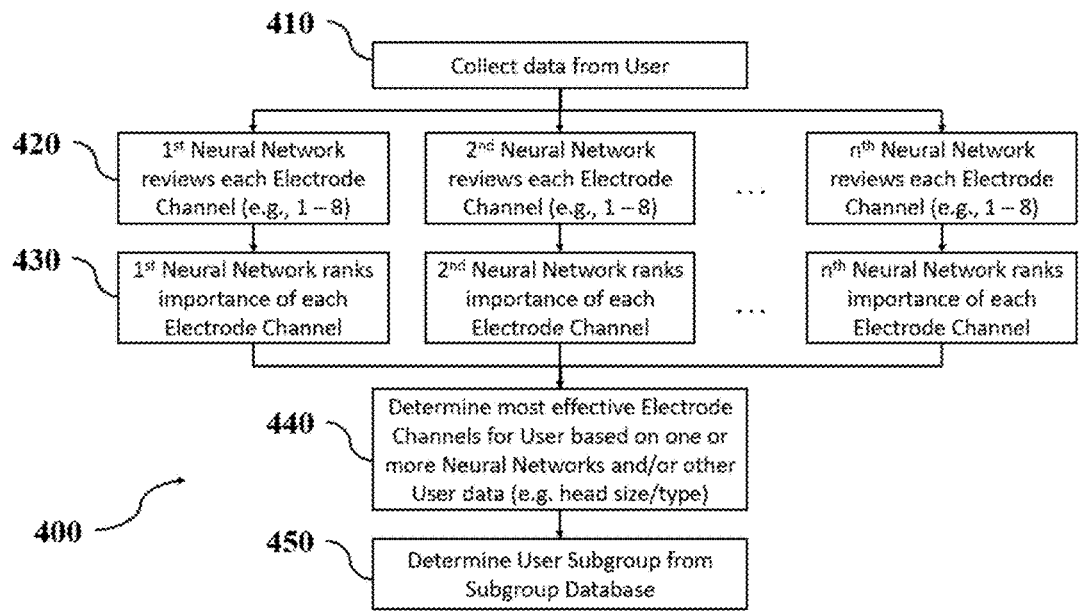
FIG. 18 illustrates an example embodiment of a method of determining a user's subtype for use by a neural analysis system according to the present disclosure.

At step 400, a particular user of headset 12 may determine his or her subtype for use with the subtype database. FIG. 18 illustrates determination of the user's subtype in more detail. In the illustrated embodiment, the user's subtype may be determined, for example, based on the most effective electrode channels for that user, and/or the shape and/or size of the user's head.

At step 500, the particular user of headset 12 may run a calibration, for example, using an electronic device 14. FIGS. 19A to 26B illustrate example embodiments of a user's calibration in more detail. In an embodiment, the user may run the calibration using his or her electronic device 14. In another embodiment, a third party such as a therapist may run the calibration using his or her electronic device 14. In another embodiment, the calibration may be based on a combination of a user's inputs and a third party's inputs. In another embodiment, steps 400 and 500 may be combined or performed simultaneously, and/or data from the user's calibration at step 500 may be used to perform step 400.

Figure 27:
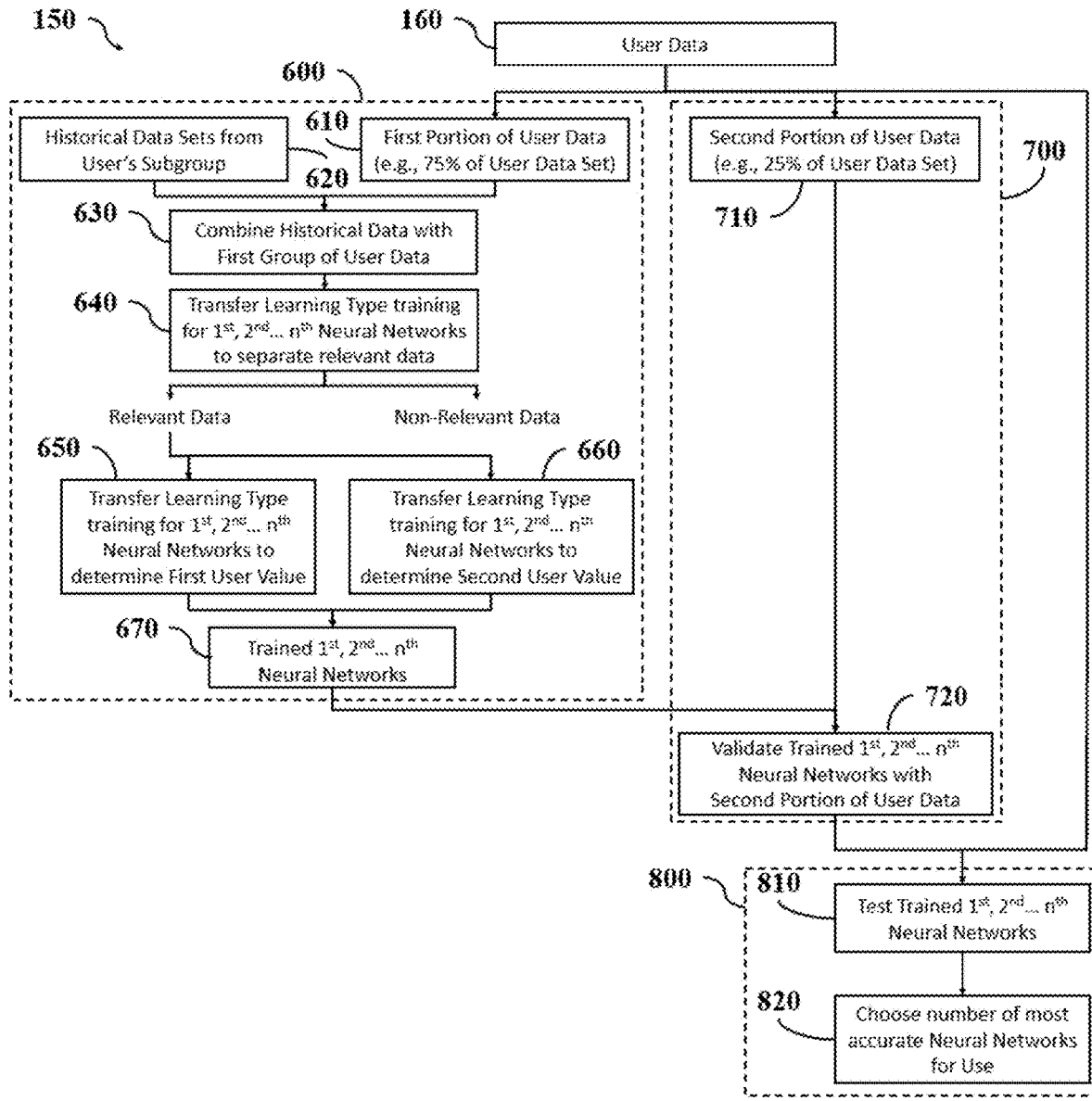
FIG. 27 illustrates an example embodiment of a method of training, validating and testing a neural analysis system according to the present disclosure.
Figure 28:
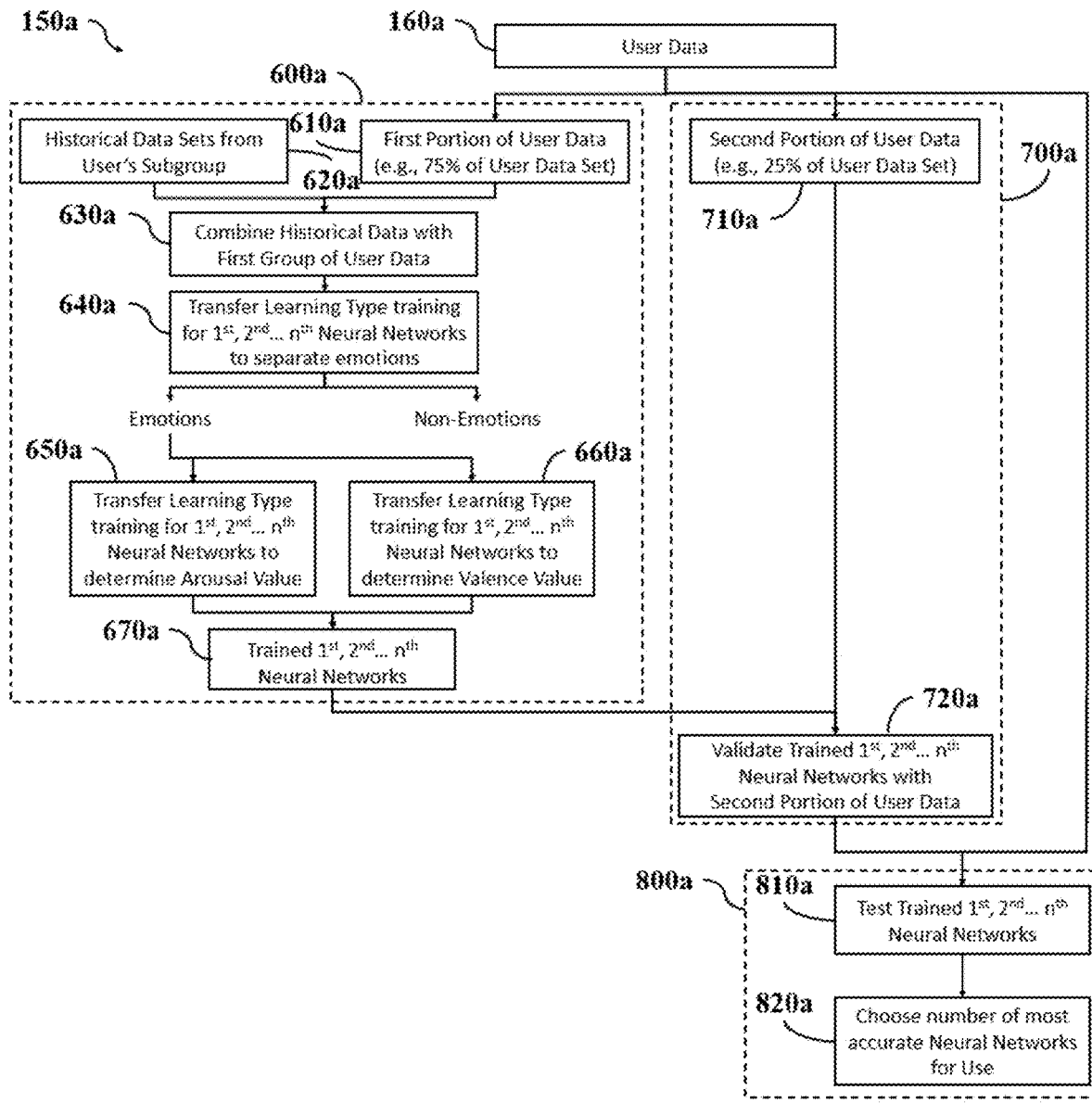
FIG. 28 illustrates an example embodiment of the method of FIG. 27.
Figure 29:
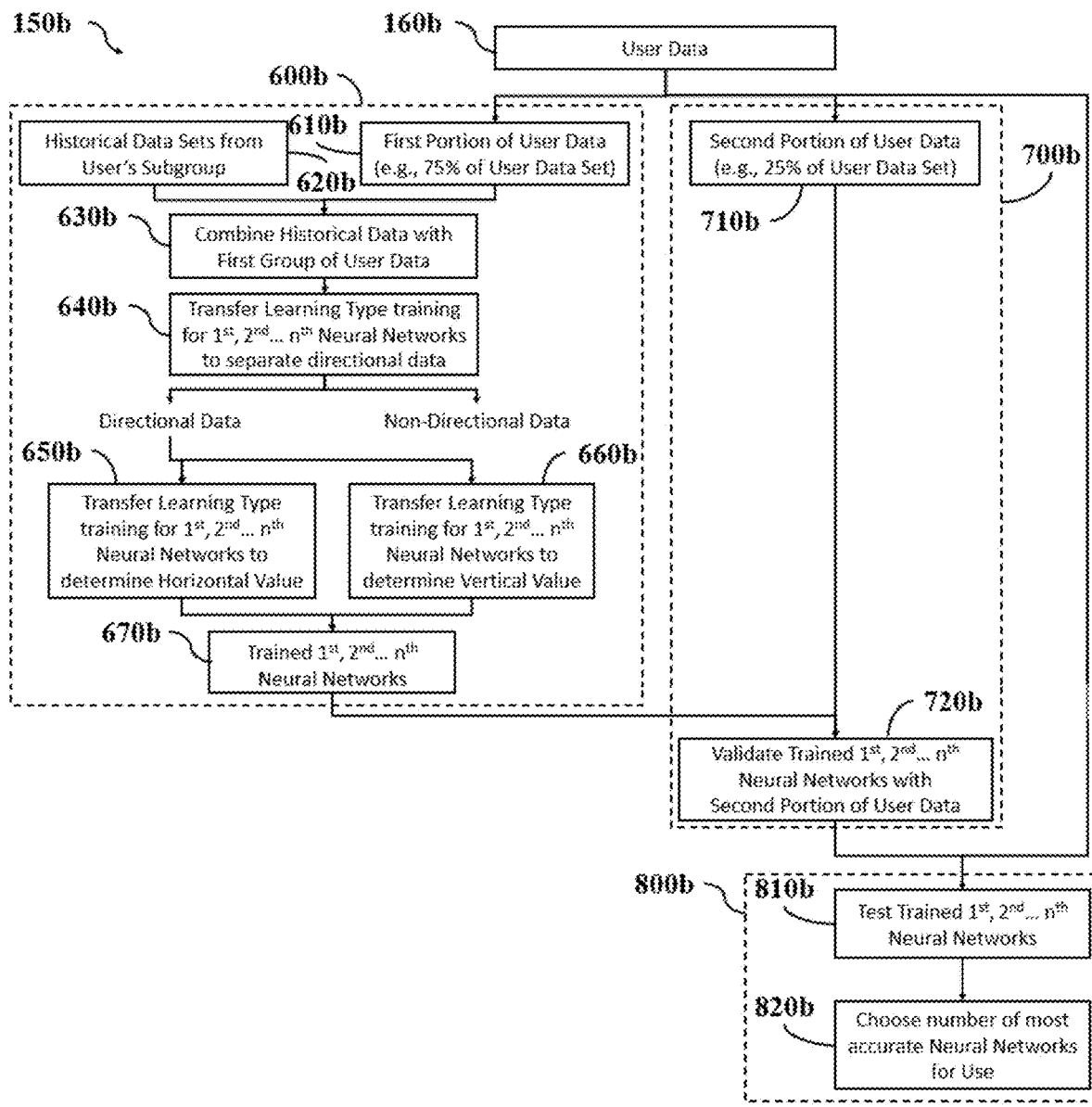
FIG. 29 illustrates an example embodiment of the method of FIG. 27.

At step 600, the control unit of neural analysis system 10 is trained using a portion of the data from the user's calibration along with additional calibration data from the subtype database. FIGS. 27 to 29 illustrate example embodiments of training method 600 in more detail.

At step 700, the control unit of neural analysis system 10 validates the training session of step 600 by evaluating the results using a previously unused portion of the data from the user's calibration. FIGS. 27 to 29 illustrate example embodiments of validation method 700 in more detail.

At step 800, the control unit of neural analysis system 10 tests itself using some or all of the data from the user's calibration. During testing, the control unit may select one or more neural networks to use for various applications. FIGS. 27 to 29 illustrate example embodiments of testing method 800 in more detail.

At step 900, the control unit of neural analysis system 10 has been trained, validated and/or tested, and is ready for use in various applications.

Creation of Subtype Database

FIG. 17 illustrates an example method 300 illustrating how a subtype database may be created or enhanced. It should be understood that some of the steps described herein may be reordered or omitted, while other steps may be added, without departing from the spirit and scope of method 300 of FIG. 17. It should further be understood that one or more of the steps of method 300 may be controlled the control unit of neural analysis system 10 based on instructions stored on a memory and executed by a processor.

At step 310, data is collected from a new user wearing a headset 10. The collected data may include, for example, one or more matrices of voltage or other data collected using the electrodes 16 of headset 12. The collected data may also include the size and/or shape of the user's head, as determined by sensors (e.g., the position sensors associated with each electrode subassembly 20 as discussed herein) indicating how far each electrode 16 translates when the user places the headset 12 on his or her head. In an embodiment, the collected data may include calibration data collected from the user using the calibration method 500 illustrated herein at FIG. 19A and discussed in more detail below, thereby providing one or more data matrices associated with user values for the subtype database.

At step 320, the collected data regarding each of the electrodes is input into one or more neural network to determine which of the electrode channels is most effective for the user. In an embodiment, the effectiveness is determined by at least one of: (i) a strength of signal for each electrode channel; and an impedance across each electrode channel. The one or more neural networks may be, for example, convolutional neural networks, recurrent neural networks, or a combination of convolutional and recurrent neural networks.

At step 330, each neural network ranks one or more of the electrode channels based on effectiveness. In an embodiment, the neural network may rank only the most effective one or more of the electrode channels. In another embodiment, the neural network may rank all of the electrode channels based on effectiveness.

At step 340, the results of all of the neural networks are evaluated or combined (e.g., averaged), and the most effective electrode channels are determined for the particular user tested. In an embodiment, the top few (e.g., 2, 3, 4, etc.) electrode channels may be chosen as being the most effective for the user. For example, it may be determined that Electrode Channel #3 is the most effective, Electrode Channel #6 is the second most effective, and Electrode Channel #2 is the third most effective for a particular user.

Optionally, the user's head size and/or head type may also be used at one or more of steps 320, 330 and 340 to determine a correlation between head size and effective electrode channels.

At step 350, the effectiveness of the electrode channels is used to classify the user into a subtype, and some or all of the signal data and/or matrices and/or user data recorded from that user is stored in that subtype database. Additionally, the user's head size and/or type may also be stored in that subtype database.

At step 360, method 300 is repeated with a different user. As additional users add to the database, accuracy for every subsequent user is improved, as calibration, training, validating and testing time for every subsequent user may be decreased.

In an embodiment, generative adversarial networks for data augmentation may also be used to enhance training with the subtype database, for example, by providing artificial but naturalistic datasets to add to those accumulated from users.

Determination of User Subtype

FIG. 18 illustrates an example method 400 illustrating how a current user's subtype may be determined for use with the subtype database, so that the user may use neural analysis system 10 for various applications. It should be understood that some of the steps described herein may be reordered or omitted, while other steps may be added, without departing from the spirit and scope of method 400 of FIG. 18. It should further be understood that one or more of the steps of method 400 may be controlled by the control unit of neural analysis system 10 based on instructions stored on a memory and executed by a processor.

At step 410, data is collected from the current user wearing a headset 10. The collected data may include, for example, one or more matrices of voltage or other data collected from each of the electrodes 16 of headset 12. The collected data may also include the shape and/or type of the user's head, for example, using position sensors associated with electrode subassembly 20 as discussed herein.

At step 420, the collected data regarding each of the electrodes 16 is input into one or more neural network to determine which of the electrode channels is most effective for the user.

At step 430, each neural network ranks one or more of the electrode channels based on effectiveness. In an embodiment, the neural network may rank only the most effective of the electrode channels. In another embodiment, the neural network may rank all of the electrode channels based on effectiveness.

At step 440, the results of all of the neural networks are evaluated or compared (e.g., averaged), and the most effective electrode channels are determined for the particular user tested. In an embodiment, the top few (e.g., 2, 3, 4, etc.) electrode channels may be chosen.

Optionally, the user's head size and/or type may also be used at one or more of steps 420, 430 and 440 to determine a correlation between head size and/or shape and effective electrode channels.

At step 450, the effectiveness of the electrode channels is used to classify the user into a subgroup within the subgroup database. Additionally, the user's own data may be added to the subgroup database to improve the subgroup database. As additional users add to the subtype database, accuracy for every subsequent user during use of neural analysis system 10 is improved.

Calibration of Headset for a Current User

Figure 19A:
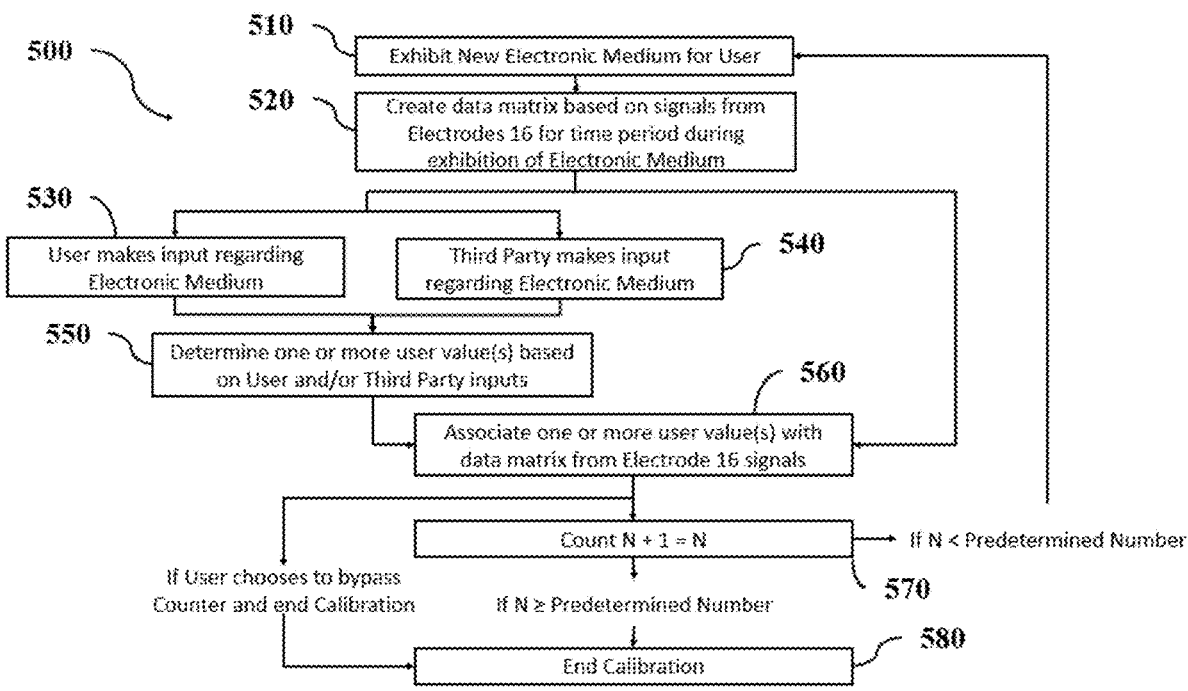
FIG. 19A illustrates an example embodiment of a method of calibrating, for a particular user, a neural analysis system according to the present disclosure.

FIG. 19A illustrates an example method 500 illustrating how a current user may calibrate headset 12 for use in various applications. It should be understood that some of the steps described herein may be reordered or omitted, while other steps may be added, without departing from the spirit and scope of method 500 of FIG. 19A. It should further be understood that one or more of the steps of method 500 may be controlled by the control unit of neural analysis system 10 based on instructions stored on a memory and executed by a processor.

At step 510, electronic device 14 exhibits a first electronic medium 90 for the user wearing headset 12. The first electronic medium 90 may include, for example, an image or video that is displayed by electronic device 14, one or more sounds played by electronic device 14, or other electronic media. In an alternative embodiment, the user may be shown a medium (e.g., image, photograph, song) by a third party instead of viewing/listening using electronic device 14.

At step 520, the control unit of neural analysis system 10 creates one or more data matrix based on the signals received from the plurality of electrodes 16. In the illustrated embodiment, the signal from each electrode 16 signifies the voltage at the electrode over a period of time. In an embodiment, the control unit of neural analysis system breaks the signal from each electrode 16 into smaller time segments (e.g., $t_1, t_2, t_3 \ldots t_n$), and then creates a matrix of values (e.g., a matrix of voltage data) using the time segments from one or more electrode 16. In an embodiment, the control unit creates a single matrix with values from some or all of the electrodes 16 for further processing. In an alternative embodiment, a separate matrix is formed for each electrode 16.

At step 530, the user makes an input regarding the first electronic medium 90, which input may then be stored as one or more user values. In an embodiment, the user may be presented with a plurality of selections to choose from on user interface 50 of electronic device 14. The input may define one or more user output state (e.g., an emotional state felt by the user, a desired directional outcome on the display, a musical note or image seen or heard by the user, etc.). In an alternative embodiment, the user may define one or more user values by inputting the one or more user values into user interface 50 of electronic device 14.

At step 540, a third party may make an input regarding the first electronic medium 90, which input may then be stored as one or more user values. In an embodiment, the third party may be presented with a plurality of preset selections to choose from. The input may define one or more user output state. In an alternative embodiment, the third party may define one or more user values by inputting the one or more user values into an electronic device 14.

In an embodiment, both the user of headset 12 and the third party may make an independent input regarding the first electronic medium 90, and both of these inputs may be used subsequently to gain a more accurate reading with a more robust set of data. The user and the third party may make their inputs on the same electronic device 14 or on different electronic devices 14.

Figure 19B:
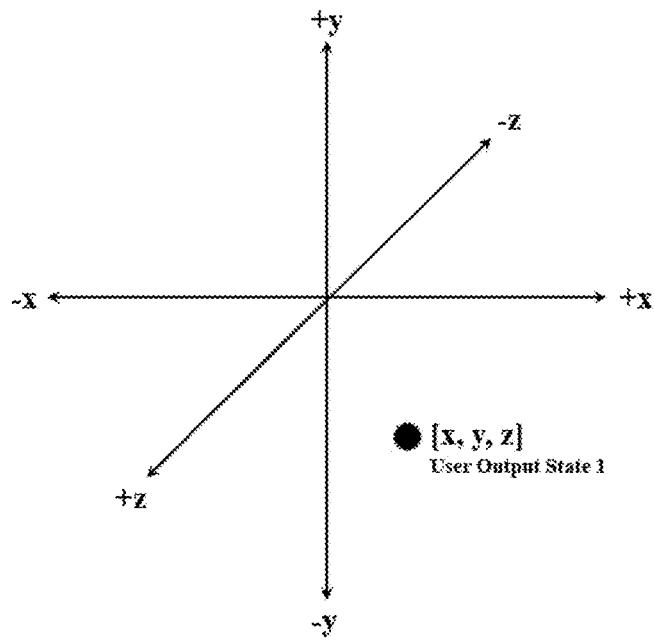
FIG. 19B illustrates an example embodiment of a plot showing how user values can yield one or more user output states for use in the method according to the present disclosure.

At step 550, one or more user values may be determined by the input from the user and/or third party, wherein the one or more user values are associated with one or more user output state based on the input. In an embodiment, the one or more user values may be determined by the input by the user by associating the input with numerical values, for example, using a plot as shown in FIG. 19B or a similar computation. In another embodiment, the one or more user values may be input directly by the user or third party. The input user values may include one or more numerical values, for example, a first user value, a second user value, a third user value, etc.

As illustrated by FIG. 19B, the one or more user values may be defined on a one-dimensional or multidimensional plot. Here, a three dimensional plot is shown, but those of ordinary skill in the art will recognize from this disclosure that one-dimensional, two-dimensional, and other multidimensional plots may be used. The inputted one or more user values may include, for example, a first user value (e.g., an x value), a second user value (e.g., a y value), and a third user value (e.g., a z value). The inputted one or more user values are then associated with one or more user output state. It should be understood form this disclosure that the plot in FIG. 19B is an example for visualization purposes, and the methods herein may be performed by the control unit of neural analysis system without drawing a physical plot.

At step 560, the data matrix or matrices from step 520 is associated with the determined one or more user values and/or user output state, and the combination is stored for training, validation and/or testing as described in more detail below.

At step 570, the control unit of neural analysis system 10 adds to a counter. For example, counter may start at zero (0) and add one (1) to the counter each time step 570 occurs. Method 500 then returns to step 510 and proceeds through steps 510, 520, 530/540, 550 and 560 with a second electronic medium 90. The next time the method reaches step 570, another one (1) may be added to the previously counted one (1), making N=2. The process may then continue with a third electronic medium 90, fourth electronic medium 90, etc. until N is reached.

As steps 510, 520, 530, 540, 550, 560 and/or 570 are repeated, neural analysis system 10 builds a database with a plurality of user output states (e.g., user output state 1, user output state 2, user output state 3, etc.), wherein each of the user output states is associated with one or more user values. For example, using the example three-dimensional plot of FIG. 19B, a first user output state can have a first user value (e.g., 1), a second user value (e.g., -1) and a third user value (e.g., 2), a second user output state can have a first user value (e.g., -3), a second user value (e.g., 4) and a third user value (e.g., 0), a third user output state can have a first user value (e.g., 3), a second user value (e.g., 1) and a third user value (e.g., -2), etc. As more user output states and corresponding user values are determined during the calibration process, neural analysis device 10 becomes more accurate in interpreting the user's transcranial electrical signals. As the user views and/or listens to more electronic mediums, use of neural analysis system 10 after calibration becomes more tuned to the user's particular transcranial electrical signals.

When the counter reaches number N, user calibration is complete at step 580, and neural analysis system 10 may move on to training, validation and/or testing. Number N may be preset, or may be chosen by the user and/or third party, before or at the beginning of calibration, depending for example on the amount of time the user and/or third party wishes to spend calibrating the device. The higher number N is, the more accurate the user's calibration is expected to be. In an embodiment, the user may bypass step 570 and end calibration at any time the user wishes, or the user at step 560 may be given the option of viewing/listening to another electronic medium or ending calibration.

In an embodiment, the control unit of neural analysis system 10 may save the calibration data for a particular user or multiple users. The user may then recall the saved calibration data during a later session and use the saved calibration data to: (i) skip a current calibration procedure; (ii) abbreviate a current calibration procedure; and/or (iii) enhance a current calibration procedure. In an embodiment, the data from calibration may also be added to the subtype database to improve the subtype database for future use.

In an embodiment, the user may skip a current calibration procedure and use the previously saved calibration data matrices to use headset 12. This may, however, cause the determinations by neural analysis system 10 to be less accurate than if a current calibration is performed, for example, because the user may have a different physical or emotional state in comparison with his or her physical or emotional states when the saved calibration was performed, or because the headset may be positioned slightly differently from when the saved calibration was performed.

In an embodiment, each of the users whose data is used to determine the subtype database of FIG. 17 has also gone through the process of FIG. 19A or a similar process, so that the subtype database includes data matrices associated with one or more user values for each subtype. In an embodiment, method 500 shown in FIG. 19A is performed at step 310 of method 300 discussed above to create the initial subtype database. In another embodiment, method 500 shown in FIG. 19A is performed by each user of method 300 after each user has been classified into a subtype.

Several example embodiments of method 500 are discussed below (e.g., method 500a related to emotional states and method 500b related to directional positions). It will be understood by those of ordinary skill in the art from this disclosure, however, that method 500 is not limited to these examples and is useful in a wide variety of applications.

It should be understood from this disclosure that the electronic media 90 do not need to be provided by the same electronic device 14 on which the input is made, as long as a matrix of data is recorded from the electrodes 16 of headset 12 and coordinated with the corresponding one or more user output state. It should further be understood that calibration may be performed on any type of one or more electronic device 14 having a display/user interface 50. The electronic media 90 also do not need to be preprogrammed into electronic device 14. In an embodiment, the user is enabled to provide/view images, videos or sounds that the user knows will evoke a particular emotional state in himself or herself.

In an embodiment, the user may abbreviate or enhance a current calibration procedure, for example, by using some or all of the data matrices from a saved calibration procedure. For example, if the user has twenty (20) data matrices from a saved calibration procedure, and ten (10) data matrices from a current calibration procedure, the user may begin use of neural analysis system 10 with a total of thirty (30) data matrices of user data to use for various applications.

In an embodiment, neural analysis system 10 may adjust for the user having different physical or emotional states or the headset being positioned differently during a saved or current calibration procedure by scaling the saved data to more closely match the current data, or vice versa. For example, if the user experienced higher peaks and valleys in the data during a past session, the saved data could be scaled back to more closely match the user's current state. Likewise, if the user experienced lower peaks and valleys in the data during a past session, the saved data could be scaled up to more closely match the user's current state.

In another embodiment, saved calibration data is always scaled down in comparison with current data, assuming that the user's past states will rarely or never precisely match the user's current state, thus meaning that the current state should be weighed more heavily.

In an embodiment, neural analysis system 10 may adjust for the user having different states during a saved or current calibration procedure by applying weights to the saved or current calibration data. For example, if the user experienced higher peaks and valleys in the data during a past session, the saved data could be multiplied by fractional weights to decrease the significance of past data in comparison with current data. Likewise, if the user experienced lower peaks and valleys in the data during a past session, the saved data could be multiplied by weights above one (1) to increase the value of past numbers. In another embodiment, weights could be added or subtracted from values in past or current data matrices.

In another embodiment, saved calibration data is always be multiplied by fractional weights to decrease the significance of past data in comparison with current data, assuming that the user's past states will rarely or never precisely match the user's current state, thus meaning that the current state should be weighed more heavily.

First Example Embodiment of Calibration of Headset for a Current User (Emotion Embodiment)

Figure 20A:
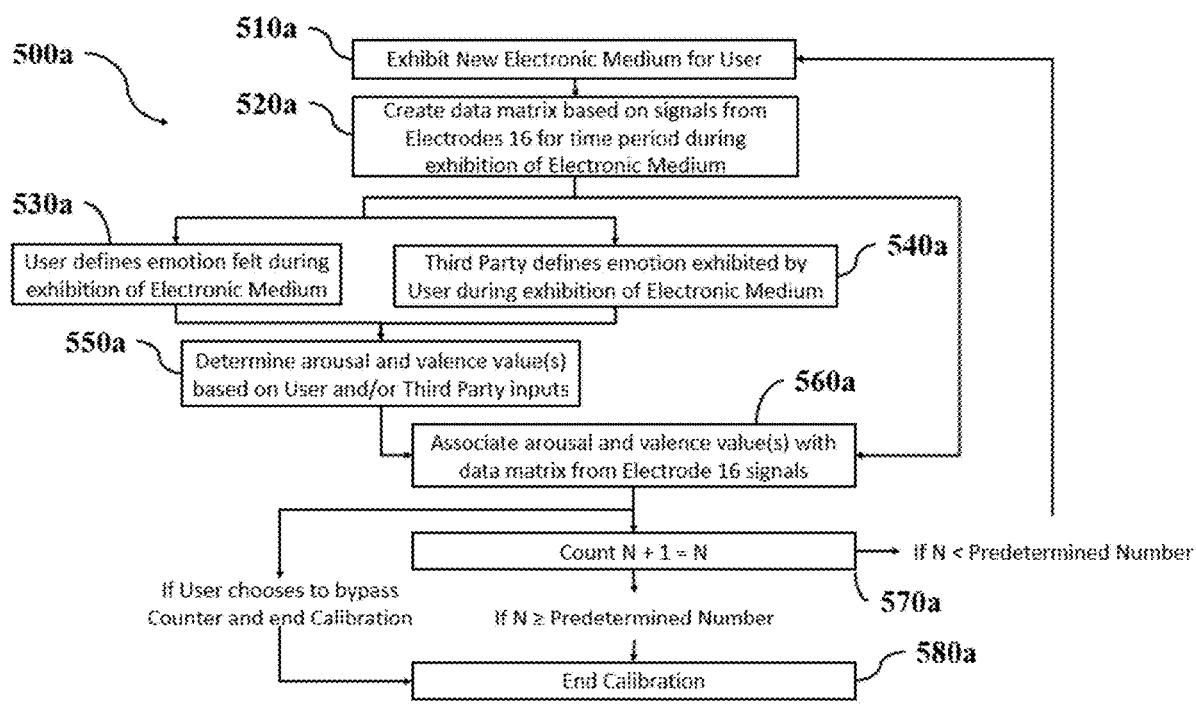
FIG. 20A illustrates an example embodiment of the method of FIG. 19A.

FIG. 20A illustrates an example method 500a illustrating how a current user may calibrate headset 12 for use in determining one or more emotional state of a user. It should be understood that some of the steps described herein may be reordered or omitted, while other steps may be added, without departing from the spirit and scope of method 500a of FIG. 20A. It should further be understood that one or more of the steps of method 500a may be controlled by the control unit of neural analysis system 10 based on instructions stored on a memory and executed by a processor.

In this example embodiment, the one or more user values are emotional values, and the one or more user output state is an emotional state. The emotional values can include, for example, one or more valence value, one or more arousal value, and one or more dominance value. For example, a first user value can be a valence value, a second user value can be an arousal value, and a third user value can be a dominance value. The emotional state can include, for example, an emotion felt by the user (e.g., joy, anger, etc.).

The following example embodiments described for emotional states use valence and arousal as first and second user values. This is for simplicity of explanation. It should be understood from this disclosure that different or additional values or terms can be used without departing from the spirit and scope of this disclosure. For example, as explained above, a useful third user value can relate to dominance. While arousal and valence can explain the majority of emotional variance, a third dimension of dominance can also provide critical information. Dominance ranges from a helpless or weak feeling, which indicates minimal cognitive control, to an empowered feeling, which indicates high cognitive control.

At step 510a, electronic device 14 exhibits a first electronic medium 90 for the user wearing headset 12. The first electronic medium 90 may include, for example, an image or video that is displayed by electronic device 14, one or more sounds played by electronic device 14, or other electronic media. In an alternative embodiment, the user may be shown a medium (e.g., image, photograph, song) by a third party instead of viewing/listening using electronic device 14.

At step 520a, the control unit of neural analysis system 10 creates one or more data matrix based on the signals received from the plurality of electrodes 16. In the illustrated embodiment, the signal from each electrode 16 signifies the voltage at the electrode over a period of time. In an embodiment, the control unit of neural analysis system 10 breaks the signal from each electrode 16 into smaller time segments (e.g., $t_1, t_2, t_3 \ldots t_n$), and then creates a matrix of values (e.g., a matrix of voltage data) using the time segments from one or more electrode 16. In an embodiment, the control unit creates a single matrix with values from some or all of the electrodes 16 for further processing. In an alternative embodiment, a separate matrix is formed for each electrode 16.

At step 530a, the user inputs what he or she believes to be the emotional state felt when viewing and/or listening to the first electronic medium 90. In an embodiment, the user may be presented with a plurality of preset emotional states to choose from on user interface 50 of electronic device 14. In an alternative embodiment, the user may define the emotional state believed to be felt by inputting the emotional state into user interface 50 of electronic device 14. In another alterative embodiment, the user may indicate a level of emotion, or may indicate multiple emotional states or levels of multiple emotions. In another alternative embodiment, the user may indicate the levels of arousal and valence believed to be felt.

At step 540a, a third party such as a therapist may input what he or she believes to be the emotional state felt by the user when the user viewed and/or listened to the first electronic medium 90. In an embodiment, the third party may be presented with a plurality of preset emotional states to choose from. In an alternative embodiment, the third party may define the emotional state believed to be felt by inputting the emotional state into an electronic device 14. In another alterative embodiment, the third party may indicate a level of emotion, or may indicate multiple emotional states or levels of multiple emotions. In another alternative embodiment, the third party may indicate the levels of arousal and valence believed to be felt by the user In an embodiment, both the user of headset 12 and the third party may make an independent determination of what is believed to be the user's emotion, and both of these inputs may be used subsequently to gain a more accurate reading with a more robust set of data. The user and the third party may make their inputs on the same electronic device 14 or on different electronic devices 14.

Figure 20B:
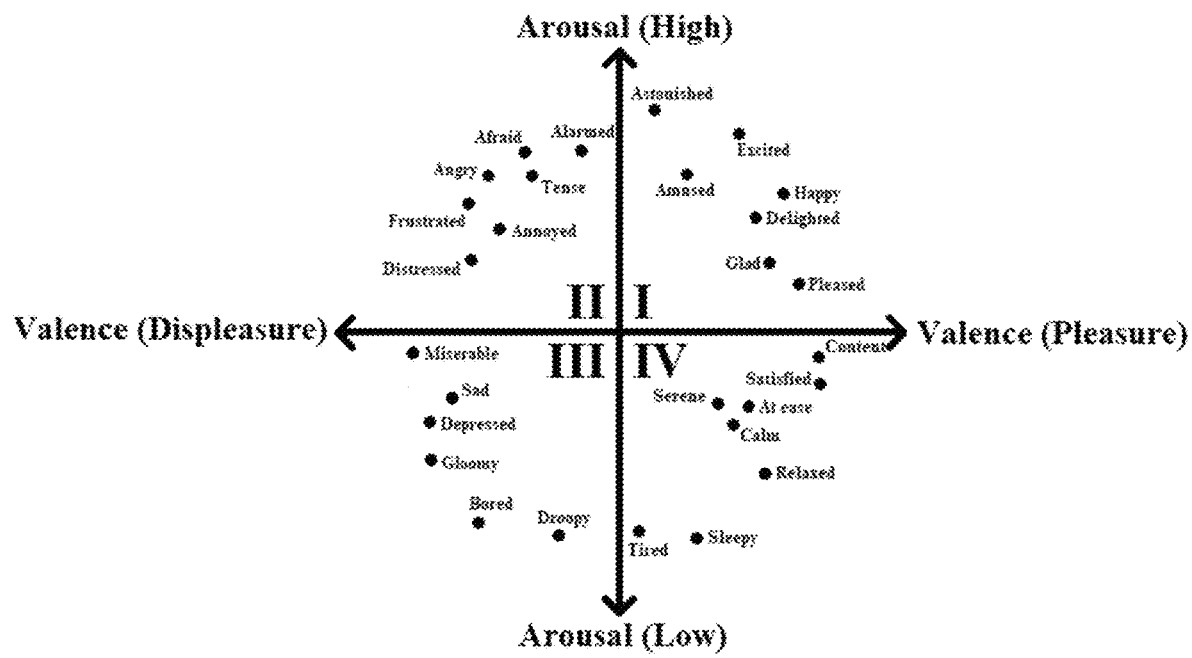
FIG. 20B illustrates an example embodiment of the plot of FIG. 19B to be used with the method of FIG. 20A.
Figures 21A, 21B, 21C:
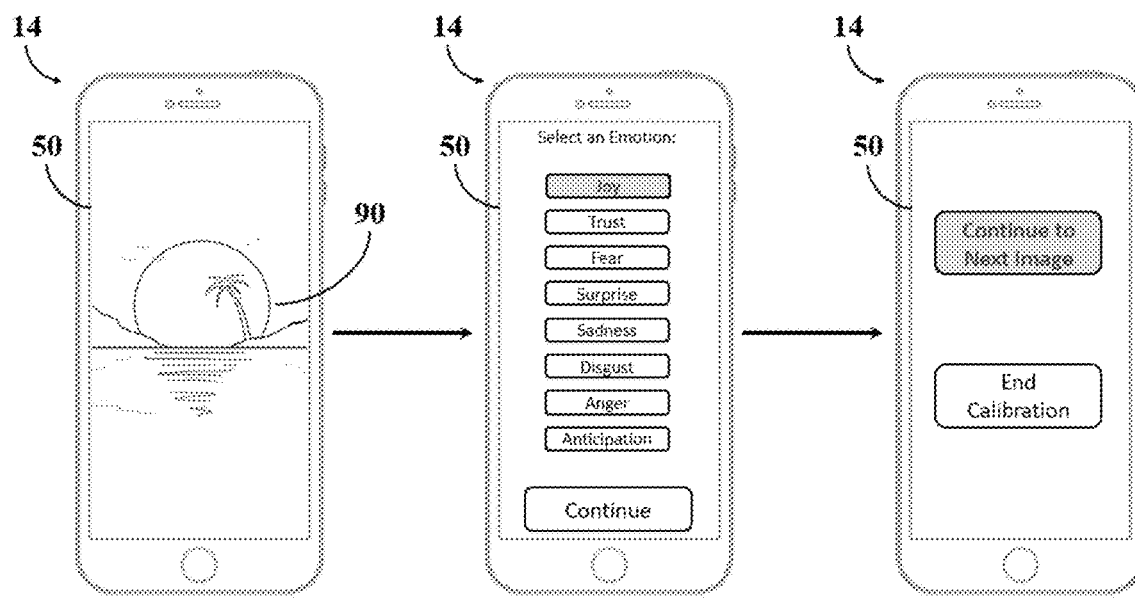

At step 550a, arousal and valence values may be determined by the emotional state or emotional states input by the user and/or third party. In an embodiment, the arousal and valence values may be determined by the emotional state or emotional states input by the user by associating the input with numerical values, for example, using a plot as shown in FIG. 20B or a similar computation. In another embodiment, the arousal and valence values may be input directly by the user or third party.

As illustrated by FIG. 20B, emotional states may be defined on a two-dimensional plot of valence and arousal. As illustrated, a low or negative value for valence may indicate displeasure, a high or positive value for valence may indicate pleasure, a low or negative value for arousal may indicate low arousal, and a high or positive value for arousal may indicate high arousal.

In another embodiment, emotional states may be defined on a three-dimensional plot of valence, arousal, and dominance. For example, the three dimensional plot shown in FIG. 19B may be used with the x value indicating valence, the y value indicating arousal, and the z value indicating dominance. For simplicity, the rest of this example is explained with reference to a two-dimensional plot using arousal and valence, but those of ordinary skill in the art will recognize from this disclosure that a three-dimensional or other multi-dimensional plot may also be used.

In the present example, arousal and valence values may be attributed to various emotional states based, for example, on the plot of FIG. 20B. For example, Quadrant I in FIG. 20B may extend from 0 to 9 on the x-axis (valence) and 0 to 9 on the y-axis (arousal), Quadrant II may extend from −9 to 0 on the x-axis (valence) and 0 to 9 on the y-axis (arousal), Quadrant III may extend from −9 to 0 on the x-axis (valence) and −9 to 0 on the y-axis (arousal), and Quadrant IV may extend from 0 to 9 on the x-axis (valence) and −9 to 0 on the y-axis (arousal). In this way, numerical values may be attributed to arousal and valence based on a selected emotional state (e.g., "Pleased" at about x=2, y=7; "Sleepy" at about x=3, y=−7). It should be understood by those of ordinary skill in the art from this disclosure that other values and/or scales may be used to define arousal and valence.

At step 560a, the data matrix or matrices from step 520a is associated with the determined arousal and valence values, and the combination is stored for training, validation and/or testing as described in more detail below.

At step 570a, the control unit of neural analysis system 10 adds to a counter. For example, counter may start at zero (0) and add one (1) to the counter each time step 570 occurs. Method 500a then returns to step 510a and proceeds through steps 510a, 520a, 530a/540a, 550a and 560a with a second electronic medium 90. The next time the method reaches step 570a, another one (1) may be added to the previously counted one (1), making N=2. The process may then continue with a third electronic medium 90, fourth electronic medium 90, etc. until N is reached.

When the counter reaches number N, user calibration is complete at step 580a, and neural analysis system 10 may move on to training, validation and/or testing. Number N may be preset, or may be chosen by the user and/or third party, before or at the beginning of calibration, depending for example on the amount of time the user and/or third party wishes to spend calibrating the device. The higher number N is, the more accurate the user's calibration is expected to be. In an embodiment, the user may bypass step 570a and end calibration at any time the user wishes, or the user at step 560a may be given the option of viewing/listening to another electronic medium or ending calibration.

In an embodiment, the control unit of neural analysis system 10 may save the calibration data for a particular user or multiple users. The user may then recall the saved calibration data during a later session and use the saved calibration data to: (i) skip a current calibration procedure; (ii) abbreviate a current calibration procedure; and/or (iii) enhance a current calibration procedure. In an embodiment, the data from calibration may also be added to the subtype database to improve the subtype database for future use.

In an embodiment, the user may skip a current calibration procedure and use the previously saved calibration data matrices to use headset 12. This may, however, cause the determinations by neural analysis system 10 to be less accurate than if a current calibration is performed, for example, because the user may have elevated or depressed emotional states in comparison with his or her emotional states when the saved calibration was performed.

In an embodiment, each of the users whose data is used to determine the subtype database of FIG. 17 has also gone through the process of FIG. 20A or a similar process, so that the subtype database includes data matrices associated with arousal and valence values for each subtype. In an embodiment, method 500a shown in FIG. 20A is performed at step 310 of method 300 discussed above to create the initial subtype database. In another embodiment, method 500a shown in FIG. 20A is performed by each user of method 300 after each user has been classified into a subtype.

FIGS. 21A to 21F, 22A to 22D, 23A to 23C and 24 show various embodiments of the user interface 50 of electronic device 14 during the above-described calibration process. It should be understood that FIGS. 21A to 21F, 22A to 22D, 23A to 23C and 24 demonstrate examples only, that the calibration method 500a described herein is not limited to these examples, and that modifications may be made to the method of calibration described herein with departing from the spirit and scope of the present disclosure.

FIGS. 21A to 21F illustrate an example embodiment of method 500a. At FIG. 21A, the user interface 50 of electronic device 14 displays a first electronic medium 90 (e.g., an image, video, and/or sound recording) to the user of headset 12 for a period of time, and neural analysis system 10 records data from the transcranial electrical signals detected at electrodes 16 of headset 12 during that period of time and creates a data matrix or matrices as described herein. At FIG. 21B, the user or a third party inputs what he or she believes to be the emotional state felt by the user during viewing of the first electronic medium 90, wherein the felt emotional state may then be converted into arousal and valence values and associated with the data matrix or matrices as described herein. At FIG. 21C, the user selects to continue to the next electronic medium 90 to build a larger dataset for use of neural analysis system 10. At FIG. 21D, the user interface 50 of electronic device 14 displays a second electronic medium 90 (e.g., an image, video, and/or sound recording) to the user (e.g., a Boston Red Sox fan) of headset 12 for a period of time, and neural analysis system 10 records data from the transcranial electrical signals detected at electrodes 16 of headset 12 during that period of time and creates a data matrix or matrices as described herein. At FIG. 21E, the user logs what he or she believes to be the emotional state felt during viewing of the second electronic medium 90, wherein the felt emotional state may then be converted into arousal and valence values and associated with the data matrix or matrices as described herein. At FIG. 21F, the user is again given the choice to continue to the next electronic medium to build a larger dataset for use of neural analysis system 10, enabling the user to continue in this loop and classify third, fourth, etc. electronic mediums until the calibration dataset is complete. As the user views and/or listens to more electronic mediums, use of neural analysis system 10 after calibration becomes more tuned to the user's particular transcranial electrical signals.

FIGS. 22A to 22D illustrate another example embodiment of method 500, in which a user may select more than one emotional state experienced for an electronic medium 90. At FIG. 22A, the user interface 50 of electronic device 14 displays an electronic medium 90 (e.g., an image, video, and/or sound recording) to the user of headset 12 for a period of time, and neural analysis system 10 records data from the transcranial electrical signals detected at electrodes 16 of headset 12 during that period of time and creates a data matrix or matrices as described herein. At FIG. 22B, the user logs what he or she believes to be multiple emotional states felt during viewing of the electronic medium 90. At step 22C, the user attempts to compare the relative amount of each emotional state felt, wherein the felt emotional state may then be converted into arousal and valence values and associated with the data matrix or matrices (e.g., arousal and valence values between two emotional states on the FIG. 20 plot based on the percentages of each emotional state selected by the user). At FIG. 22D, the user is again given the choice to continue to the next electronic medium 90 to build a larger calibration dataset for use of neural analysis system 10.

Figures 23A, 23B, 23C:
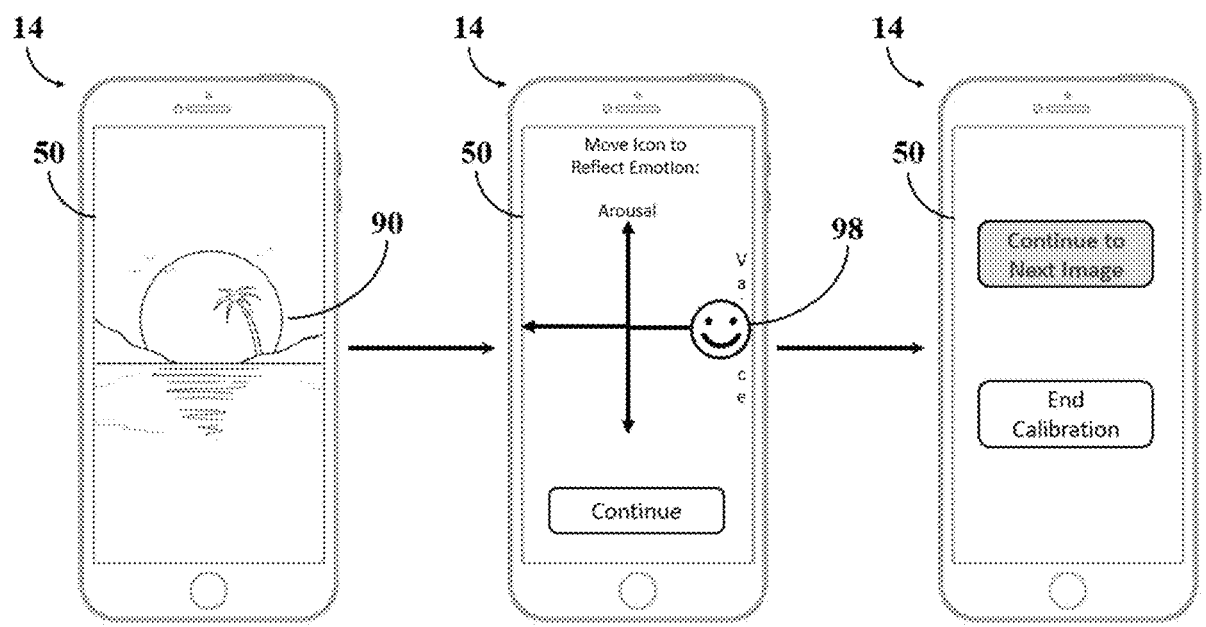
FIGS. 23A to 23C illustrate example embodiments of a user interface during the method of FIG. 20A.

FIGS. 23A to 23C illustrate another example embodiment of method 500a, in which a user may slide an icon along a plot similar to that shown in FIG. 20 for the user to indicate his or her emotion. At FIG. 23A, the user interface 50 of electronic device 14 displays an electronic medium 90 (e.g., an image, video, and/or sound recording) to the user of headset 12 for a period of time, and neural analysis system 10 records data from the transcranial electrical signals detected at electrodes 16 of headset 12 during that period of time and creates a data matrix or matrices as described herein. At FIG. 23B, the user slides an icon 98 along the arousal and valence plot shown on user interface 50 to indicate the user's emotional state and/or valence and arousal levels, wherein the arousal and valence values may then be associated with the data matrix or matrices. At FIG. 23C, the user selects to continue to the next electronic medium 90 to build a larger dataset for use of neural analysis system 10.

Figure 24:
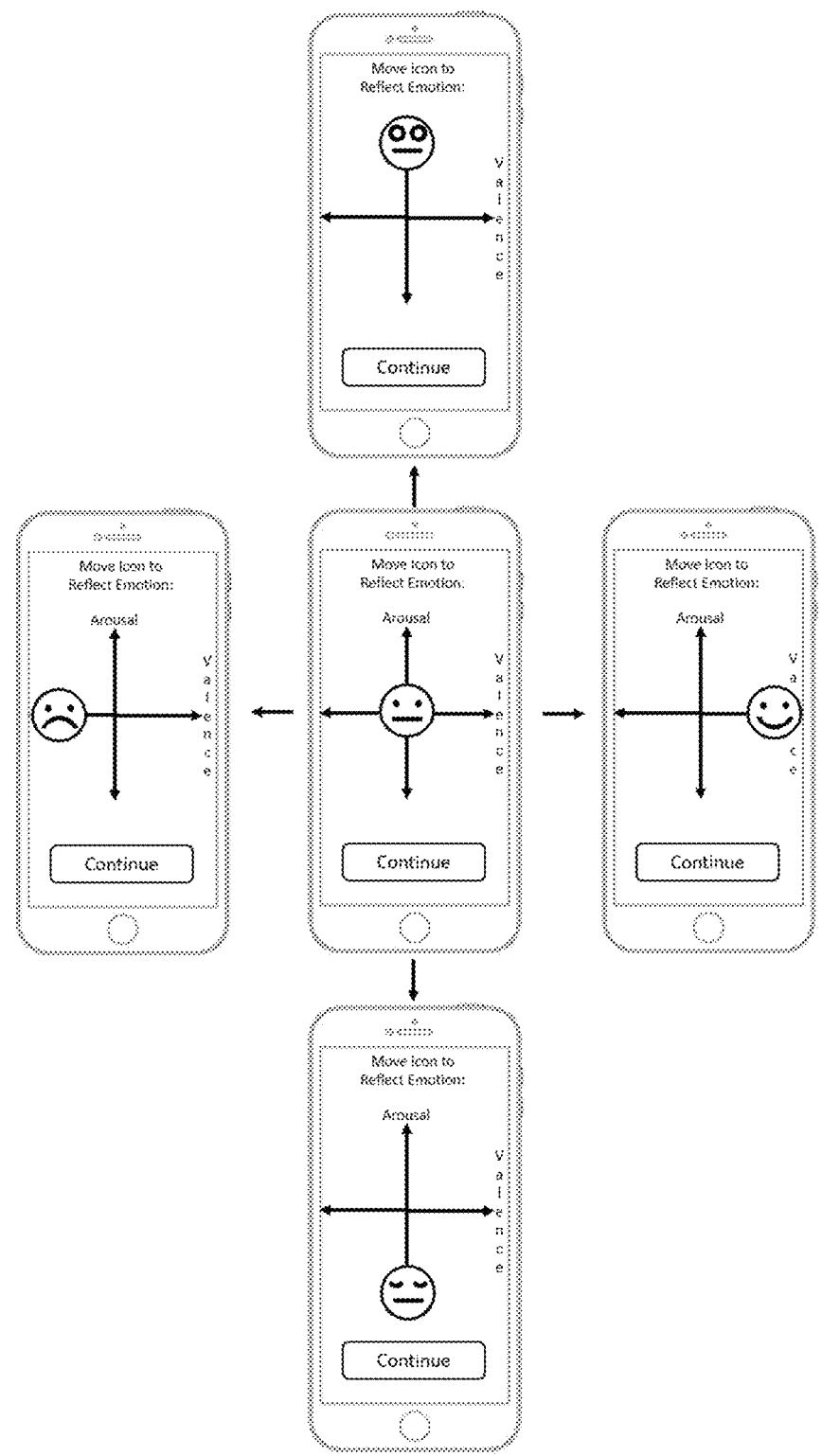
FIG. 24 illustrates an example embodiment of a user interface during the method of FIG. 20A.

FIG. 24 illustrates an example embodiment of how icon 98 may change as the user moves icon 98 across the arousal and valence plot, to assist the user and indicate the corresponding emotional state being felt. In the illustrated embodiment, the icon is an emotional face (e.g., emoticon) that changes as it moves around the screen. In the center, the icon 98 is an emoticon with a neutral facial expression (e.g., neutral eyes and mouth). As valence decreases, the mouth of the icon becomes more unhappy (e.g., more curved downward) the farther to the left the icon moves. As valence increases, the mouth of the icon 98 becomes happier (e.g., more curved upward) the farther to the right the icon 98 moves. As arousal decreases, the eyes of the icon 98 become sleepier (e.g., more closed and/or curved) the farther down the icon moves. As arousal increases, the eyes of the icon 98 become more excited (e.g., wider) the farther up the icon 98 moves. When the user moves the icon 98 both horizontally and vertically, a combination of eyes and mouth may change accordingly. By structuring the icon 98 in this way, the facial expression of the icon 98 can help indicate the chosen mood as the user slides the icon 98 across the display of the user interface 50.

Those of ordinary skill in the art will recognize from this disclosure additional ways to structure a changing icon 98. In an embodiment, user interface 50 may also display the closest emotion(s) to the icon 98 as the icon is sliding across the screen (e.g., user interface displays the word "Joy" when the icon is closest to the arousal and valence values indicating joy).

In FIGS. 21A to 21F, 22A to 22D, 23A to 23C and 24, electronic device 14 is a cellular phone, and the electronic media 90 are shown as images/videos that are displayed on the cellular phone. It should be understood, however, that the electronic media 90 do not need to be provided by the same electronic device 14 on which the emotional selection is made, as long as a matrix of data is recorded from the electrodes 16 of headset 12 and coordinated with an emotional state. It should further be understood that calibration may be performed on any type of one or more electronic device 14 having a display/user interface 50.

The electronic media 90 also do not need to be preprogrammed into electronic device 14. In an embodiment, the user is enabled to provide/view images, videos or sounds that the user knows will evoke a particular emotional state in himself or herself.

In an embodiment, the user may abbreviate or enhance a current calibration procedure, for example, by using some or all of the data matrices from a saved calibration procedure. For example, if the user has twenty (20) data matrices from a saved calibration procedure, and ten (10) data matrices from a current calibration procedure, the user may begin use of neural analysis system 10 with a total of thirty (30) data matrices of user data to use for various applications.

In an embodiment, neural analysis system 10 may adjust for the user having elevated or depressed emotional states during a saved or current calibration procedure by scaling the saved data to more closely match the current data, or vice versa. For example, if the user was more emotional (e.g., higher peaks and valleys in data) during a past session, the saved data could be scaled back to more closely match the user's current emotional state. Likewise, if the user was less emotional (e.g., lower peaks and valleys in data) during a past session, the saved data could be scaled up to more closely match the user's current emotional state.

In another embodiment, saved calibration data is always scaled down in comparison with current data, assuming that the user's past emotional states will rarely or never precisely match the user's current emotional state, thus meaning that the current emotional state should be weighed more heavily.

In an embodiment, neural analysis system 10 may adjust for the user having elevated or depressed emotional states during a saved or current calibration procedure by applying weights to the saved or current calibration data. For example, if the user was more emotional (e.g., higher peaks and valleys in data) during a past session, the saved data could be multiplied by fractional weights to decrease the significance of past data in comparison with current data. Likewise, if the user was less emotional (e.g., lower peaks and valleys in data) during a past session, the saved data could be multiplied by weights above one (1) to increase the value of past numbers. In another embodiment, weights could be added or subtracted from values in past or current data matrices.

In another embodiment, saved calibration data is always be multiplied by fractional weights to decrease the significance of past data in comparison with current data, assuming that the user's past emotional states will rarely or never precisely match the user's current emotional state, thus meaning that the current emotional state should be weighed more heavily.

Second Example Embodiment of Calibration of Headset for a Current User (Directional Embodiment)

Figure 25A:
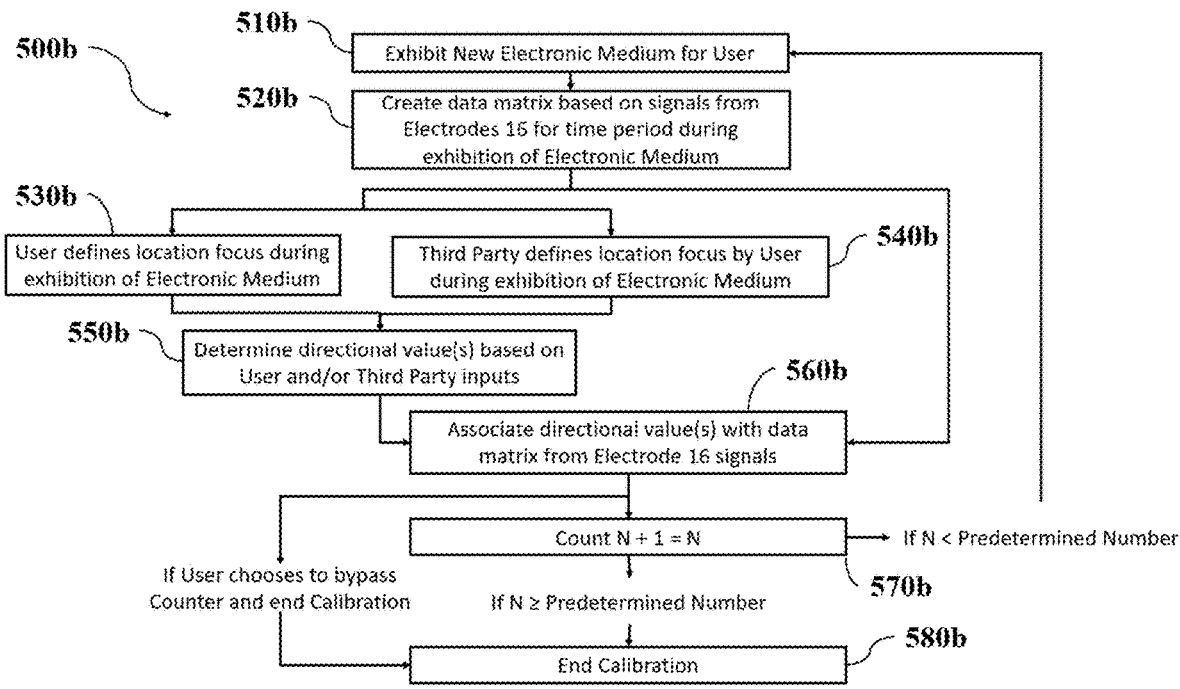
FIG. 25A illustrates an example embodiment of the method of FIG. 19A.

FIG. 25A illustrates an example method 500b illustrating how a current user may calibrate headset 12 for use in determining one or more directional position desired by a user. It should be understood that some of the steps described herein may be reordered or omitted, while other steps may be added, without departing from the spirit and scope of method 500b of FIG. 25A. It should further be understood that one or more of the steps of method 500b may be controlled by the control unit of neural analysis system 10 based on instructions stored on a memory and executed by a processor.

In this example embodiment, the one or more user values are directional values, and the one or more user output state is a desired directional position. The directional values can include, for example, one or more horizontal value, one or more vertical value, and one or more depth value. For example, a first user value can be a horizontal value, a second user value can be a vertical value, and a third user value can be a depth value. The desired directional position can include, for example, a position on the display of the user interface or other device which is desired or concentrated on by the user (e.g., the top corner of a display screen, bottom segment, specific points on the display screen, etc.).

At step 510b, electronic device 14 exhibits a first electronic medium 90 for the user wearing headset 12. The first electronic medium 90 may include, for example, an image that is displayed by electronic device 14. In an alternative embodiment, the user may be shown a medium (e.g., image, photograph, etc.) by a third party instead of viewing using electronic device 14.

At step 520b, the control unit of neural analysis system 10 creates one or more data matrix based on the signals received from the plurality of electrodes 16. In the illustrated embodiment, the signal from each electrode 16 signifies the voltage at the electrode over a period of time. In an embodiment, the control unit of neural analysis system breaks the signal from each electrode 16 into smaller time segments (e.g., $t_1, t_2, t_3 \ldots t_n$), and then creates a matrix of values (e.g., a matrix of voltage data) using the time segments from one or more electrode 16. In an embodiment, the control unit creates a single matrix with values from some or all of the electrodes 16 for further processing. In an alternative embodiment, a separate matrix is formed for each electrode 16.

At step 530b, the user inputs his or her intended direction position when viewing the first electronic medium 90. In an embodiment, the user may be presented with a plurality of directional selections to choose from on user interface 50 of electronic device 14. In an alternative embodiment, the user may define the intended direction by inputting the intended direction into user interface 50 of electronic device 14. Here, the first electronic medium may include a blank display screen for the user to select a directional position on. Additionally, step 520b may be performed simultaneously with step 530b, such that the data matrix created at step 520 be is based on signals from headset 12 which occur as the user makes his or her input regarding the intended direction.

At step 540b, a third party may input what he or she believes to be the directional position intended by the user when the user viewed and/or listened to the first electronic medium 90. In an embodiment, the third party may be presented with a plurality of preset directional positions to choose from.

In an embodiment, both the user of headset 12 and the third party may make an independent determination of what is believed to be the user's intended directional position, and both of these inputs may be used subsequently to gain a more accurate reading with a more robust set of data. The user and the third party may make their inputs on the same electronic device 14 or on different electronic devices 14.

Figure 25B:
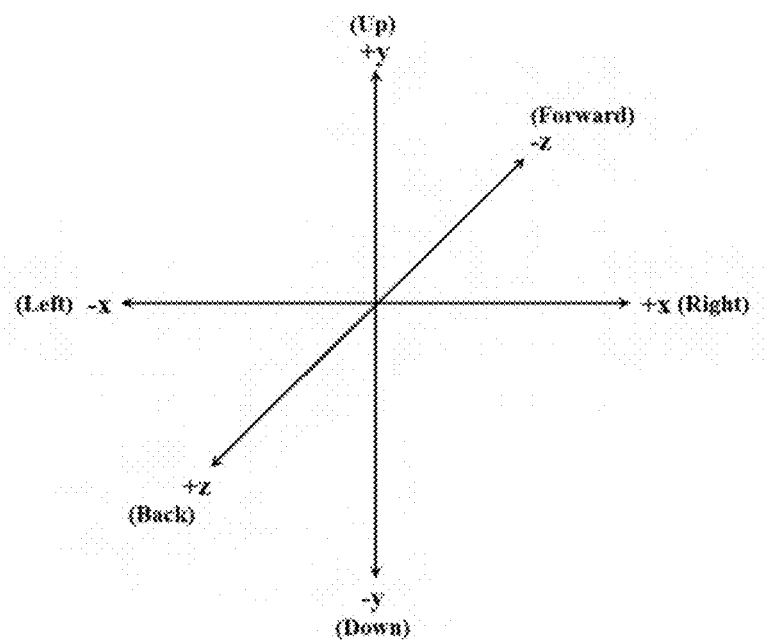
FIG. 25B illustrates an example embodiment of the plot of FIG. 19B to be used with the method of FIG. 25A.

At step 550b, directional values may be determined by the input from the user and/or third party. In an embodiment, the directional values may be determined by the directional position input by the user by associating the input with numerical values, for example, using a plot as shown in FIG. 25B or a similar computation. In another embodiment, the directional values may be input directly by the user or third party.

As illustrated by FIG. 25B, directional positions may be defined on a three-dimensional plot of horizontal values (x), vertical values (y), and depth values (z). In the present example, horizontal, vertical, and depth values may be attributed a specific location on a display of the display screen of an electronic device 14. In another embodiment, directional positions may be defined on a two-dimensional plot of horizontal and vertical values. Those of ordinary skill in the art will recognize from this disclosure that a one-dimensional or other multi-dimensional plot may also be used.

At step 560b, the data matrix or matrices from step 520a is associated with the determined directional values and/or intended directional position, and the combination is stored for training, validation and/or testing as described in more detail below.

At step 570b, the control unit of neural analysis system 10 adds to a counter. For example, counter may start at zero (0) and add one (1) to the counter each time step 570 occurs. Method 500b then returns to step 510a and proceeds through steps 510b, 520b, 530b/540b, 550b and 560b with a second electronic medium 90. The next time the method reaches step 570b, another one (1) may be added to the previously counted one (1), making N=2. The process may then continue with a third electronic medium 90, fourth electronic medium 90, etc. until N is reached.

When the counter reaches number N, user calibration is complete at step 580b, and neural analysis system 10 may move on to training, validation and/or testing. Number N may be preset, or may be chosen by the user and/or third party, before or at the beginning of calibration, depending for example on the amount of time the user and/or third party wishes to spend calibrating the device. The higher number N is, the more accurate the user's calibration is expected to be. In an embodiment, the user may bypass step 570b and end calibration at any time the user wishes, or the user at step 560b may be given the option of viewing/listening to another electronic medium or ending calibration.

In an embodiment, the control unit of neural analysis system 10 may save the calibration data for a particular user or multiple users. The user may then recall the saved calibration data during a later session and use the saved calibration data to: (i) skip a current calibration procedure; (ii) abbreviate a current calibration procedure; and/or (iii) enhance a current calibration procedure. In an embodiment, the data from calibration may also be added to the subtype database to improve the subtype database for future use.

In an embodiment, the user may skip a current calibration procedure and use the previously saved calibration data matrices to use headset 12. This may, however, cause the determinations by neural analysis system 10 to be less accurate than if a current calibration is performed, for example, because the user may have different states in comparison with his or her states when the saved calibration was performed, as explained above.

In an embodiment, each of the users whose data is used to determine the subtype database of FIG. 17 has also gone through the process of FIG. 25A or a similar process, so that the subtype database includes data matrices associated with directional values for each subtype. In an embodiment, method 500b shown in FIG. 25A is performed at step 310 of method 300 discussed above to create the initial subtype database. In another embodiment, method 500b shown in FIG. 25A is performed by each user of method 300 after each user has been classified into a subtype.

Figure 26A:
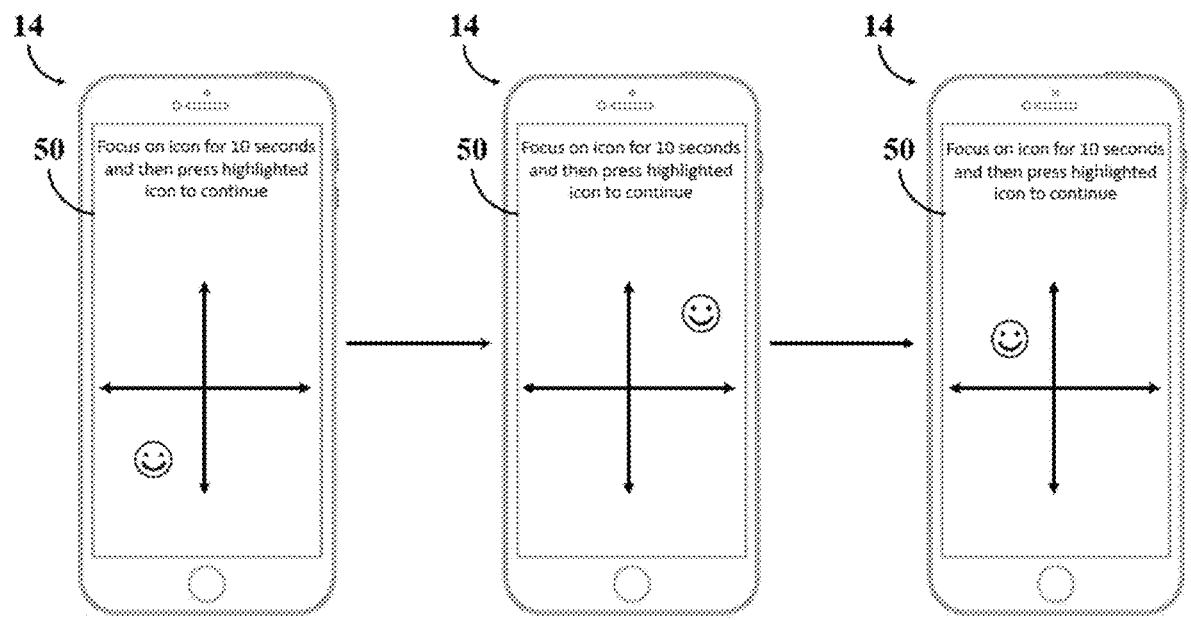
FIGS. 26A and 26B illustrate example embodiments of a user interface during the method of FIG. 25A.
Figure 26B:
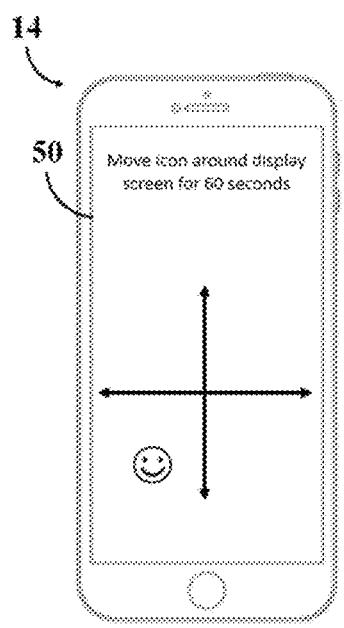

FIGS. 26A and 26B show example embodiments of the user interface 50 of electronic device 14 during the above-described calibration process. It should be understood that FIGS. 26A and 26B demonstrate examples only, that the calibration method 500b described herein is not limited to these examples, and that modifications may be made to the method of calibration described herein with departing from the spirit and scope of the present disclosure.

In FIG. 26A, the user interface 50 of electronic device 14 displays a first electronic medium 90 (e.g., a smiley icon) on a specific portion of the display screen, and the user is asked to focus on the icon and then press the icon to continue. As the user presses focusses on and/or presses the icon, neural analysis system 10 records data from the transcranial electrical signals detected at electrodes 16 of headset 12 during that period of time and creates a data matrix or matrices as described herein. The process can be repeated multiple times for multiple directional positions directions. Alternatively, first electronic medium 90 can include a blank display screen in which the user touches to demonstrate an intended directional position.

In FIG. 26B, the user interface displays a first a first electronic medium 90 (e.g., a smiley icon) and enables the user to move the icon around the screen. As the user presses moves the icon around the screen, neural analysis system 10 records data from the transcranial electrical signals detected at electrodes 16 of headset 12 during that period of time and creates a data matrix or matrices as described herein. Various data from the data matrix can then be associate with various directional positions of the icon on the display screen. Alternatively, first electronic medium 90 can include a blank display screen in which the user moves his or her finger across to demonstrate an intended directional position.

In an embodiment, the user may abbreviate or enhance a current calibration procedure, for example, by using some or all of the data matrices from a saved calibration procedure. For example, if the user has twenty (20) data matrices from a saved calibration procedure, and ten (10) data matrices from a current calibration procedure, the user may begin use of neural analysis system 10 with a total of thirty (30) data matrices of user data to use for various applications.

As discussed above, neural analysis system 10 may also adjust for the user having different states during a saved or current calibration procedure by scaling the saved data and/or using weights to more closely match the current data, or vice versa.

Training, Validation and Testing Using User's Calibration Data

FIG. 27 illustrates an example method 150 illustrating how a current user may perform training method 600, validation method 700 and/or testing method 800 to prepare neural analysis system 10 for use for various applications. It should be understood that some of the steps described herein may be reordered or omitted, while other steps may be added, without departing from the spirit and scope of the method 150 of FIG. 27. It should further be understood that one or more of the steps of method 150 may be controlled by the control unit of neural analysis system 10 based on instructions stored on a memory and executed by a processor.

At step 160, the control unit of neural analysis system 10 has a series of calibration data from the user's calibration, with the calibration data including data matrices from electrodes 16 associated with user output states and/or user values input by the user and/or a third party. The control unit then separates the calibration data into multiple portions of user data. In the illustrated embodiment, the control unit separates the calibration data into a first portion of user data at step 610 (e.g., including 75% of the user calibration data) and a second portion of user data at 710 (e.g., including 25% of the user calibration data).

In an embodiment, the matrices in the first and second portions of user data include data from only the most effective electrodes 16 for the user as determined, for example, by method 400 of FIG. 18. In another embodiment, the matrices in the first and second portions of user data include data from all electrodes 16 of headset 12.

At step 630, the first portion of user data from step 610 is combined with the historical data sets from user's subtype in the subtype database shown at step 620, giving a much larger dataset than the user's own data to improve calibration time and accuracy. In the illustrated embodiment, the historical data is in the same format as the first portion of user data, with the historical data including data matrices from one or more electrodes 16 associated with user output states and/or user values. In an embodiment, the first portion of user data may be weighed more heavily than the historical data.

At step 640, one or more neural networks are trained, for example, using Transfer Learning Type training, to separate the combined data into relevant data and non-relevant data, essentially eliminating the non-relevant data so that only relevant data is processed in further steps. The one or more neural networks may be, for example, convolutional neural networks, recurrent neural networks, or a combination of convolutional and recurrent neural networks. The one or more neural networks may be trained, for example, using data matrices known to be associated with relevant data. In an embodiment, step 640 may be omitted, may occur prior to method 600 being executed, or may occur after method 600 being executed.

At step 650, a plurality of neural networks are further trained using the combined data, for example, using Transfer Learning Type training, to output a first user value based on one or more input matrix of data from the signals from electrodes 16. The one or more neural networks may be, for example, convolutional neural networks, recurrent neural networks, or a combination of convolutional and recurrent neural networks.

At step 660, a plurality of neural networks are further trained using the combined data, for example, using Transfer Learning Type training, to output a second user value based on one or more input matrix of data from the signals from electrodes 16. The one or more neural networks may be, for example, convolutional neural networks, recurrent neural networks, or a combination of convolutional and recurrent neural networks.

In the illustrated embodiment, separate neural networks are trained to determine first and second user values. In an alternative embodiment, the same neural networks may determine both the first and second user values, for example, by combining steps 650 and 660. Additionally, steps 650 and 660 may be expanded to determine third user value, a fourth user value, etc. for any many user values are desired.

At step 670, the plurality of neural networks have been trained for both the first and second user values, and training method 600 is complete. In an embodiment, at least ten (10) neural networks have been trained for the first user value, and at least ten (10) neural networks have been trained for the second user value.

Once the neural networks have been trained, the trained neural networks may be validated at step 720 using the second portion of user data from step 710. Since the trained neural networks did not receive the second portion of user data during training, it can be determined whether or not training was successful by inputting the data matrices from the second portion of user data into the trained neural networks, and evaluating whether the trained neural networks output the expected corresponding first and second values. If the trained neural networks output first and second values that are determined to be within a certain amount of error, then the control unit of neural analysis system 10 may validate that the training was successful and testing is complete. In an embodiment, if some, but not all, of the trained neural networks output results within a certain amount of error, then the method may proceed with those trained neural networks.

Once the neural networks have been validated, the validated neural networks may be tested at step 810 using some or all of the user calibration data. During testing, each of the validated neural networks are tested for accuracy. For example, accuracy may be determined by how close each neural network gets to the expected first/second values when the user data is input.

At step 820, a certain number of the most accurate neural networks from the testing at step 810 are chosen to be used for the particular user of headset 12. In an embodiment with at least ten (10) neural networks for the first value and at least ten (10) neural networks for the second value, the control unit may select to proceed with, for example, the three (3) most accurate neural networks for the first value 932 and the three most accurate neural networks for the second value 942.

First Example Embodiment of Training, Validation and Testing Using User's Calibration Data (Emotion Embodiment)

FIG. 28 illustrates an example method 150*a* illustrating how a current user may perform training method 600*a*, validation method 700*a* and/or testing method 800*a* to prepare neural analysis system 10 to detect a user's emotional state. It should be understood that some of the steps described herein may be reordered or omitted, while other steps may be added, without departing from the spirit and scope of the method 150*a* of FIG. 28. It should further be understood that one or more of the steps of method 150*a* may be controlled by the control unit of neural analysis system 10 based on instructions stored on a memory and executed by a processor.

At step 160*a*, the control unit of neural analysis system has a series of calibration data from the user's calibration, with the calibration data including data matrices from electrodes 16 associated with emotional states and/or arousal and valence values input by the user and/or a third party. The control unit then separates the calibration data into multiple portions of user data. In the illustrated embodiment, the control unit separates the calibration data into a first portion of user data at step 610*a* (e.g., including 75% of the user calibration data) and a second portion of user data at 710*a* (e.g., including 25% of the user calibration data).

In an embodiment, the matrices in the first and second portions of user data include data from only the most effective electrodes 16 for the user as determined, for example, by method 400 of FIG. 18. In another embodiment, the matrices in the first and second portions of user data include data from all electrodes 16 of headset 12.

At step 630*a*, the first portion of user data from step 610*a* is combined with the historical data sets from user's subtype in the subtype database shown at step 620*a*, giving a much larger dataset than the user's own data to improve calibration time and accuracy. In the illustrated embodiment, the historical data is in the same format as the first portion of user data, with the historical data including data matrices from one or more electrodes 16 associated with emotional states and/or arousal and valence values. In an embodiment, the first portion of user data may be weighed more heavily than the historical data.

At step 640*a*, one or more neural networks are trained, for example, using Transfer Learning Type training, to separate the combined data into emotional states and non-emotions, essentially eliminating the non-emotional states so that only emotional states are processed for arousal and valence values. The one or more neural networks may be, for example, convolutional neural networks, recurrent neural networks, or a combination of convolutional and recurrent neural networks. The one or more neural networks may be trained, for example, using data matrices known to be associated with an emotion or non-emotion. In an embodiment, step 640*a* may be omitted, may occur prior to method 600*a* being executed, or may occur after method 600*a* being executed.

At step 650*a*, a plurality of neural networks are further trained using the combined data, for example, using Transfer Learning Type training, to output an arousal value based on one or more input matrix of data from the signals from electrodes 16. The one or more neural networks may be, for example, convolutional neural networks, recurrent neural networks, or a combination of convolutional and recurrent neural networks.

At step 660*a*, a plurality of neural networks are further trained using the combined data, for example, using Transfer Learning Type training, to output a valence value based on one or more input matrix of data from the signals from electrodes 16. The one or more neural networks may be, for example, convolutional neural networks, recurrent neural networks, or a combination of convolutional and recurrent neural networks.

In the illustrated embodiment, separate neural networks are trained to determine arousal and valence. In an alternative embodiment, the same neural networks may determine both arousal and valence, for example, by combining steps 650*a* and 660*a*. Additionally, steps 650 and 660 may be expanded to determine third user value, a fourth user value, etc. for any many user values are desired. A third user value relevant to determining emotional states involves dominance, as discussed above.

At step 670*a*, the plurality of neural networks have been trained for both arousal and valence, and training method 600*a* is complete. In an embodiment, at least ten (10) neural networks have been trained for arousal, and at least ten (10) neural networks have been trained for valence.

Once the neural networks have been trained, the trained neural networks may be validated at step 720*a* using the second portion of user data from step 710*a*. Since the trained neural networks did not receive the second portion of user data during training, it can be determined whether or not training was successful by inputting the data matrices from the second portion of user data into the trained neural networks, and evaluating whether the trained neural networks output the expected corresponding arousal and valences. If the trained neural networks output arousal and valence values that are determined to be within a certain amount of error, then the control unit of neural analysis system 10 may validate that the training was successful and testing is complete. In an embodiment, if some, but not all, of the trained neural networks output results within a certain amount of error, then the method may proceed with those trained neural networks.

Once the neural networks have been validated, the validated neural networks may be tested at step 810a using some or all of the user calibration data. During testing, each of the validated neural networks are tested for accuracy. For example, accuracy may be determined by how close each neural network gets to the expected arousal/valence values when the user data is input.

At step 820a, a certain number of the most accurate neural networks from the testing at step 810a are chosen to be used for the particular user of headset 12. In an embodiment with at least ten (10) neural networks for arousal and at least ten (10) neural networks for valence, the control unit may select to proceed with, for example, the three (3) most accurate neural networks for arousal 932a and the three most accurate neural networks for valence 942a.

Second Example Embodiment of Training, Validation and Testing Using User's Calibration Data (Directional Embodiment)

FIG. 29 illustrates an example method 150b illustrating how a current user may perform training method 600b, validation method 700b and/or testing method 800b to prepare neural analysis system 10 for use for directional positioning, e.g. of an icon (e.g., a video game avatar or other icon). It should be understood that some of the steps described herein may be reordered or omitted, while other steps may be added, without departing from the spirit and scope of the method 150b of FIG. 29. It should further be understood that one or more of the steps of method 150a may be controlled by the control unit of neural analysis system 10 based on instructions stored on a memory and executed by a processor.

At step 160b, the control unit of neural analysis system has a series of calibration data from the user's calibration, with the calibration data including data matrices from electrodes 16 associated with directional values and/or directional positions input by the user and/or a third party. The control unit then separates the calibration data into multiple portions of user data. In the illustrated embodiment, the control unit separates the calibration data into a first portion of user data at step 610b (e.g., including 75% of the user calibration data) and a second portion of user data at 710b (e.g., including 25% of the user calibration data).

In an embodiment, the matrices in the first and second portions of user data include data from only the most effective electrodes 16 for the user as determined, for example, by method 400 of FIG. 18. In another embodiment, the matrices in the first and second portions of user data include data from all electrodes 16 of headset 12.

At step 630b, the first portion of user data from step 610b is combined with the historical data sets from user's subtype in the subtype database shown at step 620b, giving a much larger dataset than the user's own data to improve calibration time and accuracy. In the illustrated embodiment, the historical data is in the same format as the first portion of user data, with the historical data including data matrices from one or more electrodes 16 associated with directional values. In an embodiment, the first portion of user data may be weighed more heavily than the historical data.

At step 640b, one or more neural networks are trained, for example, using Transfer Learning Type training, to separate the combined data into directional data and non-directional data, essentially eliminating the non-directional data so that only directional data is processed for horizontal, vertical, and/or depth values. The one or more neural networks may be, for example, convolutional neural networks, recurrent neural networks, or a combination of convolutional and recurrent neural networks. The one or more neural networks may be trained, for example, using data matrices known to be associated with a direction or non-direction. In an embodiment, step 640b may be omitted, may occur prior to method 600b being executed, or may occur after method 600b being executed.

At step 650b, a plurality of neural networks are further trained using the combined data, for example, using Transfer Learning Type training, to output a horizontal value based on one or more input matrix of data from the signals from electrodes 16. The one or more neural networks may be, for example, convolutional neural networks, recurrent neural networks, or a combination of convolutional and recurrent neural networks.

At step 660b, a plurality of neural networks are further trained using the combined data, for example, using Transfer Learning Type training, to output a vertical value based on one or more input matrix of data from the signals from electrodes 16. The one or more neural networks may be, for example, convolutional neural networks, recurrent neural networks, or a combination of convolutional and recurrent neural networks.

The method may further include a step 660c (not shown), in which a plurality of neural networks are further trained using the combined data, for example, using Transfer Learning Type training, to output a depth value based on one or more input matrix of data from the signals from electrodes 16. The one or more neural networks may be, for example, convolutional neural networks, recurrent neural networks, or a combination of convolutional and recurrent neural networks.

In the illustrated embodiment, separate neural networks are trained to determine horizontal, vertical, and depth values. In an alternative embodiment, the same neural networks may determine all of the horizontal, vertical, and depth values, for example, by combining steps 650b, 660b, and 665b. Additionally, steps 650 and 660 may be expanded to determine third user value, a fourth user value, etc. for any many user values are desired. Again, a third user value relevant to determining directional positioning involves depth.

At step 670b, the plurality of neural networks have been trained for horizontal, vertical, and/or depth values, and training method 600b is complete. In an embodiment, at least ten (10) neural networks have been trained for the horizontal value, at least ten (10) neural networks have been trained for the vertical value, and at least ten (10) neural networks have been trained for the depth value.

Once the neural networks have been trained, the trained neural networks may be validated at step 720b using the second portion of user data from step 710b. Since the trained neural networks did not receive the second portion of user data during training, it can be determined whether or not training was successful by inputting the data matrices from the second portion of user data into the trained neural networks, and evaluating whether the trained neural networks output the expected corresponding horizontal, vertical, and/or depth values. If the trained neural networks output horizontal, vertical, and/or depth values that are determined to be within a certain amount of error, then the control unit of neural analysis system 10 may validate that the training was successful and testing is complete. In an embodiment, if some, but not all, of the trained neural networks output results within a certain amount of error, then the method may proceed with those trained neural networks.

Once the neural networks have been validated, the validated neural networks may be tested at step 810b using some or all of the user calibration data. During testing, each of the validated neural networks are tested for accuracy. For example, accuracy may be determined by how close each neural network gets to the expected horizontal, vertical, and depth values when the user data is input.

At step 820b, a certain number of the most accurate neural networks from the testing at step 810b are chosen to be used for the particular user of headset 12. In an embodiment with at least ten (10) neural networks for each of the horizontal, vertical, and/or depth values, the control unit may select to proceed with, for example, the three (3) most accurate neural networks for the horizontal value 932b, the three most accurate neural networks for the vertical value, and/or the three most accurate neural networks for the depth value.

Use of Headset

Figure 30A:
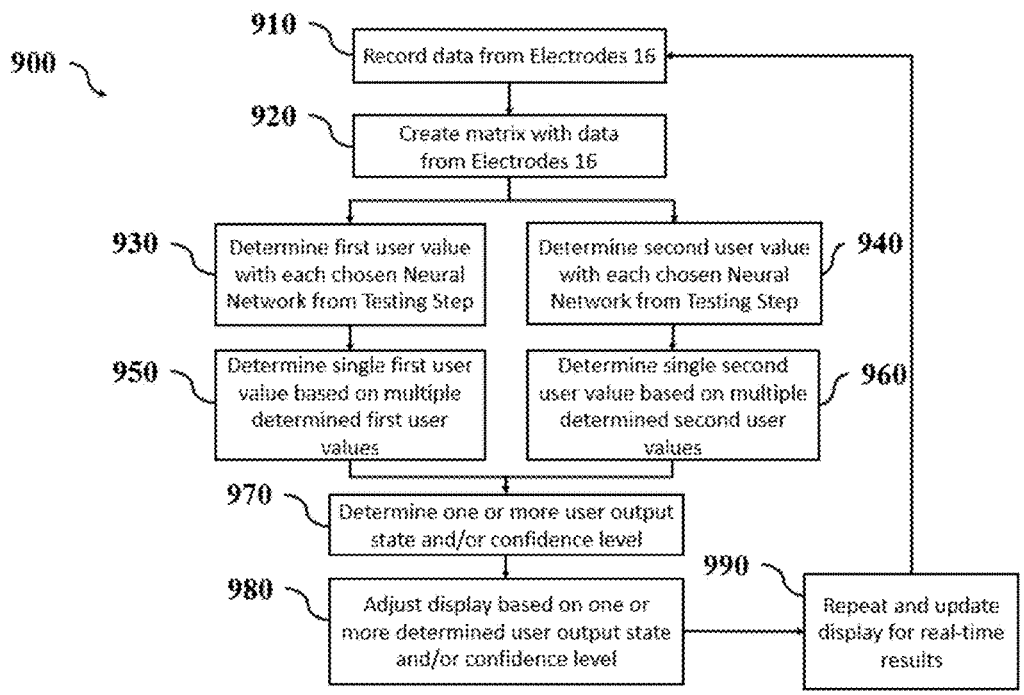
FIG. 30A illustrates an example embodiment of a method of using a neural analysis system according to the present disclosure.
Figure 30B:
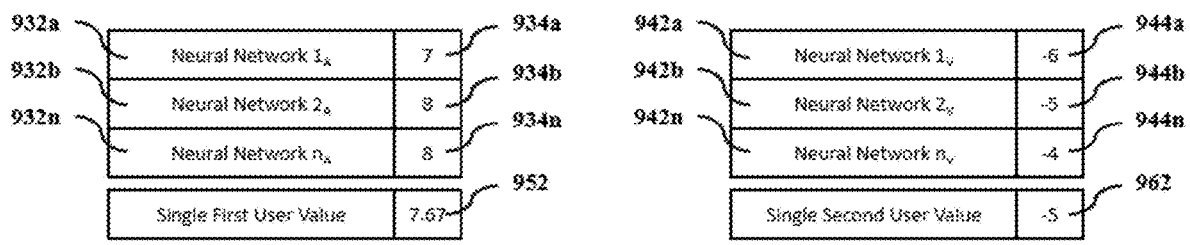
FIGS. 30B and 30C illustrate example embodiments of certain steps of the method of FIG. 30A.
Figure 30C:
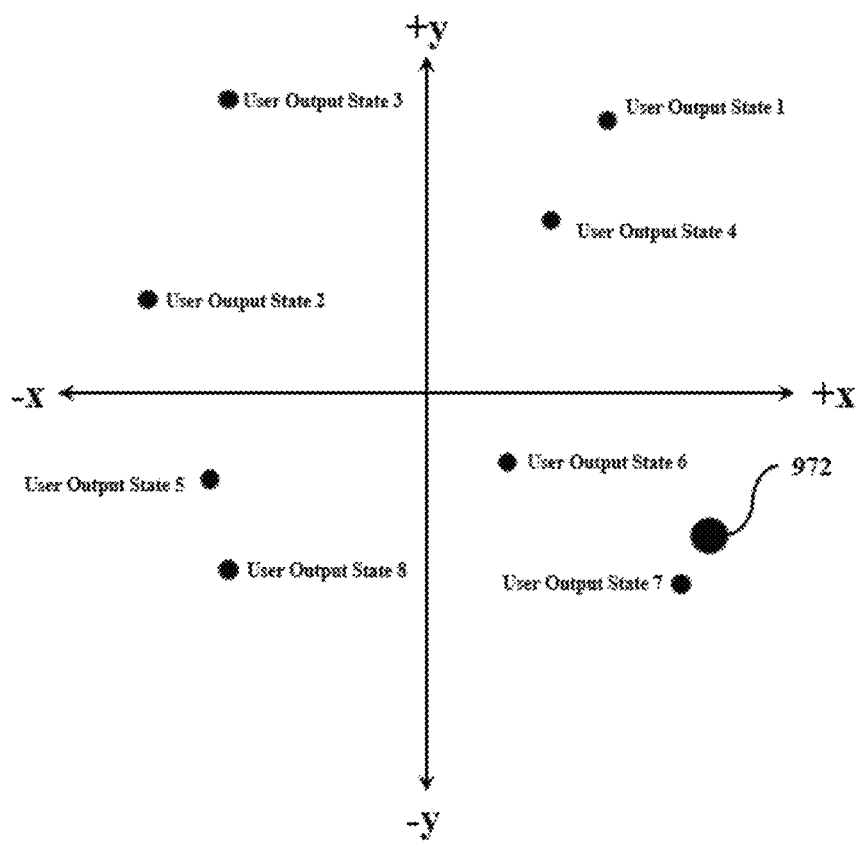

FIGS. 30A to 30C illustrates an example method 900 illustrating how neural analysis system 10 may be operated for various uses. It should be understood that some of the steps described herein may be reordered or omitted, while other steps may be added, without departing from the spirit and scope of the method 900 of FIGS. 30A to 30C. It should further be understood that one or more of the steps of method 900 may be controlled by the control unit of neural analysis system 10 based on instructions stored on a memory and executed by a processor.

At step 910, a user wearing headset 12 may begin a session. When the user begins the session, electrodes 16 are controlled to constantly or intermittently measure the user's transcranial electrical signals over a period of time. The data from electrodes 16 may be processed at headset 12 or transmitted to electronic device 14 via data transmission device 22 for further processing.

At step 920, the transcranial electrical signals from the electrodes 16 are transformed into one or more matrices as described herein. In the illustrated embodiment, the transcranial electrical signal from each electrode 16 signifies the voltage at the electrode over a period of time. In an embodiment, the control unit breaks the transcranial electrical signal from each electrode 16 into smaller time segments (e.g., $t_1$, $t_2$, $t_3$ ... $t_n$), and then creates a matrix of values (e.g., a matrix of voltage data) using the time segments from one or more electrode 16.

At step 930, the matrices are input into the trained neural networks 932 for a first user value, wherein the trained neural networks 932 were chosen from testing method 800, and each trained neural network outputs a first user value 934. FIG. 30B illustrates an example embodiment showing a plurality of trained neural networks 932a, 932b ... 932n for a first user value, wherein each trained neural network 932a, 932b ... 932n outputs a first user value 934a, 934b ... 934n.

At step 940, the matrices are input into the trained neural networks 942 for a second user value, wherein the trained neural networks 942 were chosen from testing method 800, and each trained neural network outputs a second user value 944. FIG. 30B illustrates an example embodiment showing a plurality of trained neural networks 942a, 942b ... 942n for the second user value, wherein each trained neural network 942a, 942b ... 942n outputs a second user value 944a, 944b ... 944n.

Steps 930/940 can be repeated for any number of user values (third user values, fourth user values, etc.) Different numbers of user values will be useful for different applications. Here, first and second user values are described for simplicity.

At step 950, a single first user value 952 is determined based on the first user values 934 output by the trained neural networks 932 from step 930. In an embodiment, the single first user value may be determined by averaging the results of the trained neural networks 932. For example, the example embodiment of FIG. 30B, the values 7, 8 and 8 have been averaged to return a single first user value of 7.67.

At step 960, a single second user value 962 is determined based on the second user values 944 output by the trained neural networks 942 from step 940. In an embodiment, the single second user value may be determined by averaging the results of the trained neural networks 942. For example, the example embodiment of FIG. 30B, the values −6, −5 and −4 have been averaged to return a single second user value of −5.

At step 970, the control unit may determine one or more user output states and/or confidence levels (e.g., confidence value and/or percentage) based on the single first user value 952 and single second user value 962 determined at steps 950 and 960. With a plurality of user output states associated with respective first user values and second user values from the calibration method 500 of FIG. 19A (e.g., resulting plot of FIG. 30C), the control unit may determine the one or more user output states and/or confidence levels based on the distance between the single first user value 952 and single second user value 962 plot point 972 and that of one or more user output states. For example, FIG. 30C shows the (7.67, −5) plot point 972 using the single first user value 952 and single second user value 962 determined at steps 950 and 960. As illustrated, the closest user output state is "User Output State 7," which may be determined by control unit to be the dominant user output state of the user. Additionally, the control unit may determine other secondary user output states in a certain vicinity (e.g., User Output State 6 is the next closest in FIG. 30C) to be relevant but with a lower confidence level.

At step 980, the control unit causes user interface 50 of electronic device 14 to display one or more user output state determined by the trained neural networks to be most likely based on the first and second values. In an embodiment, user interface 50 may display a plurality of user output states and the percentage match or confidence level of a match based on the vicinity of the plot point 972 to different user output states.

At step 990, the control unit returns to step 910 and processes another more current data matrix received from the electrodes 16. In this way, user interface 50 may continuously update what the user output states until the user chooses to end the process. It should be understood that each of the steps of method 900 is happening in a split-second, providing the user with constant real-time updates regarding their output state. Alternatively, method 900 may pause after step 980 until the user instructs to proceed to step 990 using user interface 50.

First Example Embodiment of Use of Headset
(Emotion Embodiment)

Figure 31A:
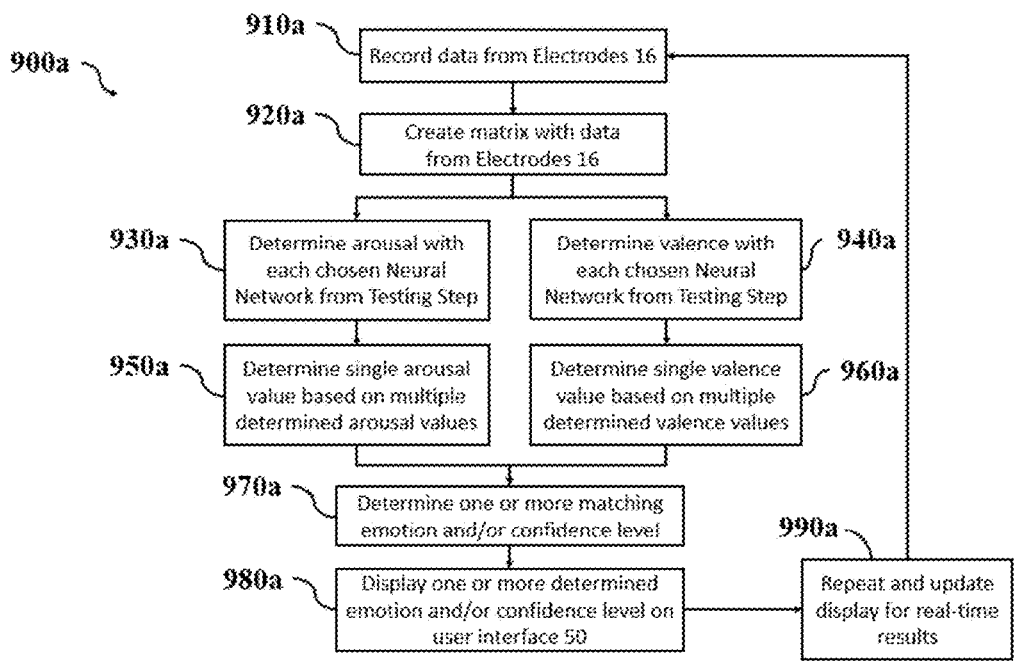
FIG. 31A illustrates an example embodiment of the method of FIG. 30A.

FIG. 31A illustrates an example method 900a illustrating how neural analysis system 10 may be operated to determine a user's emotional state. It should be understood that some of the steps described herein may be reordered or omitted, while other steps may be added, without departing from the spirit and scope of the method 900a of FIGS. 31A to 31C.

It should further be understood that one or more of the steps of method 900a may be controlled by the control unit of neural analysis system 10 based on instructions stored on a memory and executed by a processor.

At step 910a, a user wearing headset 12 may begin a session. When the user begins the session, electrodes 16 are controlled to constantly or intermittently measure the user's transcranial electrical signals over a period of time. The data from electrodes 16 may be processed at headset 12 or transmitted to electronic device 14 via data transmission device 22 for further processing.

At step 920a, the transcranial electrical signals from the electrodes 16 are transformed into one or more matrices as described herein. In the illustrated embodiment, the transcranial electrical signal from each electrode 16 signifies the voltage at the electrode over a period of time. In an embodiment, the control unit breaks the transcranial electrical signal from each electrode 16 into smaller time segments (e.g., $t_1$, $t_2$, $t_3$ ... $t_n$), and then creates a matrix of values (e.g., a matrix of voltage data) using the time segments from one or more electrode 16.

Figure 31B:
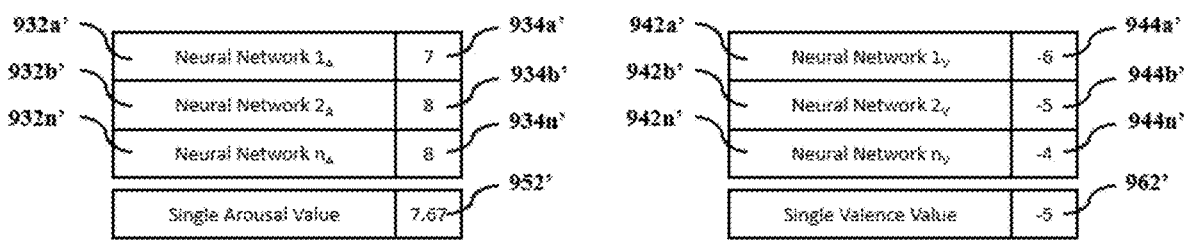
FIGS. 31B and 31C illustrate example embodiments of certain steps of the method of FIG. 31A.

At step 930a, the matrices are input into the trained neural networks 932' for arousal, wherein the trained neural networks 932' were chosen from testing method 800a, and each trained neural network outputs an arousal value 934'. FIG. 31B illustrates an example embodiment showing a plurality of trained neural networks 932a', 932b' 932n' for arousal, wherein each trained neural network 932a', 932b' . . . 932n' outputs an arousal value 934a', 934b' . . . 934n'.

At step 940a, the matrices are input into the trained neural networks 942' for valence, wherein the trained neural networks 942' were chosen from testing method 800a, and each trained neural network outputs a valence value 944'. FIG. 31B illustrates an example embodiment showing a plurality of trained neural networks 942a', 942b' 942n' for valence, wherein each trained neural network 942a', 942b' 942n' outputs a valence value 944a', 944b' 944n'.

At step 950a, a single arousal value 952' is determined based on the arousal values 934' output by the trained neural networks 932' from step 930a. In an embodiment, the single arousal value may be determined by averaging the results of the trained neural networks 932'. For example, the example embodiment of FIG. 31B, the values 7, 8 and 8 have been averaged to return a single arousal value of 7.67.

At step 960a, a single valence value 962' is determined based on the valence values 944' output by the trained neural networks 942' from step 940a. In an embodiment, the single valence value may be determined by averaging the results of the trained neural networks 942'. For example, the example embodiment of FIG. 31B, the values −6, −5 and −4 have been averaged to return a single valence value of −5.

Figure 31C:
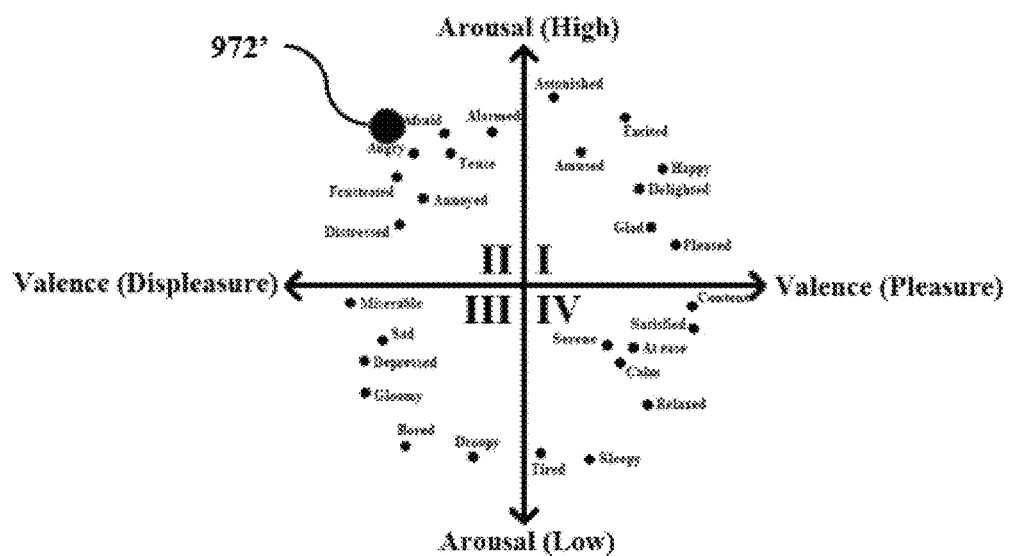

At step 970a, the control unit may determine one or more emotional states and/or confidence levels (e.g., confidence value and/or percentage) based on the single arousal value 952' and single valence value 962' determined at steps 950a and 960a. With a plurality of emotional states associated with respective arousal and valence values from the calibration method 500a of FIG. 20A (e.g., resulting plot of FIGS. 20B and/or 31C), the control unit may determine the one or more emotional states and/or confidence levels based on the distance between the single arousal value 952' and single valence value 962' plot point 972' and that of one or more emotions. For example, FIG. 31C shows the (−5, 7.67) plot point 972 using the single arousal value 952' and single valence value 962' determined at steps 950a and 960a. As illustrated, the closest emotional state is "Angry," which may be determined by control unit to be the dominant emotional state felt by the user. Additionally, the control unit may determine other secondary emotional states in a certain vicinity (e.g., "Afraid," "Frustrated," and "Tense" in FIG. 31C) to be relevant but with a lower confidence level.

At step 980a, the control unit causes user interface 50 of electronic device 14 to display one or more emotional state determined by the trained neural networks to be most likely based on the arousal and valence values. In an embodiment, user interface 50 may display a plurality of emotional states and the percentage match or confidence level of a match based on the vicinity of the plot value 972 to different emotions. FIGS. 32A to 32F illustrated example embodiments of user interface 50 using the example of FIGS. 31A to 31C.

At step 990a, the control unit returns to step 910a and processes another more current data matrix received from the electrodes 16. In this way, user interface 50 may continuously update what the user is feeling in real time, until the user chooses to end the process. It should be understood that each of the steps of method 900a is happening in a split-second, providing the user with constant real-time updates regarding their present emotional state. Alternatively, method 900a may pause after step 980a until the user instructs to proceed to step 990a using user interface 50.

Figure 32A:
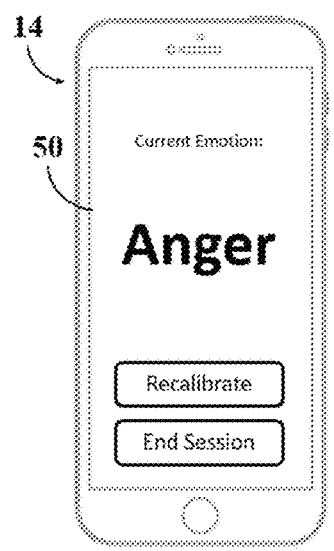
FIGS. 32A to 32F illustrate example embodiments of a user interface during the method of FIG. 31A.
Figure 32B:
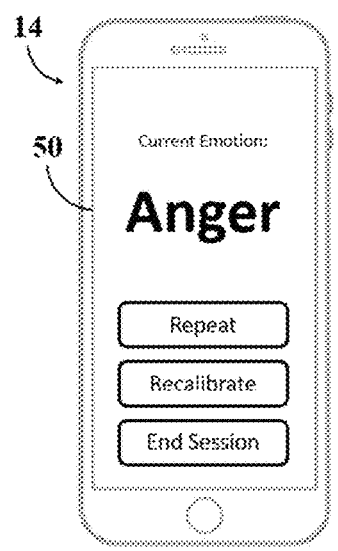
Figure 32C:
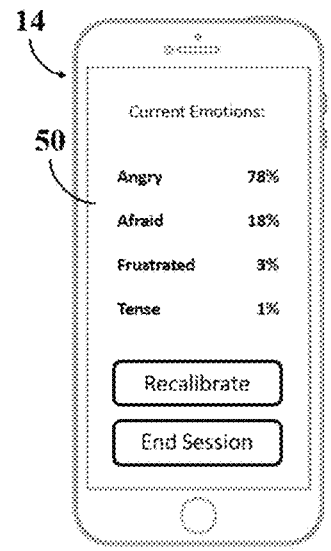

FIGS. 32A to 32F illustrate example embodiments of the user interface 50 at step 980a. In the example embodiment of FIG. 32A, user interface 50 continuously updates with the user's determined emotional state in real-time until the user chooses to end the session or recalibrate headset 12. In FIG. 32B, neural analysis system 10 proceeds from steps 910a to 980a, but then waits for the user to select REPEAT before proceeding to step 990a and updating user interface 50 with a more current emotion. In FIG. 32C, user interface 50 displays a plurality of emotional states and confidence levels (e.g., percentages), either in real time or with the user updating periodically.

Figure 32D:
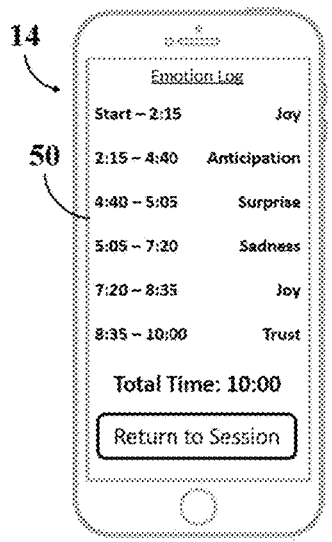

In another embodiment, the control unit of neural analysis system 10 may store a log of the user's emotional states over a period of time, so that the log can be viewed after the session to give the user or a third party such as a therapist a broader overall view of the changes in the user's emotional state. FIG. 32D illustrates an example embodiment of one such log.

Figure 32E:
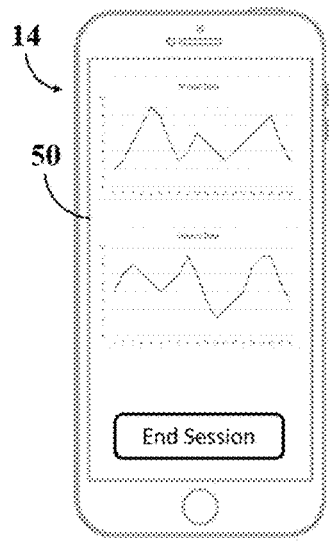
Figure 32F:
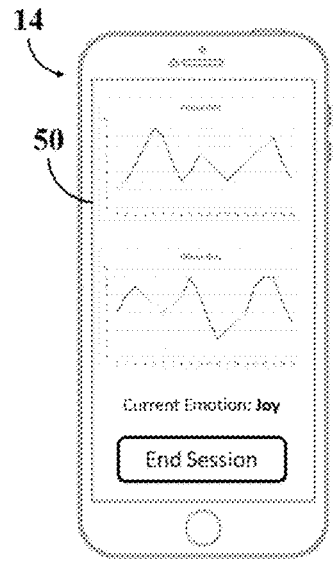

In another embodiment, instead of or in addition to displaying the user's emotion, user interface 50 may display, for example, real-time graphs or values for the arousal and valence values, as illustrated for example by FIGS. 32E and 32F. In FIGS. 32E and 32F, the arousal and valence graphs are provided with real-time updates, giving the user or a third party a visual representation (e.g., scrolling line graph), wherein it can be noted when the user reaches highs and lows in each set of values. In FIG. 32F, the user's current dominant emotional state is also shown with the real-time arousal and valence charts, giving the user or a third party a visual representation of the excitement and attractiveness/averseness of the main emotional state being detected.

Although the above method is described in terms of arousal and valence data, it should be understood by those of ordinary skill in the art from this disclosure that a third user value of dominance could also be used in the same way to achieve more accurate results. Fourth, fifth, etc. values can also be used as desired in the same way.

Second Example Embodiment of Use of Headset
(Directional Embodiment)

Figure 33A:
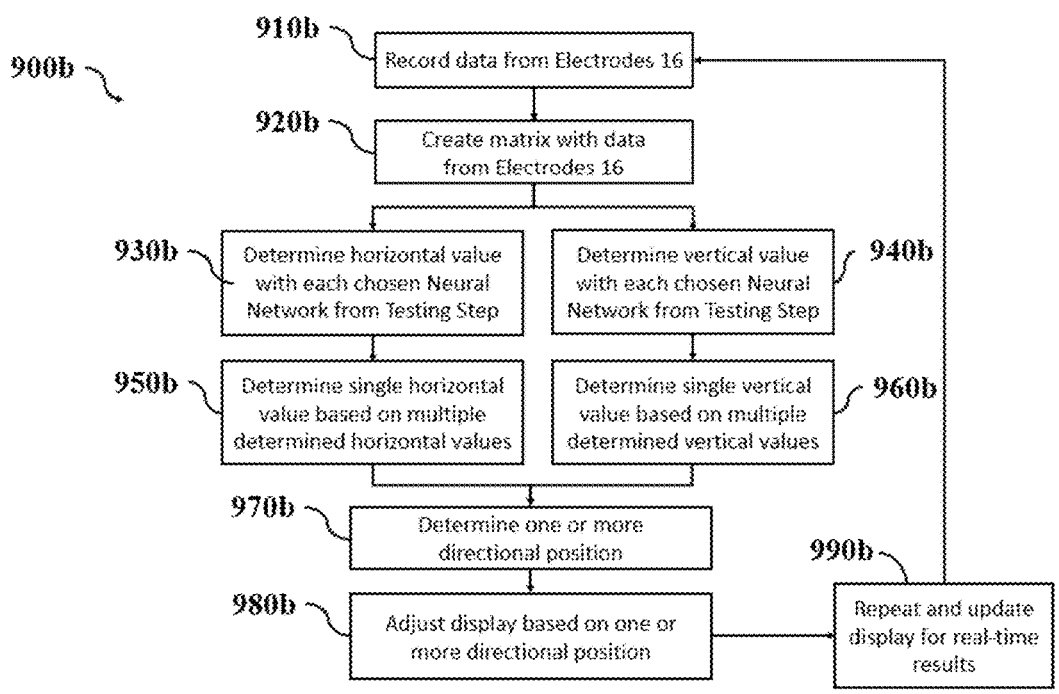
FIG. 33A illustrates an example embodiment of the method of FIG. 30A.

FIG. 33A illustrates an example method 900b illustrating how neural analysis system 10 may be operated to determine a user's desired directional position. It should be understood that some of the steps described herein may be reordered or omitted, while other steps may be added, without departing from the spirit and scope of the method 900b of FIG. 33A to 33C. It should further be understood that one or more of the steps of method 900b may be controlled by the control unit of neural analysis system 10 based on instructions stored on a memory and executed by a processor.

At step 910b, a user wearing headset 12 may begin a session. When the user begins the session, electrodes 16 are controlled to constantly or intermittently measure the user's transcranial electrical signals over a period of time. The data from electrodes 16 may be processed at headset 12 or transmitted to electronic device 14 via data transmission device 22 for further processing.

At step 920b, the transcranial electrical signals from the electrodes 16 are transformed into one or more matrices as described herein. In the illustrated embodiment, the transcranial electrical signal from each electrode 16 signifies the voltage at the electrode over a period of time. In an embodiment, the control unit breaks the transcranial electrical signal from each electrode 16 into smaller time segments (e.g., $t_1$, $t_2, t_3 \ldots t_n$), and then creates a matrix of values (e.g., a matrix of voltage data) using the time segments from one or more electrode 16.

Figure 33B:
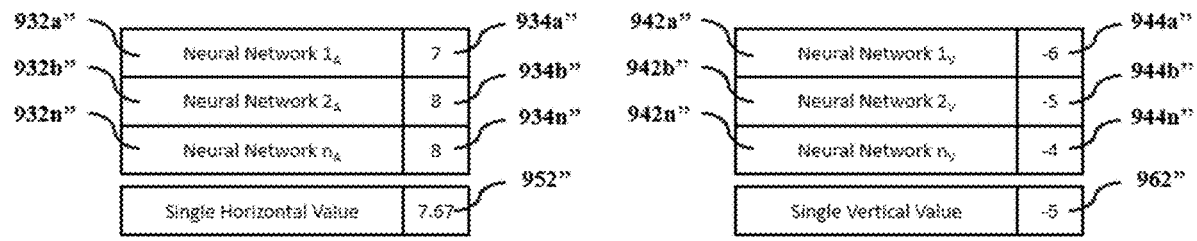
FIGS. 33B and 33C illustrate example embodiments of certain steps of the method of FIG. 33A.

At step 930b, the matrices are input into the trained neural networks 932" for a horizontal directional value, wherein the trained neural networks 932" were chosen from testing method 800b, and each trained neural network outputs a horizontal directional value 934". FIG. 33B illustrates an example embodiment showing a plurality of trained neural networks 932a", 932b" . . . 932n" for a horizontal directional value, wherein each trained neural network 932a", 932b" . . . 932n" outputs a horizontal directional value 934a", 934b" . . . 934n".

At step 940b, the matrices are input into the trained neural networks 942" for a vertical directional value, wherein the trained neural networks 932" were chosen from testing method 800a, and each trained neural network outputs a vertical value 944'. FIG. 33B illustrates an example embodiment showing a plurality of trained neural networks 942a', 942b' 942n' for a vertical directional value, wherein each trained neural network 942a', 942b' 942n' outputs a vertical directional value 944a', 944b' 944n'.

At step 950b, a single horizontal directional value 952" is determined based on the horizontal directional values 934" output by the trained neural networks 932" from step 930b. In an embodiment, the single horizontal directional value may be determined by averaging the results of the trained neural networks 932". For example, the example embodiment of FIG. 33B, the values 7, 8 and 8 have been averaged to return a single horizontal directional value of 7.67.

At step 960b, a single vertical directional value 962" is determined based on the vertical directional values 944" output by the trained neural networks 942" from step 940b. In an embodiment, the single vertical directional value may be determined by averaging the results of the trained neural networks 942". For example, the example embodiment of FIG. 32B, the values −6, −5 and −4 have been averaged to return a single vertical directional value of −5.

Figure 33C:
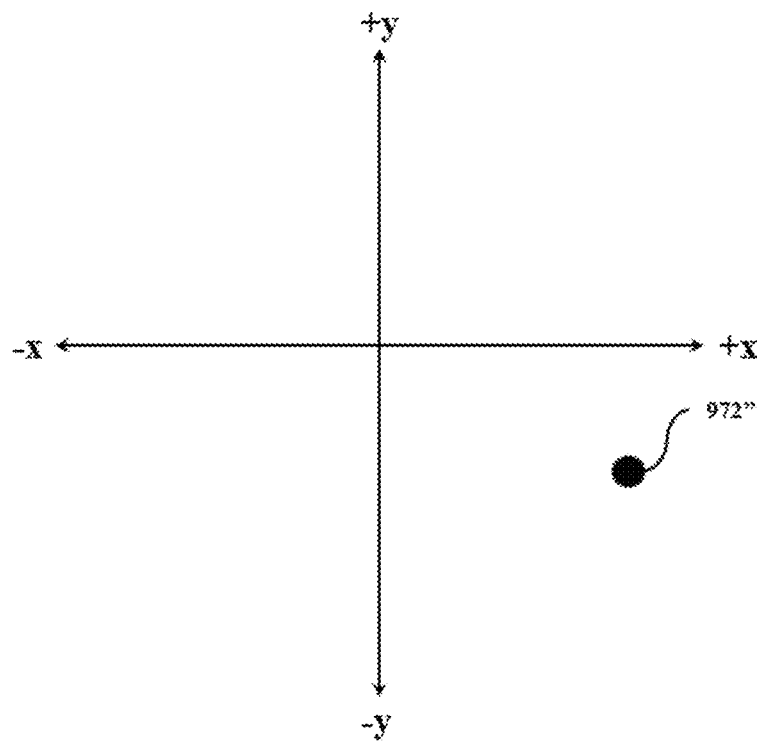

At step 970b, the control unit may determine one or more directional positions and/or confidence levels (e.g., confidence value and/or percentage) based on the single horizontal directional value 952" and single vertical directional value 962" determined at steps 950b and 960b. The control unit may determine the directional position desired by the user based on the distance between the single horizontal directional value 952" and single vertical directional value 962" plot point 972". For example, FIG. 33C shows the (−7.67, −5) plot point 972 using the single horizontal directional value 952" and single vertical directional value 962" determined at steps 950b and 960b.

At step 980b, the control unit causes user interface 50 of electronic device 14 to adjust a display based on the directional position desired by the user. For example, an icon or avatar on a display screen may be adjusted to the directional position.

At step 990b, the control unit returns to step 910b and processes another more current data matrix received from the electrodes 16. In this way, user interface 50 may continuously update the directional position in real time, until the user chooses to end the process. It should be understood that each of the steps of method 900b is happening in a split-second, providing the user with constant real-time updates regarding their desired directional position. Alternatively, method 900b may pause after step 980b until the user instructs to proceed to step 990b using user interface 50.

Although the above method is described in terms of horizontal and vertical data, it should be understood by those of ordinary skill in the art from this disclosure that a third user value of depth could also be used in the same way to achieve more accurate results. Fourth, fifth, etc. values can also be used as desired in the same way.

Additional Example Embodiments of Use of Headset (Music Composition, Drawing, Video Games, and Other Embodiments)

Although the methods of the present disclosure are described above in terms of a first embodiment which determines an emotional state and a second embodiment that determines a directional position, those of ordinary skill in the art will understand from this disclosure that the methods described herein are useful in a wide variety of other settings as well.

For example, in a music composition embodiment, a user could be enabled to compose music using the methods described herein. In such an embodiment, the user values and/or the user output states can relate to or include a musical composition, musical notes, tones, pitches, frequencies, volume levels, other audio element, etc. In such an embodiment, the user can perform a calibration, for example, by listening to musical notes or an entire song while recording voltage data from the headset 12. In this case, the electronic media 90 can include one or more audio recording. Additionally, the electronic media can include visual elements related to notes, tones, pitches, frequencies, etc. Then, once the user has calibrated the headset 12, the methods described above can enable the user can compose an original song or other audio recording by wearing the headset 12 while thinking of and/or speaking or singing.

Likewise, the directional embodiments herein can enable a user to draw or control aspects of video games using headset 12, optionally in combination with another input device such as the electronic device 14 described herein or a video game controller. The directional embodiments can be used to control various aspects of display screens such as creating original designs, moving characters, altering display and/or control elements, and other features. Those of ordinary skill in the art will understand from this disclosure the wide variety of possible applications which may be useful with the methods and apparatus described herein.

Several other examples of applications are discussed below, but it should be understood that these are examples only and that other applications are envisioned by the present disclosure.

First Group Therapy/Entertainment Embodiment

Various embodiments of neural analysis system 10 may be used in a group of people to determine how well the group knows each other and/or can read each other's emotions. Such a system may be used, for example, in a group therapy setting or in a friendly entertainment setting.

Figure 34:
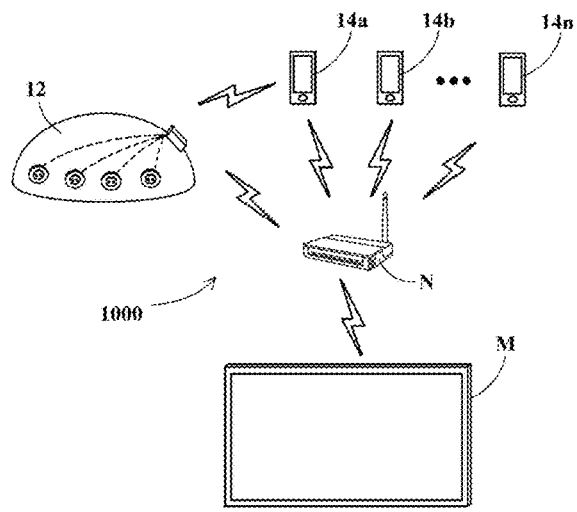
FIG. 34 illustrates an example embodiment of group system in which a group of acquaintances may utilize a neural analysis system according to the present disclosure.

FIG. 34 illustrates an example embodiment of group system 1000 in which a group of acquaintances may utilize neural analysis system 10 for a group therapy session and/or an enjoyable game night. In the illustrated embodiment, group system 1000 includes a plurality of electronic devices 14a, 14b, 14n (e.g., cellular phones, personal computers, etc.), which may be connected to a headset 12 and/or monitor M (e.g., television or computer monitor) via a wireless network N. Once connected via network N, electronic devices 14a, 14b, 14n may thereafter communicate with monitor M as the display screen for all users to view in unison.

Figure 35:
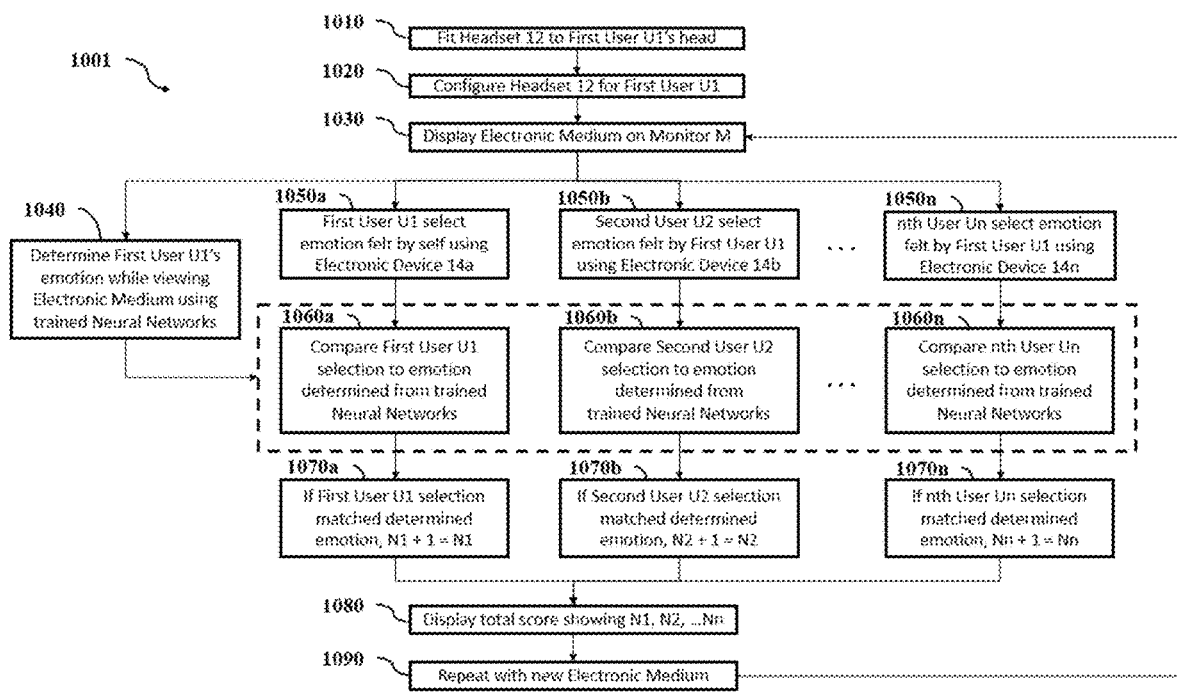
FIG. 35 illustrates an example embodiment of a method that may be performed with the group system of FIG. 34.

FIG. 35 illustrates an example embodiment of a method 1001 that may be performed with group system 1000. It should be understood that some of the steps described herein may be reordered or omitted, while other steps may be added, without departing from the spirit and scope of the method 1001 of FIG. 35. It should further be understood that one or more of the steps of method 1001 may be controlled by the control unit of neural analysis system 10 and/or group system 1000 based on instructions stored on a memory and executed by a processor.

In the illustrated embodiment, a first user $U_1$ of the group of people may place headset 12 on his or her head at step 1010 using the setup procedure described herein, and may configure headset 12 for use at step 1020 as described herein using an electronic device 14. If the user has used headset 12 in an earlier session, the user may also use stored calibration data as described herein, either with or without additional calibration at the time of use.

Figure 36A:
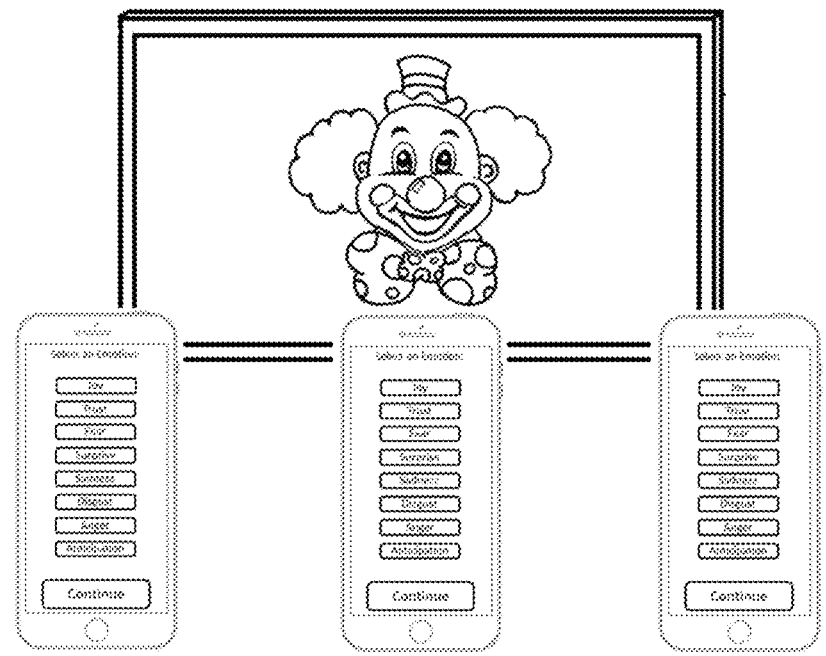
FIGS. 36A to 36C illustrate example embodiments of monitor and/or user interfaces during the method of FIG. 34.

At step 1030 (e.g., FIG. 36A), monitor M may exhibit an electronic medium 90 (e.g., photo, video and/or noise), which elicits an emotional response by first user $U_1$ wearing headset 12. As described herein, electrodes 16 of headset 12 may detect and store one or more data matrix related to transcranial electrical signals of first user $U_1$ while the electronic medium is exhibited.

At step 1040, the transcranial electrical signals from headset 12 are analyzed as described herein to determine one or more emotional states felt by first user $U_1$. As described above, one or more matrix of data from electrodes 16 may be analyzed by one or more trained neural network to determine arousal and valence values, which may then be used to determine one or more emotional states felt by first user $U_1$. In an embodiment, the closest emotional state to match the arousal and valence values may then be considered first user $U_1$'s exhibited emotional state E.

At steps 1050a, 1050b . . . 1050n, before first user $U_1$'s exhibited emotional state E is revealed, multiple persons (including, optionally, first user U1 who is wearing the headset) in the group makes a selection indicating which emotional state they believe first user U1 felt or displayed while the electronic medium 90 was displayed. Each person making a selection may use their own electronic device 14 so that the persons do not know each other's selections.

Figure 36B:
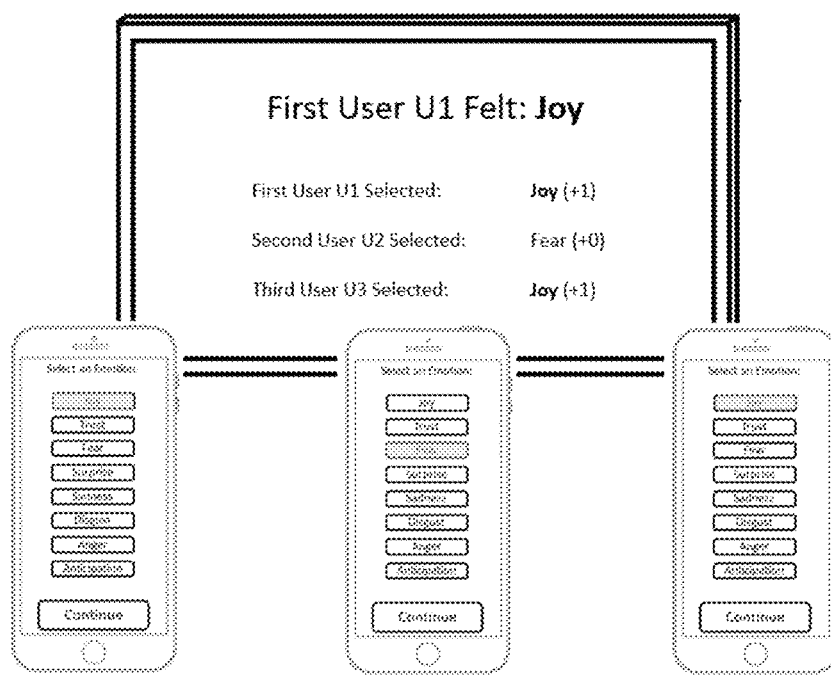

At steps 1060a, 1060b . . . 1060n, the selections of the members of the group are compared to the first user $U_1$'s exhibited emotional state E. If a selection matches the first user $U_1$'s exhibited emotional state E, the selector of the selection receives a point, e.g., a numerical or other value. In the illustrated embodiment (e.g., FIG. 36B), each user receives one (1) point per match at steps 1070a, 1070b . . . 1070n, but those of ordinary skill in the art will recognize from this disclosure that other scoring methods may be used. For example, in an embodiment, one user may score more points than another user for exhibited emotional state E based on a confidence level as described above. In another embodiment, each user may weight their answers based on their confidence in their own answers to gain more points per round.

Figure 36C:
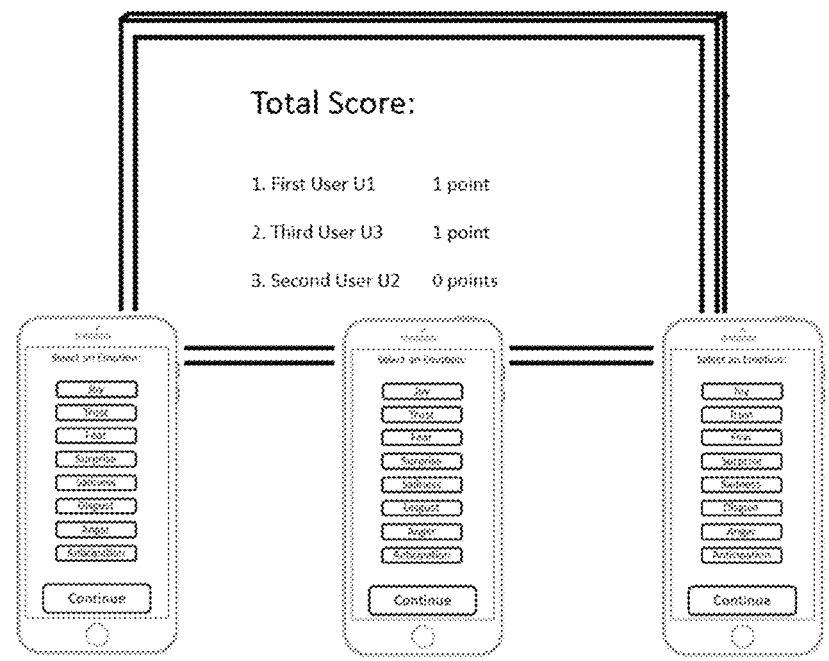

At step 1080 (e.g., FIG. 36C), the total scores are displayed on monitor M for all users to view.

At step 1090, method 1001 returns to step 1030 and a new electronic medium 90 is displayed on monitor M to begin the process again.

At the end of multiple rounds, the total score will indicate, for example, which person in the group is best at reading the emotional states of first user $U_1$. The process may then be repeated with second user $U_2$, etc. wearing headset 12. It is believed that such a process and result may be useful in a group therapy session and/or entertaining on a game night.

Second Group Therapy/Entertainment Embodiment

Another embodiment of neural analysis system 10 may be used in a group of people to determine emotional compatibility. Such a system may be used, for example, in a group therapy setting or in a friendly entertainment setting.

Figure 37:
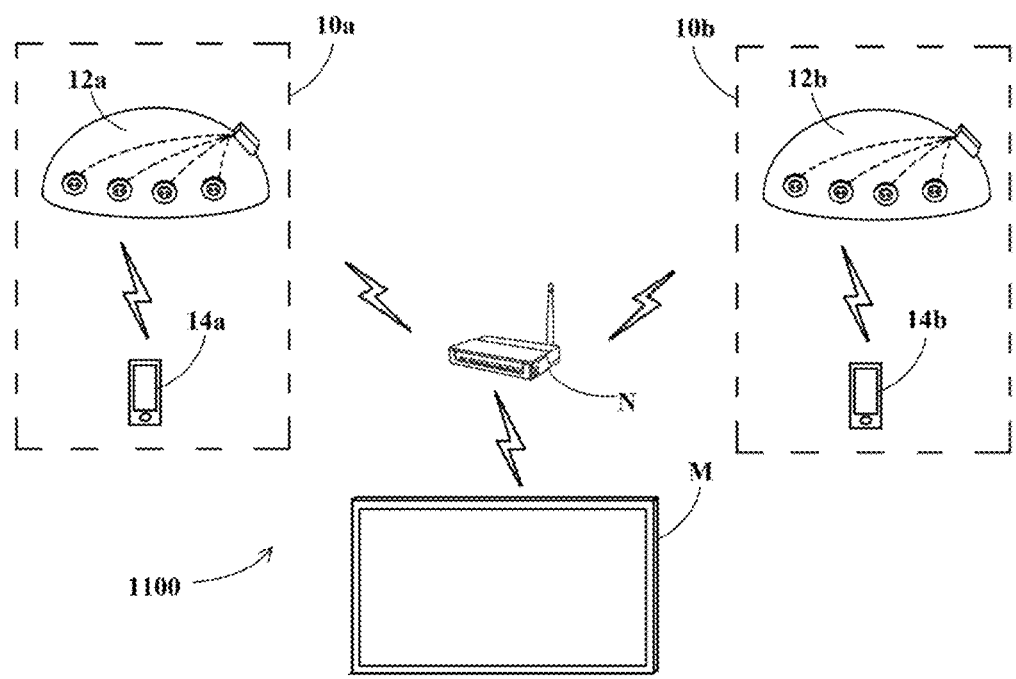
FIG. 37 illustrates an example embodiment of group system in which a group of acquaintances may utilize multiple neural analysis systems according to the present disclosure.

FIG. 37 illustrates an example embodiment of group system 1100 in which a group of acquaintances may utilize multiple neural analysis systems 10a, 10b . . . 10n for a group therapy session and/or an enjoyable game night. In the illustrated embodiment, group system 1100 includes a plurality of headsets 12, and one or more electronic device 14 (e.g., cellular phone, personal computer, etc.) and/or monitor M, which may all be directly or indirectly placed in communication, for example, via wireless network N.

In the illustrated embodiment, group system 1100 includes two headset 12a, 12b which are each paired with a respective electronic device 14a, 14b, but it should be understood that a single electronic device 14 could be substituted and paired with both headsets 12. Additionally, monitor M may act as the only electronic device 14. It should also be understood that more than two headsets may be used to accommodate more than two users.

Figures 38, 39:
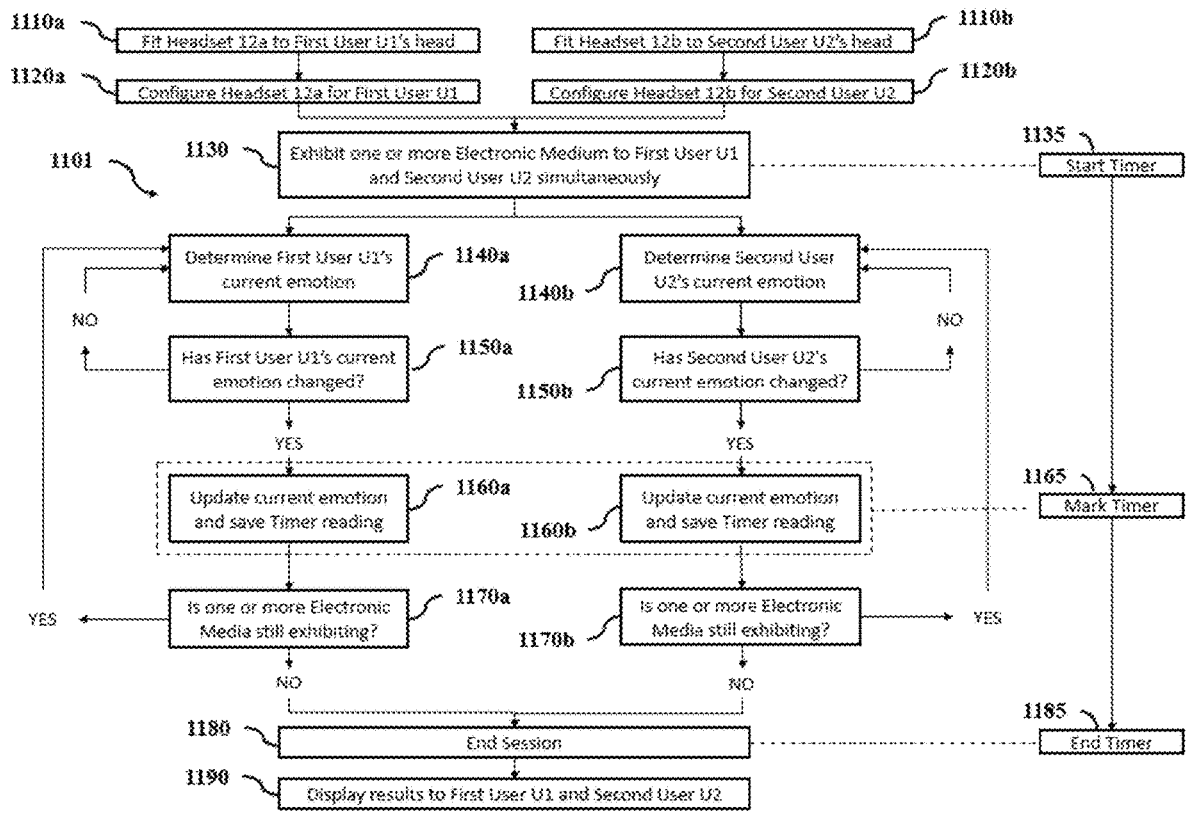
FIG. 38 illustrates an example embodiment of a method that may be performed with the group system of FIG. 37.
FIG. 39 illustrates an example embodiment of a monitor during the method of FIG. 38.

FIG. 38 illustrates an example embodiment of a method 1101 that may be performed with group system 1100. It should be understood that some of the steps described herein may be reordered or omitted, while other steps may be added, without departing from the spirit and scope of the method 1101 of FIG. 38. It should further be understood that one or more of the steps of method 1101 may be controlled by the control unit of neural analysis system 10 and/or group system 1100 based on instructions stored on a memory and executed by a processor.

At steps 1110a and 1110b, first user $U_1$ may place headset 12a on his or her head using the setup procedure described herein, and second user $U_2$ may place headset 12b on his or her head using the setup procedure described herein. Then, at steps 1120a and 1120b, first user $U_1$ may configure headset 12a for use as described herein using an electronic device 14, and second user $U_2$ may configure headset 12b for use as set described herein using an electronic device 14. If the users have used their headsets in an earlier session, the users may also use stored calibration data as described herein, either with or without additional calibration at the time of use.

At step 1130, at least one of an electronic device 14 and/or monitor M exhibits one or more electronic medium 90 for first user $U_1$ and second user U2 to view/hear simultaneously. A timer is also started at step 1135 to mark the beginning of the recording session. In an embodiment, the one or more electronic medium 90 is a movie (e.g., video and sound) that the first user $U_1$ and second user $U_2$ watch together on monitor M.

At step 1140*a*, first user $U_1$'s current emotional state is determined based on the data from headset 12*a*. The first user $U_1$'s current emotional state may be determined, for example, according to the methods described herein.

At step 1140*b*, second user $U_2$'s current emotional state is determined based on the data from headset 12*b*. The second user $U_2$'s current emotional state may be determined, for example, according to the methods described herein.

At step 1150*a*, first user $U_1$'s current emotional state detected at step 1140*a* is compared to a previously logged emotional state. If the first user $U_1$'s current emotional state is the same as the previously logged emotional state, then the method returns to step 1140*a* for another determination of a current emotional state. If there is no current emotional state logged for first user $U_1$, then the current emotional state is logged and then the method returns to step 1140*a* for another determination of a current emotional state.

If step 1150*a* determines that first user $U_1$'s current emotional state detected at step 1140*a* has changed since the previously logged emotional state, then the current emotional state is updated at step 1160*a* to reflect first user $U_1$'s present emotional state, and the time of the change is logged according to the timer at step 1165. If the one or more electronic medium is still exhibiting at step 1170*a*, then the method returns to step 1140*a* for another determination of a current emotional state.

At step 1150*b*, second user $U_2$'s current emotional state detected at step 1140*b* is compared to a previously logged emotional state. If the second user U2's current emotional state is the same as the previously logged emotional state, then the method returns to step 1140*b* for another determination of a current emotional state. If there is no current emotional state logged for second user $U_2$, then the current emotional state is logged and then the method returns to step 1140*b* for another determination of a current emotional state.

If step 1150*b* determines that second user $U_2$'s current emotional state detected at step 1140*b* has changed since the previously logged emotional state, then the current emotional state is updated at step 1160*b* to reflect second user $U_2$'s present state, and the time of the change is logged according to the timer at step 1165. If the one or more electronic medium is still exhibiting at step 1170*b*, then the method returns to step 1140*b* for another determination of a current emotional state.

If the one or more electronic medium 90 finishes exhibiting at steps 1170*a* and 1170*b*, then the session may end at step 1180, the timer may be stopped, and the results displayed for first user $U_1$ and second user $U_2$ at step 1190.

FIG. 39 illustrates an example embodiment of session results being displayed on monitor M. As illustrated, in an embodiment, the display may include a log of emotional states and overall percentage of time that the users' emotional states were the same (emotional compatibility %) or different.

In an alternative embodiment, the method may compare data besides emotions. For example, the method may compare valence and/or arousal data and calculate compatibility based on those or other values.

Market Research Embodiment

Another application which may utilize one or more neural analysis system 10, for example using group system 1100 and/or method 1101, is market research which utilizes one or more persons in a focus group of volunteers or test members of an intended audience. The focus group may evaluate, for example, a movie, television show, song, advertisement, video game, or other product. By logging the one or more user's emotional states during the focus group, a large emotional state dataset may be compiled so that the creator of the product at the center of the focus group may determine whether the intended emotional states are being evoked and/or whether changes need to be made to the product.

Video Gaming Enhancement Embodiment Using Emotions

Various embodiments of neural analysis system 10 may be used with a video gaming system to have an effect on the game being played. For example, one popular game genre utilizes in-game avatars, one or more of which may be controlled by game players. It is therefore possible to use neural analysis system 10 to mirror the game player's emotional states with an in-game avatar, enhancing the realness of the gaming experience.

Figure 40:
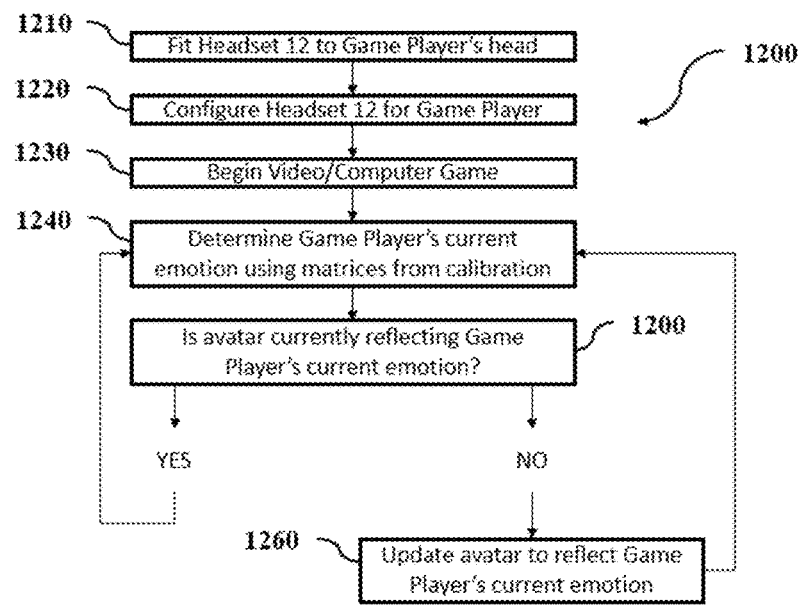
FIG. 40 illustrates an example embodiment of a method of using neural analysis system with a video gaming system.

FIG. 40 illustrates an example embodiment of a method 1200 that may utilize neural analysis system 10 with a video gaming system. It should be understood that some of the steps described herein may be reordered or omitted, while other steps may be added, without departing from the spirit and scope of the method 1200 of FIG. 40. It should further be understood that one or more of the steps of method 1200 may be controlled by the control unit of neural analysis system 10 based on instructions stored on a memory and executed by a processor. In the illustrated method, headset 12 and or electronic device 14 may connect wirelessly to the gaming system and/or electronic device 14 itself may be or include the gaming system.

In the illustrated embodiment, a game player may place headset 12 on his or her head at step 1210 using the setup procedure described herein, and may configure headset 12 for use at step 1220 as described herein using an electronic device 14. If the game player has used headset 12 in an earlier session, the game player may also use stored calibration data as described herein, either with or without additional calibration at the time of use.

At step 1230, the game players may begin playing the video game, wherein the avatar in the video game is linked to the game player's headset. It should be understood that step 1230 may be performed at any time before or after steps 1210, 1220, or 1240.

At step 1240, neural analysis system 10 may begin the real-time emotional state detection method shown and described herein, resulting in a current emotional state E for the game player at any given time.

At step 1250, neural analysis system 10 may determine whether the avatar in the video game is currently reflecting the game player's determined current emotional state E. If the avatar is already reflecting the game player's determined current emotional state E, then method 1200 may return to step 1240 for another real-time detection of the game player's current emotional state E. If the avatar is not reflecting the game player's determined current emotional state E, then method 1200 may proceed to step 1260 to update the avatar, and then return to step 1240 for another real-time detection of the game player's current emotional state E.

In an alternative embodiment, a game player may utilize headset 12 without determining a current emotional state E, by instead updating the avatar based on changes in arousal and/or valence data. For example, changes in avatar usage or other gameplay elements may be altered each time the game player crosses certain thresholds for valence and/or arousal.

In other embodiments, the player's emotional states and/or valence and/or arousal data may affect other areas of game play besides the in-game avatar mirroring the player's emotions. For example, other aspects of gameplay such as unlocking special features or awarding points may occur when the game player experiences particular emotional states and/or reaches certain levels of valence and/or arousal. Those of ordinary skill in the art will recognize from this disclosure additional methods that advantageously utilize neural analysis system 10 with a gaming system.

Medical Treatment Embodiments

Certain medical treatment embodiments may also benefit from the use of one or more neural analysis system 10. For example, a neural analysis system 10 may aid in treating bipolar disorder, schizophrenia, depression, and phantom limb syndrome. In an embodiment, a neural analysis system 10 according to the present disclosure may benefit a medical patient with these or other conditions, for example, by alerting a physician when certain emotional states are present and/or by causing a medicament to be administered to the patient when certain emotional states are present.

Figure 41A:
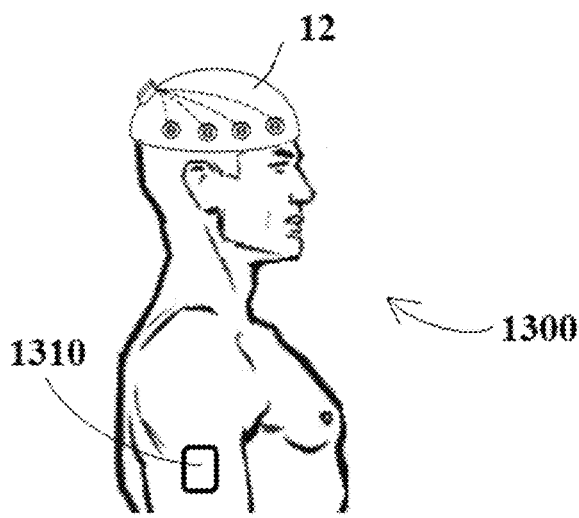
FIG. 41A illustrates an example embodiment of a medical device according to the present disclosure.

FIG. 41A illustrates an example embodiment of a medical device 1300 that utilizes a neural analysis system 10 according to the present disclosure. In the illustrated embodiment, medical device 1300 includes a headset 12 and a drug delivery device 1310 which are placed in wireless communication with each other. In an embodiment, a wired connection may also be used. In an embodiment, a separate electronic device 14 may be used to coordinate and program headset 12 and drug delivery device 1310.

Figure 41B:
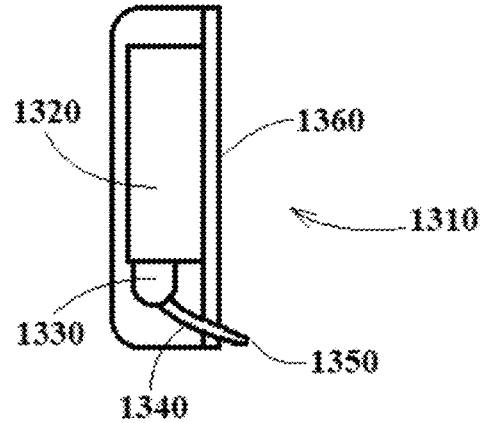
FIG. 41B illustrates a cross-sectional view of an example embodiment of a drug delivery device for use as part of the medical device of FIG. 41A.

FIG. 41B illustrates an example embodiment of drug delivery device 1310 of medical device 1300 in more detail. In the illustrated embodiment, drug delivery device 1310 includes a reservoir 1320 configured to store a medicament, a pump or valve 1330 enabling the medicament to exit the reservoir 1320, and a needle 1340 including a sharp tip 1350 configured to pierce a patient's skin when worn by the patient. In use, an attachment device 1360 such as an adhesive may attach drug delivery device 1310 to the patient's body, wherein the sharp tip 1350 of needle 1340 may pierce the patient's skin to place the reservoir 1320 in fluid communication with the patient's body so that the medicament may be delivered to the patient from the reservoir. When pump or valve 1330 is thereafter activated, the medicament is pumped and/or enabled to flow into the patient's body.

In the illustrated embodiment, medical device 1300 may further include an additional electronic device 14 having a control unit, and/or a control unit may be contained within headset 12 and/or drug delivery device 1310. In an embodiment, an electronic device 14 may be used to configure headset 12 according to the methods described herein, and then headset 12 may communicate wirelessly with drug delivery device 1310. In another embodiment, drug delivery device 1310 may act as or include electronic device 14.

In an embodiment, the control unit may be programmed to continuously or intermittently detect transcranial electrical signals from the patient. When certain thresholds are met, the control unit may activate pump or valve 1330 to deliver the medicament to the patient. In an embodiment, the control unit may activate pump or valve 1330 when certain voltage thresholds detected by one or more electrode 16 of headset 12 are met. In an embodiment, the control unit may activate pump or valve 1330 when certain arousal or valence thresholds are met. In an embodiment, the control unit may activate pump or valve 1330 when certain emotional states are detected from the patient.

Therapy Enhancement Embodiment

Certain therapeutic treatment embodiments may also benefit from the use of one or more neural analysis system 10. For example, a neural analysis system 10 may aid enhance Eye Movement Desensitization and Reprocessing (EMDR) treatment. With EMDR treatment, a therapist uses, for example, a light strip to erase or lessen traumatic memories for a patient. By utilizing a neural analysis system 10 according to the present disclosure before and after an EMDR treatment, it can be determined whether the EMDR treatment was successful, since arousal and valence values should decrease in the patient if the effects of the traumatic memory are lessened.

Modifications in addition to those described above may be made to the structures and techniques described herein without departing from the spirit and scope of the disclosure. Accordingly, although specific embodiments have been described, these are examples only and are not limiting on the scope of the disclosure.

The invention claimed is:

1. A method for interpreting a user's transcranial electrical signals, the method comprising:
   receiving data regarding the user's transcranial electrical signals;
   creating a data matrix from the data regarding the user's transcranial electrical signals;
   converting the data matrix into a first user value;
   converting the data matrix into a second user value;
   defining a user output state based on the first user value and the second user value; and
   exhibiting the user output state.

2. The method of claim 1, which includes detecting the user's transcranial electrical signals via at least one electrode.

3. The method of claim 1, which includes enabling the user to perform a calibration procedure in which the user defines at least one user output state.

4. The method of claim 1, wherein converting the data matrix into the first user value or converting the data matrix into the second user value includes processing the data matrix with at least one neural network.

5. The method of claim 1, wherein converting the data matrix into the first user value includes processing the data matrix with a first neural network to determine the first user value, and wherein converting the data matrix into the second user value includes processing the data matrix with a second neural network to determine the second user value.

6. The method of claim 1, wherein exhibiting the user output state includes altering a display or creating or altering an audio element based on the user output state.

* * * * *